US008557800B2

(12) United States Patent
Smith et al.

(10) Patent No.: US 8,557,800 B2
(45) Date of Patent: Oct. 15, 2013

(54) SPHINGOSINE KINASE INHIBITORS

(75) Inventors: Charles D. Smith, Mt. Pleasant, SC (US); Kevin J. French, Mohnton, PA (US); Yan Zhuang, Hershey, PA (US)

(73) Assignee: Apogee Biotechnology Corporation, Hershey, PA (US)

( * ) Notice: Subject to any disclaimer, the term of this patent is extended or adjusted under 35 U.S.C. 154(b) by 43 days.

(21) Appl. No.: 13/277,044

(22) Filed: Oct. 19, 2011

(65) Prior Publication Data

US 2012/0095004 A1 Apr. 19, 2012

Related U.S. Application Data

(62) Division of application No. 11/963,838, filed on Dec. 23, 2007, now Pat. No. 8,063,248, which is a division of application No. 11/424,423, filed on Jun. 15, 2006, now Pat. No. 7,338,961.

(60) Provisional application No. 60/691,563, filed on Jun. 17, 2005.

(51) Int. Cl.
*A61K 31/165* (2006.01)
(52) U.S. Cl.
USPC ....... 514/195; 514/255.01; 514/617; 514/319
(58) Field of Classification Search
USPC .................... 514/195, 617, 255.01
See application file for complete search history.

(56) References Cited

U.S. PATENT DOCUMENTS

| | | | |
|---|---|---|---|
| 3,352,912 A | 11/1967 | William | |
| 3,657,273 A | 4/1972 | Krimmel | |
| 3,663,565 A | 5/1972 | Krimmel | |
| 4,053,509 A | 10/1977 | Faro et al. | |
| 4,332,806 A | 6/1982 | Atsumi et al. | |
| 4,349,552 A | 9/1982 | Takaya et al. | |
| 5,061,703 A | 10/1991 | Bormann et al. | |
| 5,595,995 A | 1/1997 | Chan et al. | |
| 6,649,600 B1 | 11/2003 | Kiesman et al. | |
| 2004/0034075 A1 | 2/2004 | Smith | |
| 2006/0270630 A1 | 11/2006 | Smith et al. | |
| 2006/0270631 A1 | 11/2006 | Smith et al. | |

FOREIGN PATENT DOCUMENTS

| | | |
|---|---|---|
| WO | WO 99/26927 | 6/1999 |
| WO | WO 2004/089470 | 10/2004 |
| WO | WO 2006/048750 | 5/2006 |
| WO | WO 2006/100502 | 9/2006 |

OTHER PUBLICATIONS

Tseng, C.C. et al., "N-[(Aryl Substituted Adamantane)Alkyl] 2-Mercaptoacetamidines, Their Corresponding Disulfides and S-Phosphorothioates," Tetrahedron, vol. 44, No. 17, pp. 1893-1904 (1988).

Danilenko, G.I. et al., "Synthesis and Protective Properties of Phenyladamantane With Respect to Rabies Virus," Pharm. Chem. J., vol. 32, No. 2, pp. 83-85 (1998).
Olson, S. et al., "Adamantyl triazoles as selective inhibitors of 11-beta-hydroxysteroid dehydrogenase type 1," Bioorg. & Med. Chem. Letts., vol. 15, pp. 4359-4362 (2005).
Lavrova, L.N. et al., "Synthesis and Radioprotective Activity of Some Derivatives of N-(3-Aryladamant-1-Ylmethyl)Mercaptoacetamidine," Pharm. Chem. J., 1993, pp. 585-587.
Stepanov F.N. et al. "Adamantane and its derivatives. IV. Acid hydrolysis of acylamino derivatives of admanantane," Chem. Abstracts database accession No. 1966:403703 (1966).
Danilenko, G. N. et al.; Synthesis and Biological Activity of Adamantane Derivatives; Pharmaceutical Chemistry Journal English Translation of Khimiko—Farmatsevticheskii Zhurnal, vol. 7, No. 10, pp. 621-622, Oct. 1973.
Safonova O.A. et al.; Synthesis and Biological Activity of 5-(Adamant-1-yl)Salicylic Acid, 3-(4-Hydroxyphenyl) adamantanecarboxylic Acid and Some of their Derivatives; Translated from Khimiko-farmatsevticheskii Zhurnal, vol. 23, No. 9, pp. 1094-1098, Sep. 1989.
Handa, Indra et al.; Synthesis of 3-Aryl-1-adamantanemethylamines; J. Chem. Eng. Data 1984, 29, 223-225.
Danilenko, G. I. et al.; Bacteriostatic effect of adamantanecarboxylic acids; Fiziologicheski Aktivnye Veshchestva (1966-1992) (1975), 7, 144-7; Chemical Abstracts accession No. 1975:496537.
Pozdnyakov, V. V. et al.; Synthesis and Reactivity of 3-R-1-Adamantyl Methyl Ketones; Russian Journal of Organic Chemistry, vol. 37, No. 9, 2001 pp. 1128-1231.
Fytas, George et al; 3-Cyclopentyl-1-Adarnantanannines and Adamantanemethanamines. Antiviral Activity Evaluation and Convulsions Studies; IL Farmaco, 49 (10), 641-647 (1994).
Stepanov, F. N. et al; Adamantane and its derivatives. XXV. Reaction of bromomethyl ketones of adamantanes with formamide and aniline; (Translated from Zhurnal Organicheskoi Khimii (1970), 6(6), 1195-8).
Scvekhgeimer, G.A. et al.; Synthesis and properties of azoles and their deriivatives. XXX. Synthesis of heterocyclic compounds based on adamantane-1,3-dicarboxylic acid dinitrile; Khimiya Geterotsiklicheskikd Soedinenii (1976), (12), 1654-7.
Kontonassios, Demetrios et al.; 3-(Dialkylamino)methyladamantane-1-carboxylic Acids; Journal of Medical Chemistry, vol. 12, No. 1, pp. 170-172, Jan. 1969.
Frisherman, R. B. et al; N-Methylstearylamides of adamantanecarboxylic acids; U.S.S.R. Otkrytiya, Izobret., Prom. Obraztsy, Tovamye Znaki 1974, 51(44), 51-2.
No, B.I. et al; Synthesis of N,N'-diphenyl-1-1,3-adamantanebis (carboximidoyl chloride) and adamantanebis (carboximidates); Russian Journal of General Chemistry (Translation of Zhurnal Obshchei Khimii) (1999), 69(5), 843-844.
Horvat, Stefica; Tumor-Cell-Targeted Methionine-enkephalin Analogues Containing Unnatural Amino Acids: Design, Synthesis, and in Vitro Antitumor Activity; J. Med. Chem. 2006, 49, 3136-3142.

(Continued)

*Primary Examiner* — David K O Dell
(74) *Attorney, Agent, or Firm* — McDonnell Boehnen Hulbert & Berghoff LLP

(57) ABSTRACT

The invention relates to substituted adamantane compounds, pharmaceutical compositions thereof, processes for their preparation, and methods for inhibiting sphingosine kinase and for treating or preventing hyperproliferative disease, inflammatory disease, or angiogenic disease.

20 Claims, 10 Drawing Sheets

(56) References Cited

OTHER PUBLICATIONS

SciFinder substructure search results, aminoethylpyridine, performed Aug. 9, 2007, 26 pages.

SciFinder substructure search results, aminomethylpyridine (commerically available only), performed Aug. 9, 2007, 21 pages.

El-Sherbeny M. A.; "Adamantane Derivatives, Part II: Synthesis DNA Binding and Antitumor Evaluation;" Medical Chemistry Research 2002 United States, vol. 1, No. 2, pp. 74-86, 2002.

Kozlov N.G. et al.; "Reductive Amination of 1-Acetyladamantane with Nitriles," Chemical Abstracts Service, Columbus, OH, retrieved from STN Database accession No. 1985:804596.

Melindez et al.; "Sphingosine kinase signalling in immune cells: Potential as novel therapeutic targets," Biochimica et Biophysica Acta 2007, in press.

Johnson, A.W.; "Invitation to Organic Chemistry 1999 Jones and Bartless," Mississauga, Canada, pp. 24.

Hal Bender; "Nomenclature," Clackamas Community College online: "http://dl.clackamas.cc.or.us/ch106-05/nomencla1.htm2003," May 5, 2007.

"R-5.7.8 Amides, imides, and hydrazides" online "http://www.acdlabs.com/iupac/nomenclature/93r93_543.htm," May 2, 2007.

Ferdinand, C.Y. et al.; "3- and 4-Pyridylalkyl Adamantanecarboxylates: Inhibitors of Human Cytochrome P450" . . . "Potential Nonsteroidal Agents for the Treatment of Prostatic Cancer," vol. 39, pp. 3319-3323, 1996.

Price, Charles; "The alkylation of aromatic compounds by the Friedel-crafts method," In Organic Reactions vol. III, Wiley: New York, pp. 1-19, 1947.

Handa, I., et al.; Journal of Chemical Engineering Data 1984, vol. 29, pp. 223-225.

Salvatore, et al.; "Cesium Effect: High Chemoselectivity in Direct N-Alkylation of Amines," J. Org. Chem, 2002, 67, 674-683.

Silverman, R.B., The Organic Chemistry of Drug Design and Drug Action, 1992, Academic: New York, p. 19.

Xiang, et al., "Discovery of novel sphingosine kinase-1 inhibitors. Part 2," Bioorganic & Medicinal Chemistry Letters 2010, 20, 4550-4554.

SPHINGOSINE KINASE INHIBITORS

REFERENCE TO RELATED APPLICATIONS

This application is a divisional of U.S. patent application Ser. No. 11/963,838, filed Dec. 23, 2007 now U.S. Pat. No. 8,063,248, which is a divisional of U.S. patent application Ser. No. 11/424,423, filed Jun. 15, 2006 now U.S. Pat. No. 7,338,961, which is a non-provisional application claiming priority under 35 U.S.C. section 119(e) to provisional application No. 60/691,563 filed Jun. 17, 2005, the contents of each of which are incorporated herein by reference in their entirety.

GOVERNMENT SPONSORSHIP

This invention was made with government support Grant R43 CA097833 awarded by the United States Public Health Service. Accordingly, the US government may have certain rights in this invention.

FIELD OF THE INVENTION

The invention relates to compounds that are capable of inhibiting sphingosine kinase and to processes for the synthesis of these compounds. The invention also relates to pharmaceutical compositions comprising these compounds and to methods for the use of these compounds and pharmaceutical compositions for treating or preventing hyperproliferative disease, inflammatory disease, or angiogenic disease.

BACKGROUND OF THE INVENTION

The mechanisms and effects of the interconversion of sphingolipids have been the subjects of a growing body of scientific investigation. Sphingomyelin is not only a building block for cellular membranes but also serves as the precursor for potent lipid messengers that have profound cellular effects. As described below, stimulus-induced metabolism of these lipids is critically involved in the biology of hyperproliferative, inflammatory and angiogenic diseases. Consequently, manipulation of these metabolic pathways is a novel method for the therapy of a variety of diseases.

Ceramide is produced by the hydrolysis of sphingomyelin in response to several stimuli, including growth factors and inflammatory cytokines. Ceramide induces apoptosis in cancerous cells. Additionally, ceramide can be hydrolyzed by the action of ceramidase to produce sphingosine. Sphingosine is then phosphorylated by sphingosine kinase (SK) to produce sphingosine-1-phosphate (S1P). Evidence demonstrates that S1P is a critical second messenger that exerts proliferative and anti-apoptotic actions. Additionally, ceramide enhances apoptosis in response to anticancer drugs including Taxol and etoposide. Furthermore, ceramide appears to induce apoptosis in tumor cells without killing quiescent normal cells. Studies in various cell lines consistently indicate that S1P is able to induce proliferation and protect cells from apoptosis. Together, the data demonstrate that the balance between cellular levels of ceramide and S1P determines whether a cancer cell proliferates or dies by apoptosis. Therefore, altering this balance by reducing the production of S1P within hyperproliferating cells is an effective method to treat disorders arising from abnormal cell proliferation.

Sphingosine kinase is responsible for S1P production in cells. RNA encoding SK is expressed in most tissues, with higher levels often occurring in tumor tissue than in corresponding normal tissue. A variety of proliferative factors, including Protein Kinase C (PKC) activators, fetal calf serum, Platelet-Derived Growth Factor, Epidermal Growth Factor, and Tumor Necrosis Factor-alpha (TNFα) rapidly elevate cellular SK activity. This promotes proliferation and inhibits apoptosis of the target cells. Additionally, an oncogenic role of SK has been demonstrated. In these studies, transfection of SK into NIH/3T3 fibroblasts was sufficient to promote foci formation and cell growth in soft-agar, and to allow these cells to form tumors in NOD/SCID mice. Additionally, inhibition of SK by transfection with a dominant-negative SK mutant or by treatment of cells with the nonspecific SK inhibitor D-erythro-N,N-dimethylsphingosine (DMS) blocked transformation mediated by oncogenic H-Ras. Since abnormal activation of Ras, as well as overexpression and mutation of ras family genes, frequently occurs in cancer, these findings indicate a significant role of SK in this disease.

In addition to its role in regulating cell proliferation and apoptosis, S1P has been shown to have several important effects on cells that mediate immune functions. Platelets, monocytes and mast cells secrete S1P upon activation, promoting inflammatory cascades at the site of tissue damage. Activation of SK is required for the signaling responses since the ability of TNFα to induce adhesion molecule expression via activation of Nuclear Factor Kappa B (NFκB) is mimicked by S1P and is blocked by DMS. Similarly, S1P mimics the ability of TNFα to induce the expression of Cyclooxygenase-2 (COX-2) and the synthesis of prostaglandin $E_2$ ($PGE_2$), and knock-down of SK by RNA interference blocks these responses to TNFα but not S1P. S1P is also a mediator of $Ca^{2+}$ influx during neutrophil activation by TNFα and other stimuli, leading to the production of superoxide and other toxic radicals. Therefore, reducing the production of S1P within immune cells and their target tissues may be an effective method to treat disorders arising from abnormal inflammation. Examples of such disorders include inflammatory bowel disease, arthritis, atherosclerosis, asthma, allergy, inflammatory kidney disease, circulatory shock, multiple sclerosis, chronic obstructive pulmonary disease, skin inflammation, periodontal disease, psoriasis and T cell-mediated diseases of immunity.

Angiogenesis refers to the state in the body in which various growth factors or other stimuli promote the formation of new blood vessels, and this process is critical to the pathology of a variety of diseases. In each case, excessive angiogenesis allows the progression of the disease and/or the produces undesired effects in the patient. Since conserved biochemical mechanisms regulate the proliferation of vascular endothelial cells that form these new blood vessels, identification of methods to inhibit these mechanisms are expected to have utility for the treatment and prevention of a variety of diseases. More specifically, certain growth factors have been identified that lead to the pathogenic angiogenesis. For example, Vascular Endothelial Growth Factor (VEGF) has angiogenic and mitogenic capabilities. Specifically, VEGF induces vascular endothelial cell proliferation, favoring the formation of new blood vessels. Sphingosine kinase is an important mediator of the actions of VEGF. For example, SK has been shown to mediate VEGF-induced activation of protein kinases. VEGF has also been shown to specifically induce S1P receptors, associated with enhanced intracellular signaling responses to S1P and the potentiation of its angiogenic actions. Production of S1P by SK stimulates NFκB activity leading to the production of COX-2, adhesion molecules and additional VEGF production, all of which promote angiogenesis. Furthermore, the expression of endothelial isoforms of nitric oxide synthase (eNOS) is regulated by SK, and eNOS too subsequently modulates angiogenesis. Therefore, reducing the production of S1P within endothelial cells is likely to be an effective method to treat disorders arising from abnormal angiogenesis. Examples of such disorders include arthritis, cancer, psoriasis, Kaposi's sarcoma, hemangiomas, myocardial angiogenesis, atherosclerosis, and ocular angiogenic diseases.

In spite of the high level of interest in sphingolipid-derived signaling, there are very few known inhibitors of the enzymes of this pathway and the utility of pharmacologic inhibition of SK in vivo has not been previously demonstrated. In particular, the field suffers from a lack of potent and selective inhibitors of SK. Pharmacological studies to date have used three compounds to inhibit SK activity: DMS, D,L-threo-dihydrosphingosine and N,N,N-trimethyl-sphingosine. However, these compounds are not specific inhibitors of SK and have been shown to inhibit several other protein and lipid kinases. Therefore, improved inhibitors of SK are required for use as antiproliferative, anti-inflammatory and anti-angiogenic agents.

SUMMARY OF THE INVENTION

In this application, we describe novel compounds that display the above-mentioned desirable activities. Accordingly, the invention encompasses the compounds of formula (I), shown below, processes for the synthesis of these compounds, pharmaceutical compositions containing such compounds, and methods employing such compounds or compositions in the treatment or prevention of hyperproliferative disease, inflammatory disease, or angiogenic disease, and more specifically compounds that are capable of inhibiting SK.

In one aspect, the invention provides compounds of formula I:

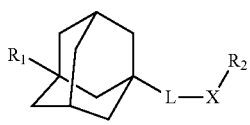

(I)

and pharmaceutically acceptable salts thereof, wherein

L is a bond or is —C($R_3$,$R_4$)—;

X is —C($R_3$,$R_4$)N($R_5$)—, —C(O)N($R_4$)—, —N($R_4$)C(O)—, —C($R_4$,$R_5$)—, —N($R_4$)—, —O—, —S—, —C(O)—, —S(O)$_2$—, —S(O)$_2$N($R_4$)— or —N($R_4$)S(O)$_2$—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

$R_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (=O), —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

wherein the alkyl and ring portion of each of the above $R_1$, $R_2$, and $R_3$ groups is optionally substituted with up to 5 groups that are independently ($C_1$-$C_6$) alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, and NH$_2$; and $R_4$ and $R_5$ are independently H or alkyl, provided that when $R_3$ and $R_4$ are on the same carbon and $R_3$ is oxo, then $R_4$ is absent.

The invention also provides processes for the synthesis of compounds of formula I.

The invention also provides pharmaceutical compositions comprising a compound or salt of formula I and at least one pharmaceutically acceptable carrier, solvent, adjuvant or diluent.

The invention also provides methods for the treatment or prevention of hyperproliferative disease, inflammatory disease, or angiogenic disease.

The invention also provides methods for inhibiting sphingosine kinase in a cell.

The compounds of the invention are potent and selective inhibitors of SK. Therefore, the invention provides inhibitors of SK which are useful as antiproliferative, anti-inflammatory and anti-angiogenic agents.

Specific preferred embodiments of the invention will become evident from the following more detailed description of certain preferred embodiments and the claims.

DESCRIPTION OF THE PREFERRED EMBODIMENT

Figure 1:
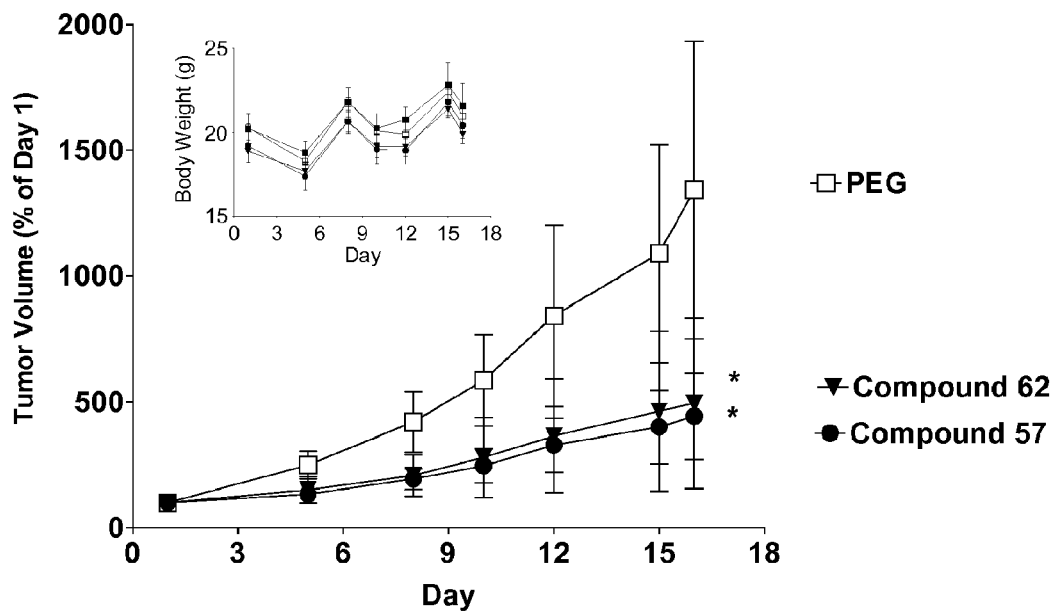
FIG. 1. Inhibition of tumor growth by SK inhibitors. Balb/c female mice were injected subcutaneously with JC murine adenocarcinoma cells suspended in PBS. After palpable tumor growth, animals were treated by oral gavage of either 100 µl of PEG400 (control, open squares) or 100 mg/kg of Compound 62 (triangles) or Compound 57 (circles) on odd numbered days. Whole body weight and tumor volume measurement were performed for up to 18 days. * p<0.05. Inset: Averaged body weights of mice from each group during course of study.

All patents and publications referred to herein are hereby incorporated by reference for all purposes.

Unless the substituents for a particular formula are expressly defined for that formula, they are understood to carry the definitions set forth in connection with the preceding formula to which the particular formula makes reference.

As noted above, the invention provides compounds of formula I:

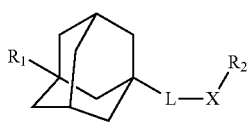

(I)

and pharmaceutically acceptable salts thereof, wherein

L is a bond or is —C($R_3$,$R_4$)—;

X is —C($R_3$,$R_4$)N($R_5$)—, —C(O)N($R_4$)—, —N($R_4$)C(O)—, —C($R_4$,$R_5$)—, —N($R_4$)—, —O—, —S—, —C(O)—, —S(O)$_2$—, —S(O)$_2$N($R_4$)— or —N($R_4$)S(O)$_2$—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

$R_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (═O), —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

wherein the alkyl and ring portion of each of the above $R_1$, $R_2$, and $R_3$ groups is optionally substituted with up to 5 groups that are independently ($C_1$-$C_6$) alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, NH$_2$; and $R_4$ and $R_5$ are independently H or alkyl, provided that when $R_3$ and $R_4$ are on the same carbon, and $R_3$ is oxo, then $R_4$ is absent.

Preferred compounds of formula I include compounds wherein L is a bond.

Preferred compounds of formula I also include compounds wherein L is a bond and X is —C($R_3$$R_4$)—. More preferably, $R_3$ and $R_4$ form an oxo (═O) group.

Preferred compounds of formula I also include compounds $R_1$ is H.

Preferred compounds of formula I also include compounds wherein $R_1$ is optionally substituted aryl. Preferably, aryl is phenyl. Also preferably, phenyl is unsubstituted or is substituted with halogen. Preferred halogen substituents are Cl and F.

Preferred compounds of formula I further include compounds wherein $R_2$ is OH.

Preferred compounds of formula I further include compounds wherein $R_2$ is $C_1$-$C_6$ alkyl, more preferably $C_1$-$C_3$ alkyl, and even more preferably, CH$_3$.

Preferred compounds of formula I further include compounds wherein $R_2$ is alkenylaryl. Preferably, the aryl portion of alkenylaryl is phenyl or naphthyl, optionally substituted with 1 or 2 of halogen, cyano, or hydroxy.

Preferred compounds of formula I further include compounds wherein $R_2$ is -alkenyl-heteroaryl.

Preferred compounds of formula I further include compounds wherein $R_2$ is -alkenyl-heteroaryl-aryl.

Preferred compounds of formula I include compounds of formula I-1:

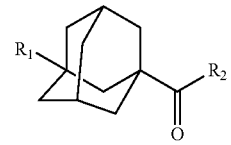

(I-1)

and pharmaceutically acceptable salts thereof, wherein:

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl; and $R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —NH-aryl, -alkenyl-heteroaryl, -heteroaryl, —NH-alkyl, —NH-cycloalkyl, or -alkenyl-heteroaryl-aryl, wherein the alkyl and ring portion of each of the above $R_1$, and $R_2$ groups is optionally substituted with up to 5 groups that are independently ($C_1$-$C_6$) alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2H$, —SH, —S-alkyl, —SOR'R", —$SO_2$R', —$NO_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, $NH_2$.

Preferred compounds of the formula I include those of formula II:

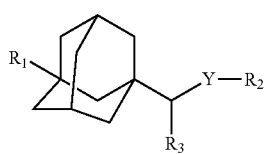

and pharmaceutically acceptable salts thereof, wherein:

Y is —C($R_4$,$R_5$)—, —N($R_4$)—, —O—, or —C(O)—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

$R_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocloalkyl, acyl, aroyl, halogen, haloalkyl, alkoxy, haloalkoxy, hydroxyalkyl, alkanoyl, oxo (=O), —COOH, —OH, —SH, —S-alkyl, —CN, —$NO_2$, —$NH_2$, —$CO_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

wherein the alkyl and ring portion of each of the above $R_1$, $R_2$, and $R_3$ groups is optionally substituted with up to 5 groups that are independently ($C_1$-$C_6$) alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2H$, —SH, —S-alkyl, —SOR'R", —$SO_2$R', —$NO_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, $NH_2$; and $R_4$ and $R_5$ are independently H or alkyl.

More preferred compounds of the formula II include those wherein:

Y is —C($R_4$,$R_5$)— or —N($R_4$)—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

wherein the alkyl and ring portion of each of the above $R_1$ and $R_2$ groups is optionally substituted with up to 5 groups that are independently ($C_1$-$C_6$) alkyl, halogen, haloalkyl, —OC(O)($C_1$-$C_6$ alkyl), —C(O)O($C_1$-$C_6$ alkyl), —CONR$_4$R$_5$, —OC(O)NR$_4$R$_5$, —NR$_4$C(O)R$_5$, —$CF_3$; —$OCF_3$, —OH, $C_1$-$C_6$ alkoxy, hydroxyalkyl, —CN, —$CO_2H$, —SH, —S-alkyl, —SOR$_4$R$_5$, —$SO_2$R$_4$R$_5$; —$NO_2$, or NR$_4$R$_5$, and wherein each alkyl portion of a substituent is optionally further substituted with 1, 2, or 3 groups independently selected from halogen, CN, OH, $NH_2$;

$R_3$ is H, alkyl, or oxo (=O); and $R_4$ and $R_5$ are independently H or ($C_1$-$C_6$)alkyl.

More preferred compounds of the formula II include those wherein Y is —NH—.

Preferred compounds of formula II include those wherein $R_3$ is oxo.

Preferred compounds of formula II include those wherein $R_3$ is methyl.

Preferred compounds of formula II also include those wherein $R_1$ is H.

Preferred compounds of formula II further include those wherein $R_1$ is optionally substituted aryl. Preferably, the aryl is phenyl, either unsubstituted or substituted with 1 or 2 halogen groups. Preferably, halogen is chloro or fluoro.

Preferred compounds of formula II also include compounds wherein $R_2$ is alkyl or cycloalkyl.

Preferred compounds of formula II also include compounds wherein $R_2$ is aryl or -alkylaryl. Preferred aryl in either group is phenyl. Preferred alkyl in alkylaryl is $C_1$-$C_3$ alkyl, either straight chain or branched. The aryl groups may be unsubstituted or substituted. Preferred substituents include 1, 2, 3, 4, or 5 (preferably 1 or 2) groups independently chosen from halogen, hydroxy, alkyl, cyanoalkyl, aminoalkyl, thioalkoxy, trifluoromethyl, haloalkoxy, aryloxy, and alkoxy.

Preferred compounds of formula II also include compounds wherein $R_2$ is heterocycloalkyl or -alkyl-heterocycloalkyl. Preferred heterocycloalkyl in either group is piperidinyl, piperazinyl, pyrrolidinyl, and morpholinyl. The heterocycloalkyl groups may be unsubstituted or substituted. Preferred substituents include 1, 2, 3, 4, or 5 (preferably 1 or 2) groups independently chosen from halogen, hydroxy, alkyl, cyanoalkyl, aminoalkyl, thioalkoxy, trifluoromethyl, haloalkoxy, aryloxy, oxo, and alkoxy.

Preferred compounds of formula II also include compounds wherein $R_2$ is heteroaryl or -alkyl-heteroaryl. Preferred heteroaryl in either group is pyridinyl, imidazolyl, indolyl, carbazolyl, thiazolyl, benzothiazolyl, benzooxazolyl, purinyl, and thienyl. The heteroaryl groups may be unsubstituted or substituted. Preferred substituents include 1, 2, 3, 4, or 5 (preferably 1 or 2) groups independently chosen from halogen, hydroxy, alkyl, cyanoalkyl, aminoalkyl, thioalkoxy, trifluoromethyl, haloalkoxy, aryloxy, and alkoxy.

The invention also provides methods for treating a patient who has, or in preventing a patient from getting, a disease or condition selected from the group consisting of a hyperproliferative disease, an inflammatory disease, or an angiogenic disease, which includes administration of a therapeutically effective amount of a compound of formula I or a pharmaceutically acceptable salt thereof, or administration of a therapeutically effective amount of a compound of formula II or a pharmaceutically acceptable salt thereof, to a patient in need of such treatment or prevention.

One preferred hyperproliferative disease which the compounds of the invention are useful in treating or preventing is cancer, including as non-limiting examples thereof solid tumors such as head and neck cancers, lung cancers, gastrointestinal tract cancers, breast cancers, gynecologic cancers, testicular cancers, urinary tract cancers, neurological cancers, endocrine cancers, skin cancers, sarcomas, mediastinal cancers, retroperitoneal cancers, cardiovascular cancers, mastocytosis, carcinosarcomas, cylindroma, dental cancers, esthesioneuroblastoma, urachal cancer, Merkel cell carcinoma and paragangliomas, and hematopoietic cancers such as Hodgkin lymphoma, non-Hodgkin lymphoma, chronic leukemias, acute leukemias, myeloproliferative cancers, plasma cell dyscrasias, and myelodysplastic syndromes. The foregoing list is by way of example, and is not intended to be exhaustive or limiting.

Other preferred diseases which can be treated or prevented with the compounds of the invention include inflammatory diseases, such as inter alia inflammatory bowel disease, arthritis, atherosclerosis, asthma, allergy, inflammatory kidney disease, circulatory shock, multiple sclerosis, chronic obstructive pulmonary disease, skin inflammation, periodontal disease, psoriasis and T cell-mediated diseases of immunity, including allergic encephalomyelitis, allergic neuritis, transplant allograft rejection, graft versus host disease, myocarditis, thyroiditis, nephritis, systemic lupus erythematosus, and insulin-dependent diabetes mellitus.

Other preferred diseases which can be treated or prevented with the compounds of the invention include angiogenic diseases, such as diabetic retinopathy, arthritis, psoriasis, Kaposi's sarcoma, hemangiomas, myocardial angiogenesis, atherscelortic plaque neovascularization, and ocular angiogenic diseases such as choroidal neovascularization, retinopathy of prematurity (retrolental fibroplasias), macular degeneration, corneal graft rejection, rubeosis, neuroscular glacoma and Oster Webber syndrome.

The invention further provides a process for preparing sphingosine kinase inhibitors. In one embodiment, the process comprises contacting a precursor compound having the formula:

with a compound having the formula: $H_2N-R_2$ under conditions sufficient to produce compounds having the formula:

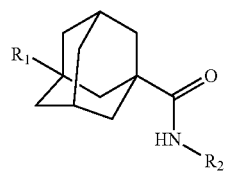

wherein:
$R_1$ and $R_2$ are as defined above.

The process further comprises reducing an adamantlyamide, as shown above, to an adamantylamine by contact with $Zn(BH_4)_2$.

In another embodiment, the process for the preparation of sphingosine kinase inhibitors comprises contacting a precursor compound having the formula:

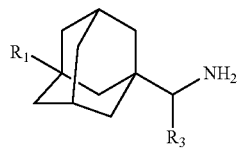

with a compound having the formula: $R_2$—Br or $R_2C(O)Cl$ under conditions sufficient to produce compounds having the formula:

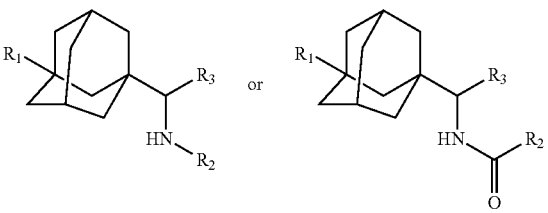

wherein:
$R_1$, $R_2$ and $R_3$ are as defined earlier.

In a further embodiment, the process comprises contacting a precursor compound having the formula:

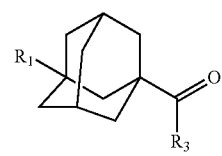

with a compound having the formula: $H_2N-R_2$ or $R_2C(O)H$ under conditions sufficient to produce compounds having the formula:

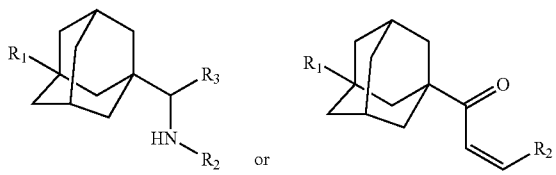

wherein:

$R_1$, $R_2$ and $R_3$ are as defined earlier.

The invention also provides pharmaceutical compositions that include a compound of formula I or a pharmaceutically acceptable salt thereof, or a compound of formula II or a pharmaceutically acceptable salt thereof, as active ingredient, in combination with a pharmaceutically acceptable carrier, medium, or auxiliary agent.

The pharmaceutical compositions of the present invention may be prepared in various forms for administration, including tablets, caplets, pills or dragees, or can be filled in suitable containers, such as capsules, or, in the case of suspensions, filled into bottles. As used herein "pharmaceutically acceptable carrier medium" includes any and all solvents, diluents, or other liquid vehicle; dispersion or suspension aids; surface active agents; preservatives; solid binders; lubricants and the like, as suited to the particular dosage form desired. Various vehicles and carriers used in formulating pharmaceutical compositions and known techniques for the preparation thereof are disclosed in Remington's Pharmaceutical Sciences (Osol et al. eds., 15th ed., Mack Publishing Co.: Easton, Pa., 1975). Except insofar as any conventional carrier medium is incompatible with the chemical compounds of the present invention, such as by producing any undesirable biological effect or otherwise interacting in a deleterious manner with any other component of the pharmaceutical composition, the use of the carrier medium is contemplated to be within the scope of this invention.

In the pharmaceutical compositions of the present invention, the active agent may be present in an amount of at least 1% and not more than 99% by weight, based on the total weight of the composition, including carrier medium or auxiliary agents. Preferably, the proportion of active agent varies between 1% to 70% by weight of the composition. Pharmaceutical organic or inorganic solid or liquid carrier media suitable for enteral or parenteral administration can be used to make up the composition. Gelatin, lactose, starch, magnesium, stearate, talc, vegetable and animal fats and oils, gum polyalkylene glycol, or other known excipients or diluents for medicaments may all be suitable as carrier media.

The pharmaceutical compositions of the present invention may be administered using any amount and any route of administration effective for treating a patient who has, or in preventing a patient from getting, a disease or condition selected from the group consisting of a hyperproliferative disease, an inflammatory disease, and an angiogenic disease. Thus the expression "therapeutically effective amount," as used herein, refers to a sufficient amount of the active agent to provide the desired effect against target cells. The exact amount required will vary from subject to subject, depending on the species, age, and general condition of the subject; the particular SK inhibitor; its mode of administration; and the like.

The pharmaceutical compounds of the present invention are preferably formulated in unit dosage form for ease of administration and uniformity of dosage. "Unit dosage form," as used herein, refers to a physically discrete unit of therapeutic agent appropriate for the animal to be treated. Each dosage should contain the quantity of active material calculated to produce the desired therapeutic effect either as such, or in association with the selected pharmaceutical carrier medium. Typically, the pharmaceutical composition will be administered in dosage units containing from about 0.1 mg to about 10,000 mg of the agent, with a range of about 1 mg to about 1000 mg being preferred.

The pharmaceutical compositions of the present invention may be administered orally or parentally, such as by intramuscular injection, intraperitoneal injection, or intravenous infusion. The pharmaceutical compositions may be administered orally or parenterally at dosage levels of about 0.1 to about 1000 mg/kg, and preferably from about 1 to about 100 mg/kg, of animal body weight per day, one or more times a day, to obtain the desired therapeutic effect.

Although the pharmaceutical compositions of the present invention can be administered to any subject that can benefit from the therapeutic effects of the compositions, the compositions are intended particularly for the treatment of diseases in humans.

The pharmaceutical compositions of the present invention will typically be administered from 1 to 4 times a day, so as to deliver the daily dosage as described herein. Alternatively, dosages within these ranges can be administered by constant infusion over an extended period of time, usually 1 to 96 hours, until the desired therapeutic benefits have been obtained. However, the exact regimen for administration of the chemical compounds and pharmaceutical compositions described herein will necessarily be dependent on the needs of the animal being treated, the type of treatments being administered, and the judgment of the attending physician.

In certain situations, the compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

Non-toxic pharmaceutically acceptable salts of the compounds of the present invention include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of the present invention.

The invention also encompasses prodrugs of the compounds of the present invention. Those skilled in the art will recognize various synthetic methodologies, which may be employed to prepare non-toxic pharmaceutically acceptable addition salts and prodrugs of the compounds encompassed by the present invention.

The invention provides compounds of formula I and II which are inhibitors of SK, and which are useful for modulating the sphingomyelin signal transduction pathway, and in treating and preventing hyperproliferative diseases, inflammatory diseases, and angiogenic diseases. The compounds of the invention can be prepared by one skilled in the art based only on knowledge of the compound's chemical structure. The chemistry for the preparation of the compounds of this invention is known to those skilled in the art. In fact, there is more than one process to prepare the compounds of the invention. Specific examples of methods of preparation can be found herein and in the art.

As discussed above, sphingolipids are critically important in regulating the balance between cell proliferation and apoptosis. Sphingosine-1-phosphate is produced by the enzyme SK and stimulates the proliferation of tumor cells. Concurrent depletion of ceramide by the action of SK blocks apoptosis. The compounds of the invention are inhibitors of human SK. Therefore, inhibition of SK activity according to the invention will attenuate tumor cell proliferation and promote apoptosis. Therefore, the compounds of the invention are useful as anticancer agents. Furthermore, since cell hyperproliferation is a required process in the development of atherosclerosis and psoriasis, the compounds of the invention, which are SK inhibitors, are useful in the treatment of these, and other, hyperproliferative diseases. Additionally, inappropriate activation and/or proliferation of specific classes of lymphocytes results in chronic inflammatory and autoimmune diseases. Consequently, compounds of the invention are also useful in the treatment of these diseases. Additionally, inappropriate angiogenesis results in a variety of diseases, as described below. Consequently, compounds of the invention are also useful in the treatment of these diseases.

DEFINITIONS

The definitions and explanations below are for the terms as used throughout this entire document, including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The symbol "—" in general represents a bond between two atoms in the chain. Thus $CH_3$—O—$CH_2$—$CH(R_i)$—$CH_3$ represents a 2-substituted-1-methoxypropane compound. In addition, the symbol "—" represents the point of attachment of the substituent to a compound. Thus for example aryl($C_1$-$C_6$)alkyl- indicates an alkylaryl group, such as benzyl, attached to the compound at the alkyl moiety.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

The phrase "optionally substituted" is used interchangeably with the phrase "substituted or unsubstituted". Unless otherwise indicated, an optionally substituted group may have a substituent at each substitutable position of the group, and each substituent is independent of the other.

As used herein, the terms "halogen" or "halo" indicate fluorine, chlorine, bromine, or iodine.

The term "heteroatom" means nitrogen, oxygen or sulfur and includes any oxidized form of nitrogen and sulfur, and the quaternized form of any basic nitrogen. Also the term "nitrogen" includes a substitutable nitrogen in a heterocyclic ring. As an example, in a saturated or partially unsaturated ring having 0-3 heteroatoms selected from nitrogen, oxygen or sulfur, the nitrogen may be N (as in 3,4-dihydro-2H-pyrrolyl), NH (as in pyrrolidinyl) or $NR^+$ (as in N-substituted pyrrolidinyl).

The term "alkyl", as used herein alone or as part of a larger moiety, refers to a saturated aliphatic hydrocarbon including straight chain, branched chain or cyclic (also called "cycloalkyl") groups. Examples of alkyl groups include methyl, ethyl, propyl, isopropyl, butyl, iso-, sec- and tert-butyl, pentyl, hexyl, heptyl, 3-ethylbutyl, and the like. Preferably, the alkyl group has 1 to 20 carbon atoms (whenever a numerical range, e.g. "1-20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The cycloalkyl can be monocyclic, or a polycyclic fused system. Examples of cycloalkyl groups include cyclopropyl, cyclobutyl, cyclopentyl, cyclohexyl, cycloheptyl, cyclooctyl, and adamantyl. The alkyl or cycloalkyl group may be unsubstituted or substituted with 1, 2, 3 or more substituents. Examples of such substituents including, without limitation, halo, hydroxy, amino, alkoxy, alkylamino, dialkylamino, cycloalkyl, aryl, aryloxy, arylalkyloxy, heterocyclic radical, and (heterocyclic radical) oxy. Examples include fluoromethyl, hydroxyethyl, 2,3-dihydroxyethyl, (2- or 3-furanyl)methyl, cyclopropylmethyl, benzyloxyethyl, (3-pyridinyl)methyl, (2-thienyl)ethyl, hyroxypropyl, aminocyclohexyl, 2-dimethylaminobutyl, methoxymethyl, N-pyridinylethyl, and diethylaminoethyl.

The term "cycloalkylalkyl", as used herein alone or as part of a larger moiety, refers to a $C_3$-$C_{10}$ cycloalkyl group attached to the parent molecular moiety through an alkyl group, as defined above. Examples of cycloalkylalkyl groups include cyclopropylmethyl and cyclopentylethyl.

The term "alkenyl", as used herein alone or as part of a larger moiety, refers to an aliphatic hydrocarbon having at least one carbon-carbon double bond, including straight chain, branched chain or cyclic groups having at least one carbon-carbon double bond. Preferably, the alkenyl group has 2 to 20 carbon atoms. More preferably, it is a medium size alkenyl having 2 to 10 carbon atoms. Most preferably, it is a lower alkenyl having 2 to 6 carbon atoms. The alkenyl group may be unsubstituted or substituted with 1, 2, 3 or more substituents. Examples of such substituents including, without limitation halo, hydroxy, amino, alkoxy, alkylamino, dialkylamino, cycloalkyl, aryl, aryloxy, arylalkyloxy, heterocyclic radical, and (heterocyclic radical)oxy. Depending on the placement of the double bond and substituents, if any, the geometry of the double bond may be entgegen (E) or zusammen (Z), cis, or trans. Examples of alkenyl groups include ethenyl, propenyl, cis-2-butenyl, trans-2-butenyl, and 2-hydroxy-2-propenyl.

The term "alkynyl", as used herein alone or as part of a larger moiety, refers to an aliphatic hydrocarbon having at least one carbon-carbon triple bond, including straight chain, branched chain or cyclic groups having at least one carbon-carbon triple bond. Preferably, the alkynyl group has 2 to 20 carbon atoms. More preferably, it is a medium size alkynyl having 2 to 10 carbon atoms. Most preferably, it is a lower alkynyl having 2 to 6 carbon atoms. The alkynyl group may be unsubstituted or substituted with 1, 2, 3 or more substituents. Examples of such substituents including, without limitation, halo, hydroxy, amino, alkoxy, alkylamino, dialkylamino, cycloalkyl, aryl, aryloxy, arylalkyloxy, heterocyclic radical, and (heterocyclic radical)oxy. Examples of alkynyl groups include ethynyl, propynyl, 2-butynyl, and 2-hydroxy-3-butylnyl.

The term "alkoxy", as used herein alone or as part of a larger moiety, represents an alkyl group of indicated number of carbon atoms attached to the parent molecular moiety through an oxygen bridge. Examples of alkoxy groups include, for example, methoxy, ethoxy, propoxy and isopropoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, and fluoroethoxy.

The term "aryl", as used herein alone or as part of a larger moiety, refers to an aromatic hydrocarbon ring system containing at least one aromatic ring. The aromatic ring may optionally be fused or otherwise attached to other aromatic hydrocarbon rings or non-aromatic hydrocarbon rings. Additionally, the aryl group may be substituted or unsubstituted by various groups such as hydrogen, halo, hydroxy, alkyl, haloalkyl, alkoxy, nitro, cyano, alkylamine, carboxy or alkoxycarbonyl. Examples of aryl groups include, for example, phenyl, naphthyl, 1,2,3,4-tetrahydronaphthalene, benzodioxole, and biphenyl. Preferred examples of unsubstituted aryl groups include phenyl and biphenyl. Preferred aryl group substituents include hydrogen, halo, alkyl, haloalkyl, hydroxy and alkoxy.

The term "heteroalkyl", as used herein alone or as part of a larger moiety, refers to an alkyl radical as defined herein with one or more heteroatoms replacing a carbon atom with the moiety. Such heteroalkyl groups are alternately referred to using the terms ether, thioether, amine, and the like.

The term "heterocyclyl", as used herein alone or as part of a larger moiety, refers to saturated, partially unsaturated and unsaturated heteroatom-containing ring shaped radicals, where the heteroatoms may be selected from nitrogen, sulfur and oxygen. Said heterocyclyl groups may be unsubstituted or substituted at one or more atoms within the ring system. The heterocyclic ring may contain one or more oxo groups.

The term "heterocycloalkyl", as used herein alone or as part of a larger moiety, refers to a non-aromatic ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred monocyclic heterocycloalkyl groups include piperidyl, piperazinyl, morpholinyl, pyrrolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Heterocycloalkyl radicals may also be partially unsaturated. Examples of such groups include dihydrothienyl, dihydropyranyl, dihydrofuryl, and dihydrothiazolyl.

The term "heteroaryl", as used herein alone or as part of a larger moiety, refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Additionally, the heteroaryl group may be unsubstituted or substituted at one or more atoms of the ring system, or may contain one or more oxo groups. Examples of heteroaryl groups include, for example, pyridine, furan, thiophene, carbazole and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, benzopyrazolyl, purinyl, benzooxazolyl, and carbazolyl.

The term "acyl" means an H—C(O)— or alkyl-C(O)— group in which the alkyl group, straight chain, branched or cyclic, is as previously described. Exemplary acyl groups include formyl, acetyl, propanoyl, 2-methylpropanoyl, butanoyl, and caproyl.

The term "aroyl" means an aryl-C(O)— group in which the aryl group is as previously described. Exemplary aroyl groups include benzoyl and 1- and 2-naphthoyl.

The term "solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Exemplary solvates include ethanolates, methanolates, and the like. "Hydrate" is a solvate wherein the solvent molecule(s) is/are $H_2O$.

Compounds that have the same molecular formula but differ in the nature or sequence of bonding of their atoms or arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, a carbon atom that is bonded to four different groups, a pair of enantiomers is possible. An enantiomer can be characterized by the absolute configuration of its asymmetric center and is described by the R- and S-sequencing rules of Cahn and Prelog, which are well known to those in the art. Additionally, entiomers can be characterized by the manner in which a solution of the compound rotates a plane of polarized light and designated as dextrorotatory or levorotatory (i.e. as (+) or (−) isomers respectively). A chiral compound can exist as either individual enantiomer or as a mixture thereof A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless otherwise indicated, the specification and claims is intended to include both individual enantiomers as well as mixtures, racemic or otherwise, thereof.

Certain compounds of this invention may exhibit the phenomena of tautomerism and/or structural isomerism. For example, certain compounds described herein may adopt an E or a Z configuration about a carbon-carbon double bond or they may be a mixture of E and Z. This invention encompasses any tautomeric or structural isomeric form and mixtures thereof.

Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biologic assays.

As used herein, "SK-related disorder", "SK-driven disorder", and "abnormal SK activity" all refer to a condition characterized by inappropriate, i.e., under or, more commonly, over, SK catalytic activity. Inappropriate catalytic activity can arise as the result of either: (1) SK expression in cells that normally do not express SK, (2) increased SK catalytic activity leading to unwanted cellular process, such as, without limitation, cell proliferation, gene regulation, resistance to apoptosis, and/or differentiation. Such changes in SK expression may occur by increased expression of SK and/or mutation of SK such that its catalytic activity is enhanced, (3) decreased SK catalytic activity leading to unwanted reductions in cellular processes. Some examples of SK-related disorders, without limitation, are described elsewhere in this application.

The term "method" refers to manners, means, techniques and procedures for accomplishing a given task including, but not limited to, those manners, means, techniques and procedures either known to, or readily developed from known manners, means, techniques and procedures by practitioners of the chemical, pharmaceutical, biological, biochemical and medical arts.

The term "modulation" or "modulating" refers to the alteration of the catalytic activity of SK. In particular, modulating refers to the activation or, preferably, inhibition of SK catalytic activity, depending on the concentration of the compound or salt to which SK is exposed.

The term "catalytic activity" as used herein refers to the rate of phosphorylation of sphingosine under the influence of SK.

The term "contacting" as used herein refers to bringing a compound of this invention and SK together in such a manner that the compound can affect the catalytic activity of SK, either directly, i.e., by interacting with SK itself, or indirectly, i.e., by altering the intracellular localization of SK. Such "contacting" can be accomplished in vitro, i.e. in a test tube, a Petri dish or the like. In a test tube, contacting may involve only a compound and SK or it may involve whole cells. Cells may also be maintained or grown in cell culture dishes and contacted with a compound in that environment. In this context, the ability of a particular compound to affect an SK-related disorder can be determined before the use of the compounds in vivo with more complex living organisms is attempted. For cells outside the organism, multiple methods exist, and are well-known to those skilled in the art, to allow contact of the compounds with SK including, but not limited to, direct cell microinjection and numerous techniques for promoting the movement of compounds across a biological membrane.

The term "in vitro" as used herein refers to procedures performed in an artificial environment, such as for example, without limitation, in a test tube or cell culture system. The skilled artisan will understand that, for example, an isolate SK enzyme may be contacted with a modulator in an in vitro environment. Alternatively, an isolated cell may be contacted with a modulator in an in vitro environment.

The term "in vivo" as used herein refers to procedures performed within a living organism such as, without limitation, a human, mouse, rat, rabbit, bovine, equine, porcine, canine, feline, or primate.

The term "IC$_{50}$" or "50% inhibitory concentration" as used herein refers to the concentration of a compound that reduces a biological process by 50%. These processes can include, but are not limited to, enzymatic reactions, i.e. inhibition of SK catalytic activity, or cellular properties, i.e. cell proliferation, apoptosis or cellular production of S1P.

As used herein, "administer" or "administration" refers to the delivery of a compound or salt of the present invention or of a pharmaceutical composition containing a compound or salt of this invention to an organism for the purpose of prevention or treatment of an SK-related disorder.

As used herein, the terms "prevent", "preventing" and "prevention" refer to a method for barring an organism from acquiring an SK-related disorder.

As used herein, the terms "treat", "treating" and "treatment" refer to a method of alleviating or abrogating an SK-mediated disorder and/or its attendant symptoms.

The term "organism" refers to any living entity comprised of at least one cell. A living organism can be as simple as, for example, a single eukaryotic cell or as complex as a mammal. In a preferred aspect of this invention, the organism is a mammal. In a particularly preferred aspect of this invention, the mammal is a human being.

A "pharmaceutical composition" refers to a mixture of one or more of the compounds described herein, or pharmaceutically acceptable salts thereof, with other chemical components, such as physiologically acceptable carriers and excipients. The purpose of a pharmaceutical composition is to facilitate administration of a compound to an organism.

The term "pharmaceutically acceptable salt" refers to those salts that retain the biological effectiveness of the parent compound. Such salts include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid, or malonic acid and the like, preferably hydrochloric acid or (L)-malic acid; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, tromethamine, N-methylglucamine, and the like.

As used herein, the term a "physiologically acceptable carrier" refers to a carrier or diluent that does not cause significant irritation to an organism and does not abrogate the biological activity and properties of the administered compound. Typically, this includes those properties and/or substances that are acceptable to the patient from a pharmacological/toxicological point of view and to the manufacturing pharmaceutical chemist from a physical/chemical point of view regarding composition, formulation, stability, patient acceptance and bioavailability.

An "excipient" refers to an inert substance added to a pharmaceutical composition to further facilitate administration of a compound. Example, without limitations, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

The term "therapeutically effective amount" as used herein refers to that amount of the compound being administered that is effective to reduce or lessen at least one symptom of the disease being treated or to reduce or delay onset of one or more clinical markers or symptoms of the disease. In reference to the treatment of cancer, a therapeutically effective amount refers to that amount that has the effect of: (1) reducing the size of the tumor, (2) inhibiting, i.e. slowing to some extent, preferably stopping, tumor metastasis, (3) inhibiting, i.e. slowing to some extent, preferably stopping, tumor growth, and/or (4) relieving to some extent, preferably eliminating, one or more symptoms associated with the cancer.

The compounds of this invention may also act as a prodrug. The term "prodrug" refers to an agent which is converted into the parent drug in vivo. Prodrugs are often useful because, in some situations, they may be easier to administer than the parent drug. They may, for example, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug"), carbamate or urea.

The compounds of this invention may also be metabolized by enzymes in the body of the organism, such as a human being, to generate a metabolite that can modulate the activity of SK. Such metabolites are within the scope of the present invention.

Indications

Sphingosine kinase (SK), whose catalytic activity is modulated by the compounds and compositions of this invention, is a key enzyme involved in signaling pathways that are abnormally activated in a variety of diseases. The following discussion outlines the roles of SK in hyperproliferative, inflammatory and angiogenic diseases, and consequently provides examples of uses of the compounds and compositions of this invention. The use of these compounds and compositions for the prevention and/or treatment of additional diseases in which SK is abnormally activated are also within the scope of the present invention.

Hyperproliferative Diseases.

The present invention relates to compounds, pharmaceutical compositions and methods useful for the treatment and/or prevention of hyperproliferative diseases. More specifically, the invention relates to compounds and pharmaceutical compositions that inhibit the enzymatic activity of SK for the treatment and/or prevention of hyperproliferative diseases, such as cancer, psoriasis, mesangial cell proliferative disorders, atherosclerosis and restenosis. The following discussion demonstrates the role of SK in several of these hyperproliferative diseases. Since the same processes are involved in the above listed diseases, the compounds, pharmaceutical compositions and methods of this invention will be useful for the treatment and/or prevention of a variety of diseases.

Sphingosine-1-phosphate and ceramide have opposing effects on cancer cell proliferation and apoptosis. Sphingomyelin is not only a building block for cellular membranes but also serves as the precursor for potent lipid messengers that have profound cellular effects. Stimulus-induced metabolism of these lipids is critically involved in cancer cell biology. Consequently, these metabolic pathways offer exciting targets for the development of anticancer drugs.

Ceramide is produced by the hydrolysis of sphingomyelin in response to growth factors or other stimuli. Ceramide induces apoptosis in tumor cells, but can be further hydrolyzed by the action of ceramidase to produce sphingosine. Sphingosine is then rapidly phosphorylated by SK to produce S1P, which is a critical second messenger that exerts proliferative and antiapoptotic actions. For example, microinjection of S1P into mouse oocytes induces DNA synthesis. Additionally, S1P effectively inhibits ceramide-induced apoptosis in association with decreased caspase activation. Furthermore, ceramide enhances apoptosis in response to anticancer drugs including Taxol and etoposide. These studies in various cell lines consistently indicate that S1P is able to induce proliferation and protect cells from ceramide-induced apoptosis.

A critical balance, which may be termed a ceramide/S1P rheostat, has been hypothesized to determine the fate of the cell. In this model, the balance between the cellular concentrations of ceramide and S1P determines whether a cell proliferates or undergoes apoptosis. Upon exposure to mitogens or intracellular oncoproteins, the cells experience a rapid increase in the intracellular levels of S1P and depletion of ceramide levels. This situation promotes cell survival and proliferation. In contrast, activation of sphingomyelinase in the absence of activation of ceramidase and/or SK results in the accumulation of ceramide and subsequent apoptosis.

SK is the enzyme responsible for S1P production in cells. RNA encoding SK is detected in most tissues. A variety of proliferative factors, including PKC activators, fetal calf serum and platelet-derived growth factor (Olivera et al., 1993, *Nature* 365: 557), EGF, and TNFα (Dressler et al., 1992, *Science* 255: 1715) rapidly elevate cellular SK activity. SK activity is increased by phosphorylation of the enzyme by ERK (Pitson et al., 2003, *EMBO J.* 22: 5491), while S1P promotes signaling through the Ras-Raf-Mek-Erk pathway, setting up an amplification cascade for cell proliferation.

Sphingosine kinase and S1P play important roles in cancer pathogenesis. An oncogenic role of SK has been demonstrated. In these studies, transfection of SK into NIH/3T3 fibroblasts was sufficient to promote foci formation and cell growth in soft-agar, and to allow these cells to form tumors in NOD/SCID mice (Xia et al., 2000, *Curr Biol* 10: 1527). Additionally, inhibition of SK by transfection with a dominant-negative SK mutant or by treatment of cells with the nonspecific SK inhibitor DMS blocked transformation mediated by oncogenic H-Ras. As abnormal activation of Ras frequently occurs in cancer, these findings suggest a significant role of SK in this disease. SK has also been linked to estrogen signaling and estrogen-dependent tumorigenesis in MCF-7 cells (Nava et al., 2002, *Exp Cell Res* 281: 115). Other pathways or targets to which SK activity has been linked in hyperproliferative diseases include VEGF signaling via the Ras and MAP kinase pathway (Shu et al., 2002, *Mol Cell Biol* 22: 7758), protein kinase C (Nakade et al., 2003, *Biochim Biophys Acta* 1635: 104), TNFα (Vann et al., 2002, *J Biol Chem* 277: 12649), hepatocyte nuclear factor-1 and retinoic acid receptor alpha, intracellular calcium and caspase activation. While the elucidation of downstream targets of S1P remains an interesting problem in cell biology, sufficient validation of these pathways has been established to justify the development of SK inhibitors as new types of antiproliferative drugs.

Cellular hyperproliferation is a characteristic of a variety of diseases, including, without limitation, cancer, psoriasis, mesangial cell proliferative disorders, atherosclerosis and restenosis. Therefore, the compounds, pharmaceutical compositions and methods of this invention will be useful for the prevention and/or treatment of cancer, including solid tumors, hematopoietic cancers and tumor metastases. Such cancers may include, without limitation, solid tumors such as head and neck cancers, lung cancers, gastrointestinal tract cancers, breast cancers, gynecologic cancers, testicular cancers, urinary tract cancers, neurological cancers, endocrine cancers, skin cancers, sarcomas, mediastinal cancers, retroperitoneal cancers, cardiovascular cancers, mastocytosis, carcinosarcomas, cylindroma, dental cancers, esthesioneuroblastoma, urachal cancer, Merkel cell carcinoma and paragangliomas. Additionally, such cancers may include, without limitation, hematopoietic cancers such as Hodgkin lymphoma, non-Hodgkin lymphoma, chronic leukemias, acute leukemias, myeloproliferative cancers, plasma cell dyscrasias, and myelodysplastic syndromes.

Psoriasis is a common chronic disfiguring skin disease that is characterized by well-demarcated, red, hardened and scaly plaques that may be limited or widespread. While the disease is rarely fatal, it has serious detrimental effects on the quality of life of the patient, and this is further complicated by the lack of effective therapies. There is therefore a large unmet need for effective and safe drugs for this condition. Psoriasis is characterized by local keratinocyte hyperproliferation, T cell-mediated inflammation and by localized angiogenesis. Abnormal activation of SK has been implicated in all of these processes. Therefore, SK inhibitors are expected to be of use in the therapy of psoriasis.

Mesangial cell hyperproliferative disorders refer to disorders brought about by the abnormal hyperproliferation of mesangial cells in the kidney. Mesangial hyperproliferative disorders include various human renal diseases such as glomerulonephritis, diabetic nephropathy, and malignant nephrosclerosis, as well as such disorders such as thrombotic microangiopathy syndromes, transplant rejection, and glomerulopathies. As the hyperproliferation of mesangial cells is induced by growth factors whose action is dependent on increased signaling through SK, the SK inhibitory compounds, pharmaceutical compositions and methods of this invention are expected to be of use in the therapy of these mesangial cell hyperproliferative disorders.

In addition to inflammatory processes discussed below, atherosclerosis and restenosis are characterized by hyperproliferation of vascular smooth muscle cells at the sites of the lesions. As the hyperproliferation of vascular smooth muscle cells is induced by growth factors whose action is dependent of increased signaling through SK, the SK inhibitory compounds, pharmaceutical compositions and methods of this invention are expected to be of use in the therapy of these vascular disorders.

Inflammatory Diseases.

The present invention also relates to compounds, pharmaceutical compositions and methods useful for the treatment and/or prevention of inflammatory diseases. More specifically, the invention relates to compounds and pharmaceutical compositions that inhibit the enzymatic activity of SK for the treatment and/or prevention of inflammatory diseases, such as inflammatory bowel disease, arthritis, atherosclerosis, asthma, allergy, inflammatory kidney disease, circulatory shock, multiple sclerosis, chronic obstructive pulmonary disease, skin inflammation, periodontal disease, psoriasis and T cell-mediated diseases of immunity, including allergic encephalomyelitis, allergic neuritis, transplant allograft rejection, graft versus host disease, myocarditis, thyroiditis, nephritis, systemic lupus erythematosus, and insulin-dependent diabetes mellitus. The following discussion demonstrates the role of SK in several of these inflammatory diseases. Since the same processes are involved in the above listed diseases, the compounds, pharmaceutical compositions and methods of this invention will be useful for the treatment and/or prevention of a variety of diseases.

Inflammatory bowel disease (IBD) encompasses a group of disorders characterized by pathological inflammation of the lower intestine. Crohn's disease and ulcerative colitis are the best-known forms of IBD, and both fall into the category of "idiopathic" IBD because their etiologies remain to be elucidated, although proposed mechanisms implicate infectious and immunologic mediators. Studies on the etiology and therapy of IBD have been greatly facilitated by the development of several animal models that mimic the clinical and immunopathological disorders seen in humans. From studies with these models, it is clear that the full manifestations of IBD are dependent on synergy between the humoral and cellular immune responses. The notion that immune cells and cytokines play critical roles in the pathogenesis of IBD is well established; however, the molecular mechanisms by which this occurs are not yet clearly defined. As discussed below, cytokines that promote inflammation in the intestine afflicted with IBD, all activate a common mediator, sphingosine kinase (SK). Most prominently, tumor necrosis factor-$\alpha$ (TNF$\alpha$) has been shown to play a significant role in IBD, such that antibody therapy directed against this cytokine, i.e. Remicade, may be a promising treatment. TNF$\alpha$ activates several processes shown to contribute to IBD and is necessary for both the initiation and persistence of the Th1 response. For example, TNF$\alpha$ has been shown act through the induction of nuclear factor kappa B (NF$\kappa$B) which has been implicated in increasing the proinflammatory enzymes nitric oxide synthase (NOS) and cyclooxygenase-2 (COX-2). COX-2 has been shown to play a key role in the inflammation of IBDs through its production of prostaglandins, and oxidative stress such as that mediated by nitric oxide produced by NOS has also shown to exacerbate IBD inflammation.

A common pathway of immune activation in IBDs is the local influx of mast cells, monocytes, macrophages and polymorphonuclear neutrophils which results in the secondary amplification of the inflammation process and produces the clinical manifestations of the diseases. This results in markedly increased numbers of mast cells in the mucosa of the ileum and colon of patients with IBD, which is accompanied by dramatic increases in TNF$\alpha$ (He, 2004, *World J Gastroenterology* 10 (3): 309). Additional mast cell secretory products, including histamine and tryptase, may be important in IBDs. Therefore, it is clear that inflammatory cascades play critical roles in the pathology of IBDs.

The mechanisms and effects of the sphingolipid interconversion have been the subjects of a growing body of scientific investigation. Sphingomyelin is not only a structural component of cellular membranes, but also serves as the precursor for the potent bioactive lipids ceramide and sphingosine 1-phosphate (S1P). A ceramide:S1P rheostat is thought to determine the fate of the cell, such that the relative cellular concentrations of ceramide and S1P determine whether a cell proliferates or undergoes apoptosis. Ceramide is produced by the hydrolysis of sphingomyelin in response to inflammatory stresses, including TNF$\alpha$, and can be hydrolyzed by ceramidase to produce sphingosine. Sphingosine is then rapidly phosphorylated by sphingosine kinase (SK) to produce S1P. Ceramidase and SK are also activated by cytokines and growth factors, leading to rapid increases in the intracellular levels of S1P and depletion of ceramide levels. This situation promotes cell proliferation and inhibits apoptosis. Deregulation of apoptosis in phagocytes is an important component of the chronic inflammatory state in IBDs, and S1P has been shown to protect neutrophils from apoptosis in response to Fas, TNF$\alpha$ and ceramide. Similarly, apoptosis of macrophages is blocked by S1P.

In addition to its role in regulating cell proliferation and apoptosis, S1P has been shown to have several important effects on cells that mediate immune functions. Platelets, monocytes and mast cells secrete S1P upon activation, promoting inflammatory cascades at the site of tissue damage. Activation of SK is required for the signaling responses, since the ability of TNFα to induce adhesion molecule expression via activation of NFκB is mimicked by S1P and is blocked by the SK inhibitor dimethylsphingosine (Xia et al., 1998, *Proc Natl Acad Sci USA* 95: 14196). Similarly, S1P mimics the ability of TNFα to induce the expression of COX-2 and the synthesis of $PGE_2$, and knock-down of SK by RNA interference blocks these responses to TNFα but not S1P (Pettus et al., 2003, *FASEB J* 17: 1411). S1P is also a mediator of $Ca^{2+}$ influx during neutrophil activation by TNFα and other stimuli, leading to the production of superoxide and other toxic radicals (Mackinnon, 2002, *Journal of Immunology* 169(11): 6394).

A model for the roles of sphingolipid metabolites in the pathology of IBDs involves a combination of events in the colon epithelial cells and recruited mast cells, macrophages and neutrophils. Early in the disease, immunologic reactions or other activating signals promote the release of inflammatory cytokines, particularly TNFα from macrophages and mast cells. The actions of TNFα are mediated through its activation of S1P production. For example, TNFα induces S1P production in endothelial cells (Xia et al., 1998, *Proc Natl Acad Sci USA* 95: 14196), neutrophils (Niwa et al., 2000, *Life Sci* 66: 245) and monocytes by activation of sphingomyelinase, ceramidase and SK. S1P is a central player in the pathway since it has pleiotropic actions on the mucosal epithelial cells, macrophages, mast cells and neutrophils. Within the mucosal cells, S1P activates NFκB thereby inducing the expression of adhesion molecules, COX-2 resulting in $PGE_2$ synthesis, and NOS producing nitric oxide. Together, these chemoattractants and the adhesion molecules promote neutrophil infiltration into the mucosa. At the same time, S1P activates the neutrophils resulting in the release of oxygen free radicals that further inflame and destroy epithelial tissue. Similarly, S1P promotes the activation and degranulation of mast cells.

As the processes involved in IBDs are induced by cytokines and growth factors whose action is dependent on increased signaling through SK, the SK inhibitory compounds, pharmaceutical compositions and methods of this invention are expected to be of use in the therapy of IBDs.

Rheumatoid arthritis (RA) is a chronic, systemic disease that is characterized by synovial hyperplasia, massive cellular infiltration, erosion of the cartilage and bone, and an abnormal immune response. Studies on the etiology and therapy of rheumatoid arthritis have been greatly facilitated by the development of animal models that mimic the clinical and immunopathological disorders seen in humans. From studies in these models, it is clear that the full manifestations of RA are dependent on synergy between the humoral and cellular immune responses. The notion that immune cells, especially neutrophils, and cytokines play critical roles in the pathogenesis of arthritis is well established. However, the mechanisms by which this occurs are not fully elucidated.

The early phase of rheumatic inflammation is characterized by leukocyte infiltration into tissues, especially by neutrophils. In the case of RA, this occurs primarily in joints where leukocyte infiltration results in synovitis and synovium thickening producing the typical symptoms of warmth, redness, swelling and pain. As the disease progresses, the aberrant collection of cells invade and destroy the cartilage and bone within the joint leading to deformities and chronic pain. The inflammatory cytokines TNFα, IL-1β and IL-8 act as critical mediators of this infiltration, and these cytokines are present in the synovial fluid of patients with RA.

Leukocytes localize to sites of inflammatory injury as a result of the integrated actions of adhesion molecules, cytokines, and chemotactic factors. In lipopolysaccharide-induced arthritis in the rabbit, the production of TNFα and IL-1β in the initiative phase of inflammation paralleled the time course of leukocyte infiltration. The adherence of neutrophils to the vascular endothelium is a first step in the extravasation of cells into the interstitium. This process is mediated by selectins, integrins, and endothelial adhesion molecules, e.g. ICAM-1 and VCAM-1. Since TNFα induces the expression of ICAM-1 and VCAM-1 and is present in high concentrations in arthritic joints, it is likely that this protein plays a central role in the pathogenesis of the disease. This is supported by the clinical activity of anti-TNFα therapies such as Remicade. After adherence to the endothelium, leukocytes migrate along a chemoattractant concentration gradient. A further critical process in the progression of RA is the enhancement of the blood supply to the synovium through angiogenesis. Expression of the key angiogenic factor VEGF is potently induced by pro-inflammatory cytokines including TNFα. Together, these data point to important roles of TNFα, leukocytes, leukocyte adhesion molecules, leukocyte chemoattractants and angiogenesis in the pathogenesis of arthritic injury.

Early in the disease, immunologic reactions or other activating signals promote the release of inflammatory cytokines, particularly TNFα and IL-1β from macrophages and mast cells. Ceramide is produced by the hydrolysis of sphingomyelin in response to inflammatory stresses, including TNFα and IL-1β (Dressler et al., 1992, *Science* 255: 1715). Ceramide can be further hydrolyzed by ceramidase to produce sphingosine which is then rapidly phosphorylated by SK to produce S1P. Ceramidase and SK are also activated by cytokines and growth factors, leading to rapid increases in the intracellular levels of S1P and depletion of ceramide levels. This situation promotes cell proliferation and inhibits apoptosis. Deregulation of apoptosis in phagocytes is an important component of the chronic inflammatory state in arthritis, and S1P has been shown to protect neutrophils from apoptosis in response to Fas, TNFα and ceramide. Similarly, apoptosis of macrophages is blocked by S1P.

In addition to its role in regulating cell proliferation and apoptosis, S1P is a central player in the pathway since it has pleiotropic actions on the endothelial cells, leukocytes, chondrocytes and synovial cells. Within the endothelial cells, S1P activates NFκB thereby inducing the expression of multiple adhesion molecules and COX-2 resulting in $PGE_2$ synthesis. Together, this chemoattractant and the adhesion molecules promote neutrophil infiltration into the synovium. At the same time, S1P directly activates the neutrophils resulting in the release of oxygen free radicals that destroy joint tissue. Progression of RA is associated with a change from a Th1 to a Th2 environment, and sphingosine is selectively inhibitory toward Th1 cells. Consequently, inhibiting the conversion of sphingosine to S1P should attenuate the progression of the disease. Platelets, monocytes and mast cells secrete S1P upon activation, promoting inflammatory cascades at the site of tissue damage (Yatomi et al., *Blood* 86: 193 (1995)). S1P also promotes the secretion of proteases from chondrocytes that contribute to joint destruction. Finally, S1P-mediated expression of VEGF promotes the angiogenesis necessary to support the hyperproliferation of synovial cells. Consequently, inhibiting the conversion of sphingosine to S1P should attenuate the progression of the disease.

As the processes involved in arthritis are induced by cytokines and growth factors whose action is dependent on increased signaling through SK, the SK inhibitory compounds, pharmaceutical compositions and methods of this invention are expected to be of use in the prevention and/or therapy of arthritis.

Atherosclerosis is a complex vascular disease that involves a series of coordinated cellular and molecular events characteristic of inflammatory reactions. In response to vascular injury, the first atherosclerotic lesions are initiated by acute inflammatory reactions, mostly mediated by monocytes, platelets and T lymphocytes. These inflammatory cells are activated and recruited into the subendothelial vascular space through locally expressed chemotactic factors and adhesion molecules expressed on endothelial cell surface. Continuous recruitment of additional circulating inflammatory cells into the injured vascular wall potentiates the inflammatory reaction by further activating vascular smooth muscle (VSM) cell migration and proliferation. This chronic vascular inflammatory reaction leads to fibrous cap formation, which is an oxidant-rich inflammatory milieu composed of monocytes/macrophages and VSM cells. Over time, this fibrous cap can be destabilized and ruptured by extracellular metalloproteinases secreted by resident monocytes/macrophages. The ruptured fibrous cap can easily occlude vessels resulting in acute cardiac or cerebral ischemia. This underlying mechanism of atherosclerosis indicates that activation of monocyte/macrophage and VSM cell migration and proliferation play critical roles in the development and progression of atherosclerotic lesions. Importantly, it also suggests that a therapeutic approach that blocks the activities of these vascular inflammatory cells or smooth muscle cell proliferation should be able to prevent the progression and/or development of atherosclerosis.

SK is highly expressed in platelets allowing them to phosphorylate circulating sphingosine to produce S1P. In response to vessel injury, platelets release large amounts of S1P into the sites of injury which can exert mitogenic effects on VSM cells by activating S1P receptors. S1P is also produced in activated endothelial and VSM cells. In these cells, intracellularly produced S1P functions as a second messenger molecule, regulating $Ca^{2+}$ homeostasis associated with cell proliferation and suppression of apoptosis. Additionally, deregulation of apoptosis in phagocytes is an important component of the chronic inflammatory state of atherosclerosis, and S1P protects granulocytes from apoptosis. Together, these studies indicate that activation of SK alters sphingolipid metabolism in favor of S1P formation, resulting in pro-inflammatory and hyperproliferative cellular responses.

In addition to its role in regulating cell proliferation and apoptosis, S1P has been shown to have several important effects on cells that mediate immune functions. Platelets and monocytes secrete cytokines, growth factors and S1P upon activation, promoting inflammatory cascades at the site of tissue damage. For example, TNFα has been shown to act through the induction of nuclear factor kappa B (NFκB), which has been implicated in increasing the proinflammatory enzymes nitric oxide synthase (NOS) and cyclooxygenase-2 (COX-2). COX-2 may play a key role in the inflammation of atherosclerosis through its production of prostaglandins, and oxidative stress such as that mediated by nitric oxide produced by NOS has also shown to exacerbate inflammation. Activation of SK is required for signaling responses since the ability of inflammatory cytokines to induce adhesion molecule expression via activation of NFκB is mimicked by S1P. Similarly, S1P mimics the ability of TNFα to induce the expression of COX-2 and the synthesis of $PGE_2$, and knockdown of SK by RNA interference blocks these responses to TNFα but not S1P. S1P is also a mediator of $Ca^{2+}$ influx during granulocyte activation, leading to the production of superoxide and other toxic radicals.

Together, these studies indicate that SK is a new molecular target for atherosclerosis. The use of inhibitors of SK as anti-atherosclerosis agents will prevent the deleterious activation of leukocytes, as well as prevent infiltration and smooth muscle cell hyperproliferation, making the compounds, pharmaceutical compositions and methods of this invention useful for the treatment and/or prevention of atherosclerosis.

The physiological endpoint in asthma pathology is narrowing of the bronchial tubes due to inflammation. In a large portion of asthma cases, the inflammation is initiated and later amplified by exposure to allergens. Upon inhalation, these allergens, bind to circulating IgE and then bind to the high-affinity FcεRI surface receptors expressed by inflammatory cells residing in the bronchial mucosa. This extracellular binding leads to a cascade of signaling events inside the inflammatory cells, culminating in activation of these cells and secretion of multiple factors that trigger the cells lining the bronchial airways to swell, resulting in restricted bronchial tubes and decreased air exchange. The inflammation process in response to the initial exposure to allergen may not completely subside. Furthermore, additional exposures may lead to an exaggerated response called bronchial hyper-reactivity. This hyper-reactive state can lead to a permanent condition of restricted airways through airway remodeling. Consequently, unchecked inflammatory responses to initial allergen exposure may result in chronic inflammation and permanent bronchiolar constriction. Therefore, inhibiting or diminishing this exaggerated inflammation would likely decrease the symptoms associated with asthma.

Many studies have revealed the involvement of mast cells in the inflammatory process leading to asthma, and SK has been shown to be involved in allergen-stimulated mast cell activation, a critical step in the bronchial inflammatory process. In rat basophilic leukemia RBL-2H3 cells, IgE/Ag binding to the high-affinity FcεRI receptor leads to SK activation and conversion of sphingosine to S1P (Choi et al., 1996, *Nature* 380: 634). The newly formed S1P increases intracellular calcium levels, which is necessary for mast cell activation. Alternately, high concentrations of sphingosine decrease IgE/Ag exposure-mediated leukotriene synthesis and diminished cytokine transcription and secretion (Prieschl et al., 1999, *J Exp Med* 190:1).

In addition to the key role of SK and S1P in mast cell activation, S1P also has direct effects on downstream signaling in the asthma inflammation pathway Ammit and coworkers demonstrated increased S1P levels in bronchoalveolar lavage (BAL) fluid collected from asthmatic patients 24 hours after allergen challenge compared with non-asthmatic subjects (Ammit et al., 2001, *FASEB J* 15: 1212). In conjunction with the finding that activated mast cells produce and secrete S1P, these results reveal a correlation between S1P and the asthmatic inflammatory response. To evaluate a possible role of SK and S1P exposure to cell response, ASM cultures were grown in the presence of S1P (Ammit et al., 2001 Id.). Furthermore, airway smooth muscle (ASM) cells are responsive to S1P- and SK-dependent stimuli, such as TNFα and IL-1β. Treatment with S1P increases phosphoinositide hydrolysis and intracellular calcium mobilization, both of which promote ASM contraction. Furthermore, S1P treatment increases DNA synthesis, cell number and accelerated progression of ASM cells from $G_1$ to S phase.

In addition to the direct effects on ASM cells, S1P also regulates secretion of cytokines and expression of cell adhesion molecules that amplify the inflammatory response through leukocyte recruitment and facilitating extracellular component interaction. S1P, like TNFα, induces IL-6 secretion and increases the expression of cell adhesion molecules such as VCAM-1, ICAM-1 and E-selectin (Shimamura et al., 2004, *Eur J Pharmacol* 486: 141). In addition to the effects of S1P on mast cell activation, the multiple roles of S1P, and hence SK, in the bronchiolar inflammatory phase of asthma pathogenesis clearly indicate an opportunity for pharmacologic intervention in both the acute and chronic phases of this disease.

Overall, SK is a target for new anti-asthma therapies. The use of inhibitors of SK as anti-asthma agents will inhibit cytokine-mediated activation of leukocytes, thereby preventing the deleterious activation of leukocytes, as well as preventing airway smooth muscle cell hyperproliferation, making the compounds, pharmaceutical compositions and methods of this invention useful for the treatment and/or prevention of asthma.

Chronic obstructive pulmonary disease (COPD), like asthma, involves airflow obstruction and hyperresponsiveness that is associated with aberrant neutrophil activation in the lung tissue. This is clinically manifested as chronic bronchitis, fibrosis or emphysema, which together make up the fourth leading cause of death in the United States. Since activation of inflammatory cells by chemical insults in COPD occurs through NFκB-mediated pathways similar to those activated during asthma, it is likely that the compounds, pharmaceutical compositions and methods of this invention will also be useful for the treatment and/or prevention of COPD.

Inflammation is involved in a variety of skin disorders, including psoriasis, atopic dermatitis, contact sensitivity and acne, which affect more than 20% if the population. Although topical corticosteroids have been widely used, their adverse effects prevent long-term use. Since the inflammatory responses typically involve aberrant activation of signaling pathways detailed above, it is likely that the compounds, pharmaceutical compositions and methods of this invention will also be useful for the treatment of these skin diseases.

A variety of diseases including allergic encephalomyelitis, allergic neuritis, transplant allograft rejection, graft versus host disease, myocarditis, thyroiditis, nephritis, systemic lupus erthematosus, and insulin-dependent diabetes mellitus can be induced by inappropriate activation of T cells. Common features of the pathogenesis of these diseases include infiltration by mononuclear cells, expression of CD4 and CD8 autoreactive T cells, and hyperactive signaling by inflammatory mediators such as IL-1, IL-6 and TNFα. Since the inflammatory responses typically involve aberrant activation of signaling pathways detailed above, it is likely that the compounds, pharmaceutical compositions and methods of this invention will also be useful for the treatment of these T cell-mediated diseases of immunity.

Angiogenic Diseases.

The present invention also relates to compounds, pharmaceutical compositions and methods useful for the treatment and/or prevention of diseases that involve undesired angiogenesis. More specifically, the invention relates to the use of chemical compounds and compositions that inhibit the enzymatic activity of sphingosine kinase for the treatment and/or prevention of angiogenic diseases, such as diabetic retinopathy, arthritis, cancer, psoriasis, Kaposi's sarcoma, hemangiomas, myocardial angiogenesis, atherscelortic plaque neovascularization, and ocular angiogenic diseases such as choroidal neovascularization, retinopathy of prematurity (retrolental fibroplasias), macular degeneration, corneal graft rejection, rubeosis, neuroscular glacoma and Oster Webber syndrome. The following discussion demonstrates the role of SK in several of these angiogenic diseases. Since the same processes are involved in the above listed diseases, the compounds, pharmaceutical compositions and methods of this invention will be useful for the treatment and/or prevention of a variety of diseases.

Angiogenesis refers to the state in the body in which various growth factors or other stimuli promote the formation of new blood vessels. As discussed below, this process is critical to the pathology of a variety of diseases. In each case, excessive angiogenesis allows the progression of the disease and/or the produces undesired effects in the patient. Since conserved biochemical mechanisms regulate the proliferation of vascular endothelial cells that form these new blood vessels, i.e. neovascularization, identification of methods to inhibit these mechanisms are expected to have utility for the treatment and/or prevention of a variety of diseases. The following discussion provides further details in how the compounds, compositions and methods of the present invention can be used to inhibit angiogenesis in several of these diseases.

Diabetic retinopathy is a leading cause of vision impairment, and elevation in the expression of growth factors contributes to pathogenic angiogenesis in this disease. In particular, vascular endothelial growth factor (VEGF) is a prominent contributor to the new vessel formation in the diabetic retina (Frank et al., 1997, *Arch Ophthalmol* 115: 1036, Sone et al., 1997, *Diabetologia* 40: 726), and VEGF has been shown to be elevated in patients with proliferative diabetic retinopathy (Aiello et al., 1994, *N Engl J Med* 331: 1480). In addition to diabetic retinopathy, several other debilitating ocular diseases, including age-related macular degeneration and choroidal neovascularization, are associated with excessive angiogenesis that is mediated by VEGF and other growth factors (Grant et al., 2004, *Expert Opin Investig Drugs* 13: 1275).

In the retina, VEGF is expressed in the pigmented epithelium, the neurosensory retina, the pericytes and the vascular smooth muscle layer. VEGF induces endothelial cell proliferation, favoring the formation of new vessels in the retina (Pe'er et al., 1995, *Lab Invest* 72: 638). At the same time, basic fibroblast growth factor (bFGF) in the retina is activated, and this factor acts in synergy with VEGF such that the two together induce the formation of new vessels in which the subendothelial matrix is much weaker than in normal vessels. Additionally, VEGF facilitates fluid extravasation in the interstitium, where exudates form in the retinal tissue. VEGF also promotes the fenestration of endothelial cells, a process that can give rise to intercellular channels through which fluids can leak, and disrupts tight junctions between cells. Thus, reduction of VEGF activity in the retina is likely to efficiently reduce the development and progression of retinal angiogenesis and vascular leakage which underlie the retinopathic process.

The pro-inflammatory cytokine TNFα has also been demonstrated to play a role in diabetic retinopathy since it alters the cytoskeleton of endothelial cells, resulting in leaky barrier function and endothelial cell activation (Camussi et al., 1991, *Int Arch Allergy Appl Immunol* 96: 84). These changes in retinal endothelial cells are central in the pathologies of diabetic retinopathy.

A link between the actions of VEGF and SK may be involved in driving retinopathy. SK has been shown to mediate VEGF-induced activation of ras- and mitogen-activated protein kinases (Shu et al., 2002, *Mol Cell Biol* 22: 7758). VEGF has been shown to enhance intracellular signaling responses to S1P, thereby increasing its angiogenic actions (Igarashi et al., 2003, *Proc Natl Acad Sci USA* 100: 10664). S1P has also been shown to stimulate NFκB activity (Xia et al., 1998, *Proc Natl Acad Sci USA* 95: 14196) leading to the production of COX-2, adhesion molecules and additional VEGF production, all of which have been linked to angiogenesis. Furthermore, the expression of the endothelial isoform of nitric oxide synthase (eNOS), a key signaling molecule in vascular endothelial cells and modulates a wide array of function including angiogenic responses, is regulated by SK (Igarashi et al., 2000 *J Biol Chem* 275: 32363). Clearly, SK is a central regulator of angiogenesis, supporting our hypothesis that its pharmacological manipulation may be therapeutically useful. S1P has also been shown to stimulate NFκB production which has been demonstrated to be angiogenic. NFκB leads to the production of Cox2, adhesion molecules and additional VEGF production, all of which have been linked to angiogenesis.

One of the most attractive sites of intervention in this pathway is the conversion of sphingosine to S1P by the enzyme SK. SK is the key enzyme responsible for the production of S1P synthesis in mammalian cells, which facilitates cell survival and proliferation, and mediates critical processes involved in angiogenesis and inflammation, including responses to VEGF (Shu et al., 2002, *Mol Cell Biol* 22: 7758) and TNFα (Xia et al., 1998, *Proc Natl Acad Sci USA* 95: 14196). Therefore, inhibition of S1P production is a potentially important point of therapeutic intervention for diabetic retinopathy.

The role of angiogenesis in cancer is well recognized. Growth of a tumor is dependent on neovascularization so that nutrients can be provided to the tumor cells. The major factor that promotes endothelial cell proliferation during tumor neovascularization is VEGF. As discussed above, signaling through VEGF receptors is dependent on the actions of SK. Therefore, the compounds, pharmaceutical compositions and methods of this invention will have utility for the treatment of cancer.

More than 50 eye diseases have been linked to the formation of choroidal neovascularization, although the three main diseases that cause this pathology are age-related macular degeneration, myopia and ocular trauma. Even though most of these causes are idiopathic, among the known causes are related to degeneration, infections, choroidal tumors and or trauma. Among soft contact lens wearers, choroidal neovascularization can be caused by the lack of oxygen to the eyeball. As the choroidal neovascularization is induced by growth factors whose action is dependent on increased signaling through SK, the SK inhibitory compounds, pharmaceutical compositions and methods of this invention are expected to be of use in the therapy of disorders of choroidal neovascularization.

Hemangiomas are angiogenic diseases characterized by the proliferation of capillary endothelium with accumulation of mast cells, fibroblasts and macrophages. They represent the most frequent tumors of infancy, and are characterized by rapid neonatal growth (proliferating phase). By the age of 6 to 10 months, the hemangioma's growth rate becomes proportional to the growth rate of the child, followed by a very slow regression for the next 5 to 8 years (involuting phase). Most hemangiomas occur as single tumors, whereas about 20% of the affected infants have multiple tumors, which may appear at any body site. Several studies have provided insight into the histopathology of these lesions. In particular, proliferating hemangiomas express high levels of proliferating cell nuclear antigen (a marker for cells in the S phase), type IV collagenase, VEGF and FGF-2. As the hemangiomas are induced by growth factors whose action is dependent on increased signaling through SK, the SK inhibitory compounds, pharmaceutical compositions and methods of this invention are expected to be of use in the therapy of hemangiomas.

Psoriasis and Kaposi's sarcoma are angiogenic and proliferative disorders of the skin. Hypervascular psoriatic lesions express high levels of the angiogenic inducer IL-8, whereas the expression of the endogenous inhibitor TSP-1 is decreased. Kaposi's sarcoma (KS) is the most common tumor associated with human immunodeficiency virus (HIV) infection and is in this setting almost always associated with infection by human herpes virus 8. Typical features of KS are proliferating spindle-shaped cells, considered to be the tumor cells and endothelial cells forming blood vessels. KS is a cytokine-mediated disease, highly responsive to different inflammatory mediators like IL-1β, TNF-α and IFN-γ and angiogenic factors. As the progression of psoriasis and KS are induced by growth factors whose action is dependent on increased signaling through SK, the SK inhibitory compounds, pharmaceutical compositions and methods of this invention are expected to be of use in the therapy of these disorders.

EXAMPLES

The present invention may be better understood with reference to the following examples. These examples are intended to be representative of specific embodiments of the invention, and are not intended as limiting the scope of the invention.

Representative compounds of the invention include those in Tables 1 and 2. Structures were named using Chemdraw Ultra, version 7.0.1, available from CambridgeSoft Corporation, 100 CambridgePark Drive, Cambridge, Mass. 02140, USA.

TABLE 1

Representative compounds of the invention.

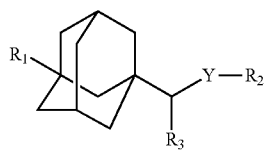

| Cmpd | Chemical name | Y | $R_3$ | $R_1$ | $R_2$ |
|---|---|---|---|---|---|
| 1 | 3-(4-Chloro-phenyl)-adamantane-1-carboxylic acid isopropylamide | NH | =O | Cl—⟨phenyl⟩— | —CH(CH$_3$)$_2$ |

TABLE 1-continued

Representative compounds of the invention.

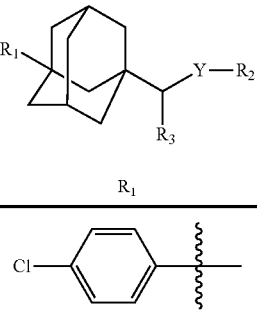

| Cmpd | Chemical name | Y | R₃ | R₁ | R₂ |
|---|---|---|---|---|---|
| 2 | 3-(4-Chloro-phenyl)-adamantane-1-carboxylic acid cyclopropylamide | NH | =O | 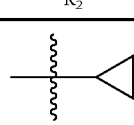 | 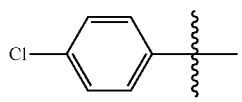 [SMILES: *c1ccc(Cl)cc1] |
| 3 | 3-(4-Chloro-phenyl)-adamantane-1-carboxylic acid (2-ethylsulfanyl-ethyl)-amide | NH | =O |  | 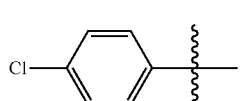 |
| 4 | 3-(4-Chloro-phenyl)-adamantane-1-carboxylic acid phenylamide | NH | =O | 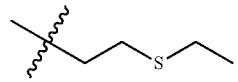 [SMILES: *CCSCC] | 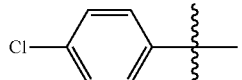 |
| 5 | Adamantane-1-carboxylic acid (4-hydroxy-phenyl)-amide | NH | =O | H | 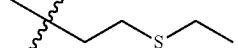 |
| 6 | 3-(4-Chloro-phenyl)-adamantane-1-carboxylic acid (4-hydroxy-phenyl)-amide | NH | =O | 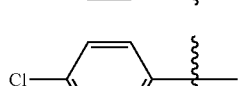 | 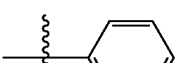 |
| 7 | Acetic acid 4-{[3-(4-chloro-phenyl)-adamantane-1-carbonyl]-amino}-phenyl ester | NH | =O | 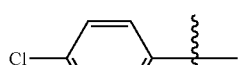 | 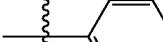 |
| 8 | 3-(4-Chloro-phenyl)-adamantane-1-carboxylic acid (2,4-dihydroxy-phenyl)-amide | NH | =O | 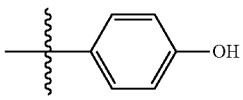 [SMILES: *c1ccc(O)cc1] | 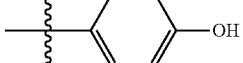 |
| 9 | 3-(4-Chloro-phenyl)-adamantane-1-carboxylic acid (3-hydroxymethyl-phenyl)-amide | NH | =O | 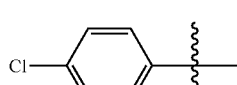 | 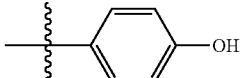 |
| 10 | Adamantane-1-carboxylic acid (4-cyanomethyl-phenyl)-amide | NH | =O | H | 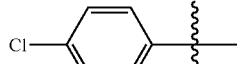 |
| 11 | 3-(4-Chloro-phenyl)-adamantane-1-carboxylic acid (4-cyanomethyl-phenyl)-amide | NH | =O |  | 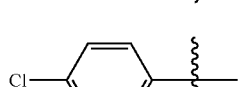 |
| 12 | 3-(4-Chloro-phenyl)-adamantane-1-carboxylic acid benzylamide | NH | =O |  | 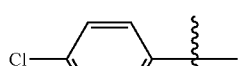 |

TABLE 1-continued

Representative compounds of the invention.

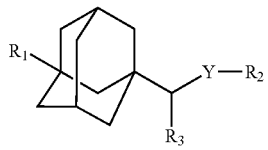

| Cmpd | Chemical name | Y | R₃ | R₁ | R₂ |
|------|---------------|---|----|----|----|
| 13 | 3-(4-Chloro-phenyl)-adamantane-1-carboxylic acid 4-tert-butyl-benzylamide | NH | =O | 4-Cl-phenyl | 4-tert-butyl-benzyl |
| 14 | 3-(4-Chloro-phenyl)-adamantane-1-carboxylic acid 4-methylsulfanyl-benzylamide | NH | =O | 4-Cl-phenyl | 4-methylsulfanyl-benzyl |
| 15 | 3-(4-Chloro-phenyl)-adamantane-1-carboxylic acid 3-trifluoromethyl-benzylamide | NH | =O | 4-Cl-phenyl | 3-CF₃-benzyl |
| 16 | 3-(4-Chloro-phenyl)-adamantane-1-carboxylic acid 4-trifluoromethyl-benzylamide | NH | =O | 4-Cl-phenyl | 4-CF₃-benzyl |
| 17 | 3-(4-Chloro-phenyl)-adamantane-1-carboxylic acid 3,5-bis-trifluoromethyl-benzylamide | NH | =O | 4-Cl-phenyl | 3,5-bis-CF₃-benzyl |
| 18 | 3-(4-Chloro-phenyl)-adamantane-1-carboxylic acid 3-fluoro-5-trifluoromethyl-benzylamide | NH | =O | 4-Cl-phenyl | 3-F-5-CF₃-benzyl |
| 19 | 3-(4-Chloro-phenyl)-adamantane-1-carboxylic acid 2-fluoro-4-trifluoromethyl-benzylamide | NH | =O | 4-Cl-phenyl | 2-F-4-CF₃-benzyl |
| 20 | 3-(4-Chloro-phenyl)-adamantane-1-carboxylic acid 3,5-difluoro-benzylamide | NH | =O | 4-Cl-phenyl | 3,5-difluoro-benzyl |

TABLE 1-continued

Representative compounds of the invention.

| Cmpd | Chemical name | Y | R₃ | R₁ | R₂ |
|---|---|---|---|---|---|
| 21 | 3-(4-Chloro-phenyl)-adamantane-1-carboxylic acid 3,4-difluoro-benzylamide | NH | =O | 4-Cl-phenyl | 3,4-difluorobenzyl |
| 22 | 3-(4-Chloro-phenyl)-adamantane-1-carboxylic acid 3,4,5-trifluoro-benzylamide | NH | =O | 4-Cl-phenyl | 3,4,5-trifluorobenzyl |
| 23 | 3-(4-Chloro-phenyl)-adamantane-1-carboxylic acid 3-chloro-4-fluoro-benzylamide | NH | =O | 4-Cl-phenyl | 3-chloro-4-fluorobenzyl |
| 24 | 3-(4-Chloro-phenyl)-adamantane-1-carboxylic acid 4-fluoro-3-trifluoromethyl-benzylamide | NH | =O | 4-Cl-phenyl | 4-fluoro-3-trifluoromethylbenzyl |
| 25 | 3-(4-Chloro-phenyl)-adamantane-1-carboxylic acid 2-chloro-4-fluoro-benzylamide | NH | =O | 4-Cl-phenyl | 2-chloro-4-fluorobenzyl |
| 26 | 3-(4-Chloro-phenyl)-adamantane-1-carboxylic acid 4-chloro-3-trifluoromethyl-benzylamide | NH | =O | 4-Cl-phenyl | 4-chloro-3-trifluoromethylbenzyl |
| 27 | 3-(4-Chloro-phenyl)-adamantane-1-carboxylic acid 3-aminomethyl-2,4,5,6-tetrachloro-benzylamide | NH | =O | 4-Cl-phenyl | 3-aminomethyl-2,4,5,6-tetrachlorobenzyl |
| 28 | 3-(4-Chloro-phenyl)-adamantane-1-carboxylic acid [1-(4-chloro-phenyl)-ethyl]-amide | NH | =O | 4-Cl-phenyl | 1-(4-chlorophenyl)ethyl |

TABLE 1-continued

Representative compounds of the invention.

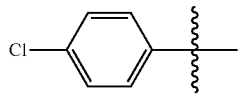

| Cmpd | Chemical name | Y | $R_3$ | $R_1$ | $R_2$ |
|---|---|---|---|---|---|
| 29 | 3-(4-Chloro-phenyl)-adamantane-1-carboxylic acid [1-(4-bromo-phenyl)-ethyl]-amide | NH | =O | 4-Cl-phenyl | 1-(4-bromophenyl)ethyl |
| 30 | 3-(4-Chloro-phenyl)-adamantane-1-carboxylic acid 4-methanesulfonyl-benzylamide | NH | =O | 4-Cl-phenyl | 4-methanesulfonyl-benzyl |
| 31 | 3-(4-Chloro-phenyl)-adamantane-1-carboxylic acid 4-dimethylamino-benzylamide | NH | =O | 4-Cl-phenyl | 4-dimethylamino-benzyl |
| 32 | 3-(4-Chloro-phenyl)-adamantane-1-carboxylic acid 4-trifluoromethoxy-benzylamide | NH | =O | 4-Cl-phenyl | 4-trifluoromethoxy-benzyl |
| 33 | 3-(4-Chloro-phenyl)-adamantane-1-carboxylic acid 3-trifluoromethoxy-benzylamide | NH | =O | 4-Cl-phenyl | 3-trifluoromethoxy-benzyl |
| 34 | 3-(4-Chloro-phenyl)-adamantane-1-carboxylic acid 4-phenoxy-benzylamide | NH | =O | 4-Cl-phenyl | 4-phenoxy-benzyl |
| 35 | Adamantane-1-carboxylic acid 3,4-dihydroxy-benzylamide | NH | =O | H | 3,4-dihydroxy-benzyl |
| 36 | 3-(4-Chloro-phenyl)-adamantane-1-carboxylic acid 3,4-dihydroxy-benzylamide | NH | =O | 4-Cl-phenyl | 3,4-dihydroxy-benzyl |

TABLE 1-continued

Representative compounds of the invention.

| Cmpd | Chemical name | Y | R3 | R1 | R2 |
|---|---|---|---|---|---|
| 37 | 3-(4-Chloro-phenyl)-adamantane-1-carboxylic acid phenethyl-amide | NH | =O | 4-Cl-phenyl | -CH2CH2-phenyl |
| 38 | 3-(4-Chloro-phenyl)-adamantane-1-carboxylic acid [2-(4-fluoro-phenyl)-ethyl]-amide | NH | =O | 4-Cl-phenyl | -CH2CH2-(4-F-phenyl) |
| 39 | 3-(4-Chloro-phenyl)-adamantane-1-carboxylic acid [2-(4-bromo-phenyl)-ethyl]-amide | NH | =O | 4-Cl-phenyl | -CH2CH2-(4-Br-phenyl) |
| 40 | 3-(4-Chloro-phenyl)-adamantane-1-carboxylic acid [2-(4-hydroxy-phenyl)-ethyl]-amide | NH | =O | 4-Cl-phenyl | -CH2CH2-(4-OH-phenyl) |
| 41 | 3-(4-Chloro-phenyl)-adamantane-1-carboxylic acid 4-phenoxy-benzylamide | NH | =O | 4-Cl-phenyl | -CH2CH2-(4-OCH3-phenyl) |
| 42 | 3-(4-Chloro-phenyl)-adamantane-1-carboxylic acid [2-(3-bromo-4-methoxy-phenyl)-ethyl]-amide | NH | =O | 4-Cl-phenyl | -CH2CH2-(3-Br-4-OCH3-phenyl) |
| 43 | Adamantane-1-carboxylic acid [2-(3,4-dihydroxy-phenyl)-ethyl]-amide | NH | =O | H | -CH2CH2-(3,4-diOH-phenyl) |
| 44 | 3-(4-Chloro-phenyl)-adamantane-1-carboxylic acid [2-(3,4-dihydroxy-phenyl)-ethyl]-amide | NH | =O | 4-Cl-phenyl | -CH2CH2-(3,4-diOH-phenyl) |

TABLE 1-continued

Representative compounds of the invention.

| Cmpd | Chemical name | Y | R₃ | R₁ | R₂ |
|---|---|---|---|---|---|
| 45 | 3-(4-Chloro-phenyl)-adamantane-1-carboxylic acid (2-benzo[1,3]dioxol-5-yl-ethyl)-amide | NH | =O | 4-Cl-phenyl | 2-(benzo[1,3]dioxol-5-yl)ethyl |
| 46 | 3-(4-Chloro-phenyl)-adamantane-1-carboxylic acid [2-(3-phenoxy-phenyl)-ethyl]-amide | NH | =O | 4-Cl-phenyl | 2-(3-phenoxy-phenyl)ethyl |
| 47 | 3-(4-Chloro-phenyl)-adamantane-1-carboxylic acid [2-(4-phenoxy-phenyl)-ethyl]-amide | NH | =O | 4-Cl-phenyl | 2-(4-phenoxy-phenyl)ethyl |
| 48 | 3-(4-Chloro-phenyl)-adamantane-1-carboxylic acid (3-phenyl-propyl)-amide | NH | =O | 4-Cl-phenyl | 3-phenyl-propyl |
| 49 | 3-(4-Chloro-phenyl)-adamantane-1-carboxylic acid (biphenyl-4-ylmethyl)-amide | NH | =O | 4-Cl-phenyl | biphenyl-4-ylmethyl |
| 50 | Adamantane-1-carboxylic acid (1-methyl-piperidin-4-yl)-amide | NH | =O | H | 1-methyl-piperidin-4-yl |
| 51 | 3-(4-Chloro-phenyl)-adamantane-1-carboxylic acid (1-methyl-piperidin-4-yl)-amide | NH | =O | 4-Cl-phenyl | 1-methyl-piperidin-4-yl |
| 52 | 3-(4-Chloro-phenyl)-adamantane-1-carboxylic acid (4-methyl-piperazin-1-yl)-amide | NH | =O | 4-Cl-phenyl | 4-methyl-piperazin-1-yl |
| 53 | 3-(4-Chloro-phenyl)-adamantane-1-carboxylic acid (3-tert-butylamino-propyl)-amide | NH | =O | 4-Cl-phenyl | 3-tert-butylamino-propyl |
| 54 | 3-(4-Chloro-phenyl)-adamantane-1-carboxylic acid (3-pyrrolidin-1-yl-propyl)-amide | NH | =O | 4-Cl-phenyl | 3-pyrrolidin-1-yl-propyl |

TABLE 1-continued

Representative compounds of the invention.

| Cmpd | Chemical name | Y | R$_3$ | R$_1$ | R$_2$ |
|---|---|---|---|---|---|
| 55 | 3-(4-Chloro-phenyl)-adamantane-1-carboxylic acid [3-(2-oxo-pyrrolidin-1-yl)-propyl]-amide | NH | =O | 4-Cl-phenyl | propyl-(2-oxo-pyrrolidin-1-yl) |
| 56 | Adamantane-1-carboxylic acid [2-(1-methyl-pyrrolidin-2-yl)-ethyl]-amide | NH | =O | H | ethyl-(1-methyl-pyrrolidin-2-yl) |
| 57 | 3-(4-Chloro-phenyl)-adamantane-1-carboxylic acid [2-(1-methyl-pyrrolidin-2-yl)-ethyl]-amide | NH | =O | 4-Cl-phenyl | ethyl-(1-methyl-pyrrolidin-2-yl) |
| 58 | 3-(4-Chloro-phenyl)-adamantane-1-carboxylic acid (2-morpholin-4-yl-ethyl)-amide | NH | =O | 4-Cl-phenyl | ethyl-morpholin-4-yl |
| 59 | 3-(4-Chloro-phenyl)-adamantane-1-carboxylic acid (2-piperazin-1-yl-ethyl)-amide | NH | =O | 4-Cl-phenyl | ethyl-piperazin-1-yl |
| 60 | Adamantane-1-carboxylic acid (pyridin-4-ylmethyl)-amide | NH | =O | H | pyridin-4-ylmethyl |
| 61 | 3-(4-Fluoro-phenyl)-adamantane-1-carboxylic acid (pyridin-4-ylmethyl)-amide | NH | =O | 4-F-phenyl | pyridin-4-ylmethyl |
| 62 | 3-(4-Chloro-phenyl)-adamantane-1-carboxylic acid (pyridin-4-ylmethyl)-amide | NH | =O | 4-Cl-phenyl | pyridin-4-ylmethyl |
| 63 | Adamantane-1-carboxylic acid (pyridin-4-ylmethyl)-amide | NH | =O | H | ethyl-pyridin-4-yl |

TABLE 1-continued

Representative compounds of the invention.

| Cmpd | Chemical name | Y | R₃ | R₁ | R₂ |
|---|---|---|---|---|---|
| 64 | 3-(4-Chloro-phenyl)-adamantane-1-carboxylic acid (2-pyridin-4-yl-ethyl)-amide | NH | =O | 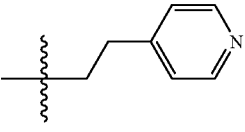 [SMILES: *CCc1ccncc1] | 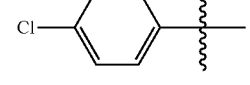 |
| 65 | 3-(4-Chloro-phenyl)-adamantane-1-carboxylic acid (3-imidazol-1-yl-propyl)-amide | NH | =O | 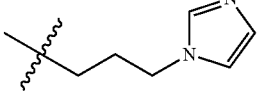 | 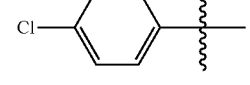 |
| 66 | 3-(4-Chloro-phenyl)-adamantane-1-carboxylic acid (2-methyl-1H-indol-5-yl)-amide | NH | =O | 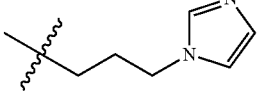 | 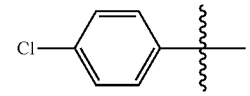 |
| 67 | 3-(4-Chloro-phenyl)-adamantane-1-carboxylic acid (1H-tetrazol-5-yl)-amide | NH | =O | 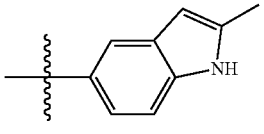 [SMILES: *c1ccc2[nH]c(C)cc2c1] | 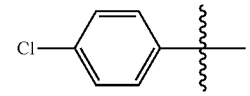 |
| 68 | 3-(4-Chloro-phenyl)-adamantane-1-carboxylic acid (9-ethyl-9H-carbazol-3-yl)-amide | NH | =O | 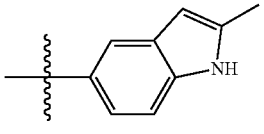 [SMILES: *c1ccc2[nH]c(C)cc2c1] | 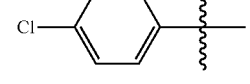 |
| 69 | Adamantane-1-carboxylic acid [4-(4-chloro-phenyl)-thiazol-2-yl]-amide | NH | =O | H | 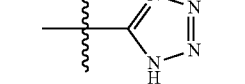 |
| 70 | 3-(4-Chloro-phenyl)-adamantane-1-carboxylic acid [4-(4-chloro-phenyl)-thiazol-2-yl]-amide | NH | =O | 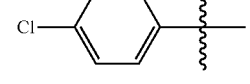 | 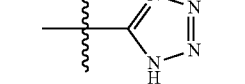 |
| 71 | 3-(4-Chloro-phenyl)-adamantane-1-carboxylic acid benzothiazol-2-ylamide | NH | =O | 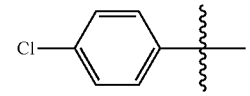 | 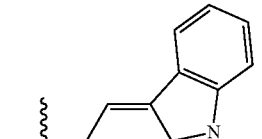 |
| 72 | 3-(4-Chloro-phenyl)-adamantane-1-carboxylic acid (5-chloro-benzooxazol-2-yl)-amide | NH | =O | 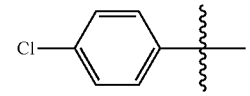 | 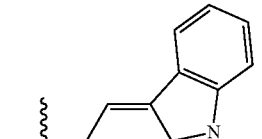 |

TABLE 1-continued

Representative compounds of the invention.

| Cmpd | Chemical name | Y | R₃ | R₁ | R₂ |
|---|---|---|---|---|---|
| 73 | 3-(4-Chloro-phenyl)-adamantane-1-carboxylic acid (9H-purin-6-yl)-amide | NH | =O | 4-Cl-phenyl | 9H-purin-6-yl |
| 75 | [3-(4-Chloro-phenyl)-adamantan-1-ylmethyl]-isopropyl-amine | NH | H | 4-Cl-phenyl | isopropyl |
| 76 | 4- and -phenol | NH | H | 4-Cl-phenyl | 4-hydroxyphenyl |
| 77 | [3-(4-Chloro-phenyl)-adamantan-1-ylmethyl]-(4-trifluoromethyl-benzyl)-amine | NH | H | 4-Cl-phenyl | 4-CF₃-benzyl |
| 78 | [3-(4-Chloro-phenyl)-adamantan-1-ylmethyl]-(2-fluoro-4-trifluoromethyl-benzyl)-amine | NH | H | 4-Cl-phenyl | 2-F-4-CF₃-benzyl |
| 79 | [3-(4-Chloro-phenyl)-adamantan-1-ylmethyl]-(4-fluoro-3-trifluoromethyl-benzyl)-amine | NH | H | 4-Cl-phenyl | 4-F-3-CF₃-benzyl |
| 80 | [3-(4-Chloro-phenyl)-adamantan-1-ylmethyl]-(4-trifluoromethoxy-benzyl)-amine | NH | H | 4-Cl-phenyl | 4-OCF₃-benzyl |
| 81 | [3-(4-Chloro-phenyl)-adamantan-1-ylmethyl]-[2-(3-phenoxy-phenyl)-ethyl]-amine | NH | H | 4-Cl-phenyl | 2-(3-phenoxy-phenyl)-ethyl |
| 82 | [3-(4-Chloro-phenyl)-adamantan-1-ylmethyl]-(1-methyl-piperidin-4-yl)-amine | NH | H | 4-Cl-phenyl | 1-methyl-piperidin-4-yl |

TABLE 1-continued

Representative compounds of the invention.

| Cmpd | Chemical name | Y | R₃ | R₁ | R₂ |
|---|---|---|---|---|---|
| 83 | [3-(4-Chloro-phenyl)-adamantan-1-ylmethyl]-(4-methyl-piperazin-1-yl)-amine | NH | H | 4-Cl-phenyl | 4-methyl-piperazin-1-yl |
| 84 | N-tert-Butyl-N'-[3-(4-chloro-phenyl)-adamantan-1-ylmethyl]-propane-1,3-diamine | NH | H | 4-Cl-phenyl | -(CH₂)₃-NH-C(CH₃)₃ |
| 85 | [3-(4-Chloro-phenyl)-adamantan-1-ylmethyl]-(3-pyrrolidin-1-yl-propyl)-amine | NH | H | 4-Cl-phenyl | -(CH₂)₃-pyrrolidin-1-yl |
| 86 | [3-(4-Chloro-phenyl)-adamantan-1-ylmethyl]-[2-(1-methyl-pyrrolidin-2-yl)-ethyl]-amine | NH | H | 4-Cl-phenyl | -(CH₂)₂-(1-methyl-pyrrolidin-2-yl) |
| 87 | [3-(4-Chloro-phenyl)-adamantan-1-ylmethyl]-(2-morpholin-4-yl-ethyl)-amine | NH | H | 4-Cl-phenyl | -(CH₂)₂-morpholin-4-yl |
| 88 | [3-(4-Chloro-phenyl)-adamantan-1-ylmethyl]-pyridin-4-ylmethyl-amine | NH | H | 4-Cl-phenyl | -CH₂-pyridin-4-yl |
| 89 | [3-(4-Chloro-phenyl)-adamantan-1-ylmethyl]-(9-ethyl-9H-carbazol-3-yl)-amine | NH | H | 4-Cl-phenyl | 9-ethyl-9H-carbazol-3-yl |
| 90 | [3-(4-Chloro-phenyl)-adamantan-1-ylmethyl]-[5-(4-chloro-phenyl)-thiazol-2-yl]-amine | NH | H | 4-Cl-phenyl | 5-(4-chloro-phenyl)-thiazol-2-yl |
| 91 | 1-[3-(4-Chloro-phenyl)-adamantan-1-yl]-ethylamine | NH | CH₃ | 4-Cl-phenyl | H |
| 92 | {1-[3-(4-Chloro-phenyl)-adamantan-1-yl]-ethyl}-isopropyl-amine | NH | CH₃ | 4-Cl-phenyl | isopropyl |

TABLE 1-continued

Representative compounds of the invention.

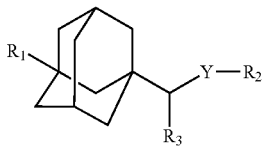

| Cmpd | Chemical name | Y | R₃ | R₁ | R₂ |
|---|---|---|---|---|---|
| 93 | Phenyl-[1-(3-phenyl-adamantan-1-yl)-ethyl]-amine | NH | CH₃ | phenyl | phenyl |
| 94 | {1-[3-(4-Fluoro-phenyl)-adamantan-1-yl]-ethyl}-phenyl-amine | NH | CH₃ | 4-F-phenyl | phenyl |
| 95 | {1-[3-(4-Chloro-phenyl)-adamantan-1-yl]-ethyl}-phenyl-amine | NH | CH₃ | 4-Cl-phenyl | phenyl |
| 96 | (1-Adamantan-1-yl-ethyl)-benzyl-amine | NH | CH₃ | H | benzyl |
| 97 | Benzyl-[1-(3-phenyl-adamantan-1-yl)-ethyl]-amine | NH | CH₃ | phenyl | benzyl |
| 98 | Benzyl-{1-[3-(4-fluoro-phenyl)-adamantan-1-yl]-ethyl}-amine | NH | CH₃ | 4-F-phenyl | benzyl |
| 99 | Benzyl-{1-[3-(4-chloro-phenyl)-adamantan-1-yl]-ethyl}-amine | NH | CH₃ | 4-Cl-phenyl | benzyl |
| 100 | (4-tert-Butyl-benzyl)-{1-[3-(4-chloro-phenyl)-adamantan-1-yl]-ethyl}-amine | NH | CH₃ | 4-Cl-phenyl | 4-tert-butyl-benzyl |
| 101 | [1-(4-Bromo-phenyl)-ethyl]-{1-[3-(4-chloro-phenyl)-adamantan-1-yl]-ethyl}-amine | NH | CH₃ | 4-Cl-phenyl | 1-(4-Br-phenyl)-ethyl |
| 102 | (1-Adamantan-1-yl-ethyl)-[2-(4-bromo-phenyl)-ethyl]-amide | NH | CH₃ | H | 2-(4-Br-phenyl)-ethyl |

TABLE 1-continued

Representative compounds of the invention.

| Cmpd | Chemical name | Y | R₃ | R₁ | R₂ |
|---|---|---|---|---|---|
| 103 | [2-(4-Bromo-phenyl)-ethyl]-{1-[3-(4-chloro-phenyl)-adamantan-1-yl]-ethyl}-amine | NH | CH₃ | 4-Cl-phenyl | -CH₂CH₂-(4-Br-phenyl) |
| 104 | (1-Adamantan-1-yl-ethyl)-(1-methyl-piperidin-4-yl)-amine | NH | CH₃ | H | 1-methyl-piperidin-4-yl |
| 105 | (1-Methyl-piperidin-4-yl)-[1-(3-phenyl-adamantan-1-yl)-ethyl]-amine | NH | CH₃ | phenyl | 1-methyl-piperidin-4-yl |
| 106 | {1-[3-(4-Fluoro-phenyl)-adamantan-1-yl]-ethyl}-(1-methyl-piperidin-4-yl)-amine | NH | CH₃ | 4-F-phenyl | 1-methyl-piperidin-4-yl |
| 107 | {1-[3-(4-Chloro-phenyl)-adamantan-1-yl]-ethyl}-(1-methyl-piperidin-4-yl)-amine | NH | CH₃ | 4-Cl-phenyl | 1-methyl-piperidin-4-yl |
| 108 | {1-[3-(4-Chloro-phenyl)-adamantan-1-yl]-ethyl}-(4-methyl-piperazin-1-yl)-amine | NH | CH₃ | 4-Cl-phenyl | 4-methyl-piperazin-1-yl |
| 109 | {1-[3-(Phenyl)-adamantan-1-yl]-ethyl}-pyridin-4-ylmethyl-amine | NH | CH₃ | phenyl | -CH₂-(pyridin-4-yl) |
| 110 | {1-[3-(4-Chloro-phenyl)-adamantan-1-yl]-ethyl}-(6-chloro-pyridin-3-ylmethyl)-amine | NH | CH₃ | 4-Cl-phenyl | -CH₂-(6-chloro-pyridin-3-yl) |
| 111 | {1-[3-(4-Chloro-phenyl)-adamantan-1-yl]-ethyl}-(2-pyridin-4-yl-ethyl)-amine | NH | CH₃ | 4-Cl-phenyl | -CH₂CH₂-(pyridin-4-yl) |
| 112 | {1-[3-(4-Chloro-phenyl)-adamantan-1-yl]-ethyl}-(3H-imidazol-4-ylmethyl)-amine | NH | CH₃ | 4-Cl-phenyl | -CH₂-(1H-imidazol-4-yl) |
| 113 | {1-[3-(4-Chloro-phenyl)-adamantan-1-yl]-ethyl}-(2-methyl-1H-indol-5-yl)-amine | NH | CH₃ | 4-Cl-phenyl | 2-methyl-1H-indol-5-yl |

TABLE 1-continued

Representative compounds of the invention.

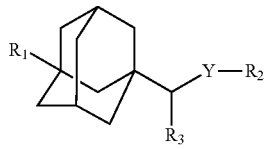

| Cmpd | Chemical name | Y | R₃ | R₁ | R₂ |
|---|---|---|---|---|---|
| 114 | {1-[3-(4-Chloro-phenyl)-adamantan-1-yl]-ethyl}-(9-ethyl-9H-carbazol-3-yl)-amine | NH | CH₃ | 4-Cl-phenyl | 9-ethyl-carbazol-3-yl |
| 115 | {1-[3-(4-Chloro-phenyl)-adamantan-1-yl]-ethyl}-(9-ethyl-9H-carbazol-3-ylmethyl)-amine | NH | CH₃ | 4-Cl-phenyl | (9-ethyl-carbazol-3-yl)methyl |
| 116 | 9-Ethyl-9H-carbazole-3-carboxylic acid {1-[3-(4-chloro-phenyl)-adamantan-1-yl]-ethyl}-amide | NH | CH₃ | 4-Cl-phenyl | 9-ethyl-carbazol-3-yl-carbonyl |
| 117 | 1-{1-[3-(4-Chloro-phenyl)-adamantan-1-yl]-ethyl}-3-(4-chloro-3-trifluoromethyl-phenyl)-urea | NH | CH₃ | 4-Cl-phenyl | (4-chloro-3-trifluoromethyl-phenyl)-aminocarbonyl |
| 118 | 1-{1-[3-(4-Chloro-phenyl)-adamantan-1-yl]-ethyl}-3-(4-chloro-3-trifluoromethyl-phenyl)-urea | NH | CH₃ | 4-Cl-phenyl | (4-chloro-3-trifluoromethyl-phenyl)-aminocarbonyl |
| 119 | (4-Bromo-thiophen-2-ylmethyl)-{1-[3-(4-chloro-phenyl)-adamantan-1-yl]-ethyl}-amine | NH | CH₃ | 4-Cl-phenyl | (4-bromo-thiophen-2-yl)methyl |
| 120 | {1-[3-(4-Chloro-phenyl)-adamantan-1-yl]-ethyl}-(4-phenyl-thiophen-2-ylmethyl)-amine | NH | CH₃ | 4-Cl-phenyl | (4-phenyl-thiophen-2-yl)methyl |

TABLE 2

Representative compounds of the invention.

| Cmpd | Chemical name | R₁ | R₂ |
|---|---|---|---|
| 121 | 3-Phenyl-adamantane-1-carboxylic acid | phenyl | OH |
| 122 | 3-(4-Fluoro-phenyl)-adamantane-1-carboxylic acid | 4-fluorophenyl | OH |
| 123 | 3-(4-Chloro-phenyl)-adamantane-1-carboxylic acid | 4-chlorophenyl | OH |
| 124 | 1-Adamantan-1-yl-ethanone | H | CH₃ |
| 125 | 1-(3-Phenyl-adamantan-1-yl)-ethanone | phenyl | CH₃ |
| 126 | 1-[3-(4-Fluoro-phenyl)-adamantan-1-yl]-ethanone | 4-fluorophenyl | CH₃ |
| 127 | 1-[3-(4-Chloro-phenyl)-adamantan-1-yl]-ethanone | 4-chlorophenyl | CH₃ |
| 128 | 2-(Adamantane-1-carbonyl)-malonic acid dimethyl ester | H | CH(CO₂Me)₂ |
| 129 | 2-[3-(4-Chloro-phenyl)-adamantane-1-carbonyl]-malonic acid dimethyl ester | 4-chlorophenyl | CH(CO₂Me)₂ |
| 130 | 3-(4-Chloro-phenyl)-1-[3-(4-chloro-phenyl)-adamantan-1-yl]-propenone | 4-chlorophenyl | CH=CH-(4-Cl-C₆H₄) |
| 131 | 4-{3-[3-(4-Chloro-phenyl)-adamantan-1-yl]-3-oxo-propenyl}-benzonitrile | 4-chlorophenyl | CH=CH-(4-CN-C₆H₄) |

TABLE 2-continued

Representative compounds of the invention.

| Cmpd | Chemical name | R₁ | R₂ |
|------|---------------|----|----|
| 132 | 1-[3-(4-Chloro-phenyl)-adamantan-1-yl]-3-(4-hydroxy-phenyl)-propenone | Cl-phenyl | -CH=CH-(4-hydroxyphenyl) |
| 133 | 1-[3-(4-Chloro-phenyl)-adamantan-1-yl]-3-naphthalen-2-yl-propenone | Cl-phenyl | -CH=CH-(naphthalen-2-yl) |
| 134 | 1-[3-(4-Chloro-phenyl)-adamantan-1-yl]-3-(6-chloro-pyridin-3-yl)-propenone | Cl-phenyl | -CH=CH-(6-chloropyridin-3-yl) |
| 135 | 1-[3-(4-Chloro-phenyl)-adamantan-1-yl]-3-(1H-imidazol-4-yl)-propenone | Cl-phenyl | -CH=CH-(1H-imidazol-4-yl) |
| 136 | 1-[3-(4-Chloro-phenyl)-adamantan-1-yl]-3-(9-ethyl-9H-carbazol-3-yl)-propenone | Cl-phenyl | -CH=CH-(9-ethyl-9H-carbazol-3-yl) |
| 137 | 1-[3-(4-Chloro-phenyl)-adamantan-1-yl]-3-(4-phenyl-thiophen-2-yl)-propenone | Cl-phenyl | -CH=CH-(4-phenylthiophen-2-yl) |

General methods. NMR spectra were obtained on Varian 300 instruments in CDCl₃, DMSO-d₆. Chemical shifts are quoted relative to TMS for ¹H- and ¹³C-NMR spectra. Solvents were dried and distilled prior to use. Reactions requiring anhydrous conditions were conducted under an atmosphere of nitrogen and column chromatography was carried out over silica gel (Merck, silica gel 60, 230-400 mesh) All reagents and commercially available materials were used without further purification.

Example 1

Method for the synthesis of 3-(4-chloro-phenyl)-adamantane-1-carboxylic acid (pyridin-4-ylmethyl)-amide, Compound 62

As an example, a process for the synthesis of Compound 62 is described in Scheme 1. The direct bromination of adamantane-1-carboxylic acid (1) in the presence of aluminum chloride (AlCl₃) gave 3-bromide derivative (2) of 1 which was converted to (3) by the reaction of Friedel-Crafts reaction. 3 was reacted with thionyl chloride (SOCl₂) to give 3-R-substituted-1-adamantanecarbonyl chlorides 4. By reaction 4 with a substituted amine, for example, 4-aminomethylpyridin (5), in THF, (6, also represented as Compound 62) and related amide compounds were obtained.

Scheme 1.

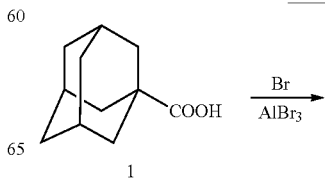

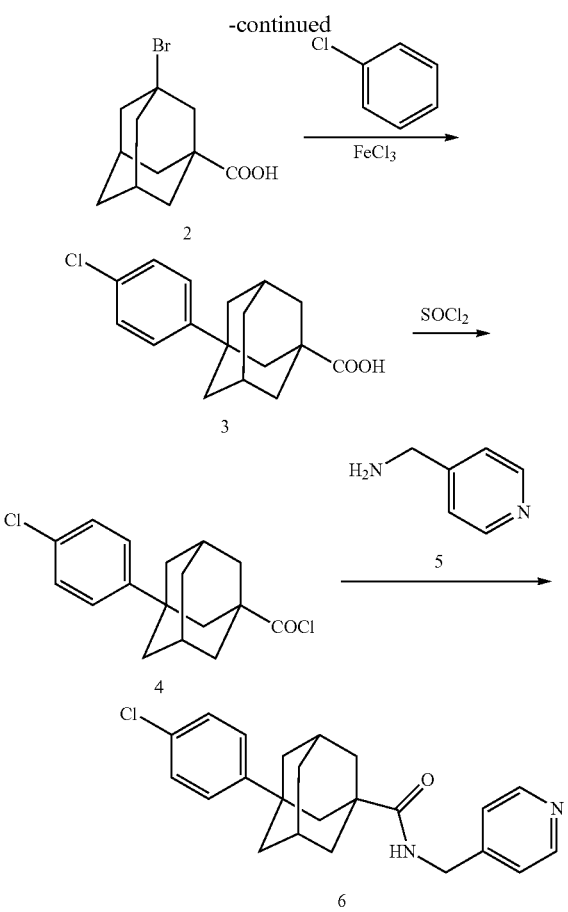

with 10% NaOH. The alkaline extraction was acidified with 2N $H_2SO_4$ and provided 49 g (yield=75.7%) of 3-bromo-adamantane-1-carboxylic acid (2).

Over a 30 minute period, 3-bromo-adamantane-1-carboxylic acid (2) (16.0 g, 61.7 mmol) in 50 ml of dry chlorobenzene at −10° C. was added to 100 ml dry chlorobenzene and 9.3 g, 70 mmol $AlCl_3$. The mixture was then warmed to room temperature for 1 hour and then heated to 90° C. for 10 hours. The mixture was then poured onto 200 g of crushed ice, and the filtered to provide 14.2 g (yield=79.3%) of 3-(4-chloro-phenyl)-adamantane-1-carboxylic acid (3).

3 reacted with an equimolar amount of 1,1'-carbonyl diimidazole (CDI) to give intermediate 3-R-substituted-1-adamantanecarbonyl imidazole (4). By reaction of 4 with a substituted amine, the corresponding adamantylamide was obtained.

For example, reaction of 3 with 4-aminomethylpyridine (5), in toluene, produced {3-(4-Chloro-phenyl)-adamantane-1-carboxylic acid (pyridin-4-ylmethyl)-amide} (6 also represented as Compound 62) with a yield of 92.6% and a melting point of 128-130° C. $^1H$ NMR (300 MHz, $CDCl_3$) δ 1.72-2.25 (m, 12H, Admant-CH), 4.44-4.46 (d, J=6 Hz, 2H, $CH_2$-Py), 6.18 (m, 1H, HN), 7.13-7.15 (d, J=6 Hz, 2H, H-Py), 7.15-7.30 (m, 4H, H-Ph), 8.52-8.54 (d, J=6 Hz, 2H, H-Py); $^{13}C$ NMR (300 MHz, $CDCl_3$) δ 28.98, 35.73, 36.71, 38.77, 42.18, 42.37, 44.88, 122.38, 125.30, 126.57, 128.56, 129.26, 148.39, 150.20 177.76; MS m/z (rel intensity) 381.50 ($MH^+$, 100), 383.41 (90), 384.35 (80).

Example 2

A Second Method for the Synthesis of Compound 62

A second method for the synthesis of Compound 62 and related adamantylamides is described in Scheme 2. 3-phenyl substituted intermediate (3) was prepared as described above. 3 reacted with 1,1'-carbonyldiimidazole (CDI) to give 3-R-substituted-1-adamantanecarbonylimidazole intermediate (4). By reaction of 4 with a substituted amine, for example 4-aminomethylpyridine 5, in toluene, 6 {3-(4-Chloro-phenyl)-adamantane-1-carboxylic acid (pyridin-4-ylmethyl)-amide} was obtained.

More specifically, adamantane-1-carboxylic acid (1) (45 g, 0.25 mol) was added to mixture of $AlCl_3$ (45 g, 0.34 mol) and $Br_2$ (450 g) at 0° C. and stirred at 0-10° C. for 48 hrs, kept 5 hrs at about 20° C., poured on to 500 g crushed ice, diluted with 300 ml $CHCl_3$ and decolorized with solid $Na_2S_2O_5$. The aqueous phase was extracted with $Et_2O$ (50 ml×2). The combined organic solution was washed with $H_2O$ and extracted Scheme 2.

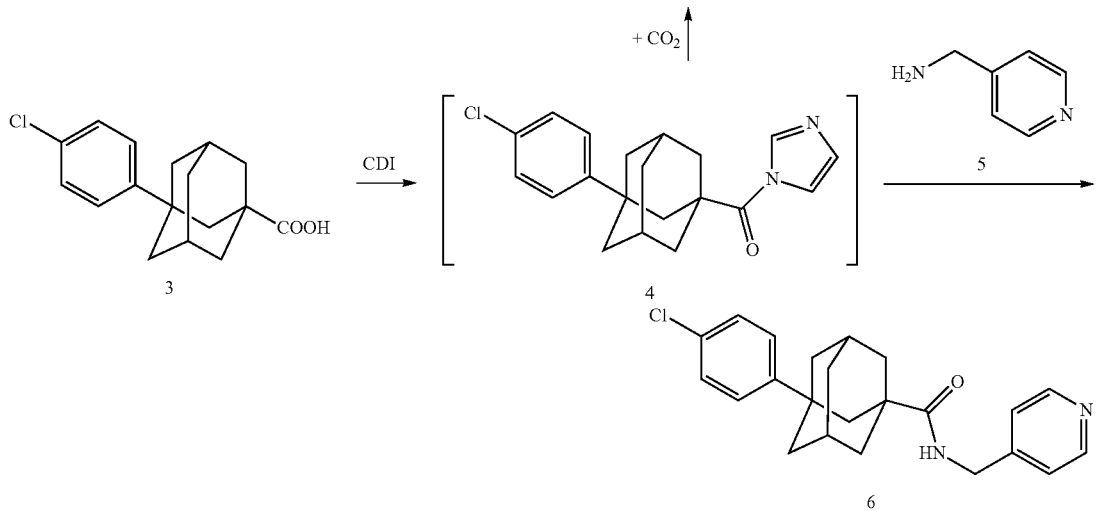

A diverse set of substituted aryladamantanes can be efficiently synthesized by condensation of various aromatic compounds with 2, and a variety of such compounds are commercially available. Additionally, amidation of 3 can be efficiently completed using a variety of coupling reagents and primary amine-containing compounds. The following Example provides several representatives of the products of this process; however, these methods can be adapted to produce many structurally related adamantylamides that are considered to be subjects of this invention.

Example 3

Synthesis of Adamantylamides

The methods described in Example 1 or 2 were used to prepare a library of substituted adamantylamides. Data provided below include: the amount synthesized, the yield of the amidation reaction, the melting point (m.p.) of the compound, mass spectral (MS) data for the compound, and NMR spectral data for the compound.

Compound 1: 3-(4-Chloro-phenyl)-adamantane-1-carboxylic acid isopropylamide. Yield=81%; m.p.: 140-141.5° C.; MS m/z (rel intensity) 332 (MH$^+$, 95).

Compound 2: 3-(4-Chloro-phenyl)-adamantane-1-carboxylic acid cyclopropylamide. 90 mg, Yield=78.3%; m.p.: 145-148° C.; $^1$H NMR (300 MHz, CDCl$_3$) δ 0.44-0.46 (m, 2H, CH$_2$), 0.76-0.78 (m, 2H, CH$_2$), 1.59-1.92 (m, 12H, Admant-CH), 2.25 (s, 2H, Admant-CH), 2.62-2.65 (m, 1H, CH), 5.64 (m, 1H, HN), 7.28-7.30 (m, 4H, H-Ph); $^{13}$C NMR (300 MHz, CDCl$_3$) δ 6.7, 22.7, 28.8, 35.5, 36.5, 38.4, 42.0, 44.5, 126.2, 128.1, 131.4, 148.2, 178.5; MS m/z (rel intensity) 330.46 (MH$^+$, 100), 331.47 (25), 332.46 (35).

Compound 3: 3-(4-Chloro-phenyl)-adamantane-1-carboxylic acid (2-ethylsulfanyl-ethyl)-amide. 180 mg, Yield=92.0%; m.p.: 101-103° C.; $^1$H NMR (300 MHz, CDCl$_3$) δ 1.24-1.29 (t, J=7.5 Hz, 3H, CH$_3$), 1.74-1.97 (m, 12H, Admant-CH), 2.27 (s, 2H, Admant-CH), 2.52-2.59 (q, J=7.5 Hz, 2H, CH$_2$), 2.65-2.70 (t, J=7.5 Hz, 2H, CH$_2$), 3.41-3.47 (m, 2H, CH$_2$), 6.12 (m, 1H, HN), 7.24-7.28 (m, 4H, Ar—H), 7.38-7.45 (m, 2H, Ar—H); $^{13}$C NMR (300 MHz, CDCl$_3$) δ 15.1, 25.7, 29.0, 31.6, 35.8, 36.7, 38.3, 38.6, 42.0, 42.3, 44.7, 126.6, 128.5, 148.6, 177.6; MS m/z (rel intensity) 373.6 (MH$^+$, 100), 374.6 (25), 375.6 (40).

Compound 4: 3-(4-Chloro-phenyl)-adamantane-1-carboxylic acid phenylamide. 120 mg, Yield=68.5%; m.p.: 190-192° C.; MS m/z (rel intensity) 366 (MH$^+$, 35).

Compound 5: Adamantane-1-carboxylic acid (4-hydroxyphenyl)-amide. 77 mg, Yield=57%; m.p.: 224-226° C.; MS m/z (rel intensity) 272 (MH$^+$, 50).

Compound 6: 3-(4-Chloro-phenyl)-adamantane-1-carboxylic acid (4-hydroxy-phenyl)-amide. Yield=66%; m.p.: 240-242° C.; $^1$H NMR (200 MHz, CDCl$_3$) δ 0.86-2.32 (m, 14H, Admant-H), 6.75-6.78 (d, J=9 Hz, 2H, Ar—H), 7.26-7.33 (m, 6H, Ar—H); $^{13}$C NMR (300 MHz, CDCl$_3$) δ 23.7, 28.8, 29.4, 29.7, 30.3, 35.5, 38.5.3, 38.7, 42.0, 44.6, 115.7, 122.5, 126.3, 128.3, 140.6, 173.6; MS m/z (rel intensity) 382 (MH$^+$, 50).

Compound 7: Acetic acid 4-{[3-(4-chloro-phenyl)-adamantane-1-carbonyl]-amino}-phenyl ester. 140 mg, Yield=85%; m.p.: 176-178° C.; MS m/z (rel intensity) 424 (MH$^+$, 75), 425 (50), 426 (55).

Compound 8: 3-(4-Chloro-phenyl)-adamantane-1-carboxylic acid (2,4-dihydroxy-phenyl)-amide. 5 mg, Yield=4%; m.p.: 242-244° C.; MS m/z (rel intensity) 398 (MH$^+$, 20).

Compound 9: 3-(4-Chloro-phenyl)-adamantane-1-carboxylic acid (3-hydroxymethyl-phenyl)-amide. 74 mg, Yield=38%; m.p.: 173-175° C.; MS m/z (rel intensity) 396 (MH$^+$, 90).

Compound 10: Adamantane-1-carboxylic acid (4-cyanomethyl-phenyl)-amide. 5.1 mg, Yield=4%; m.p.: 184-186° C.; MS m/z (rel intensity) 295 (MH$^+$, 50).

Compound 11: 3-(4-Chloro-phenyl)-adamantane-1-carboxylic acid (4-cyanomethyl-phenyl)-amide. 92 mg, Yield=46%; mp: 157-159° C.; MS m/z (rel intensity) 405 (MH$^+$, 20).

Compound 12: 3-(4-Chloro-phenyl)-adamantane-1-carboxylic acid benzylamide. 144 mg, Yield=75.8%; m.p.: 134-136° C.; MS m/z (rel intensity) 380 (MH$^+$, 75).

Compound 13: 3-(4-Chloro-phenyl)-adamantane-1-carboxylic acid 4-tert-butyl-benzylamide. 35 mg, Yield=62%; m.p.: 187-189° C.; MS m/z (rel intensity) 436 (MH$^+$, 30).

Compound 14: 3-(4-Chloro-phenyl)-adamantane-1-carboxylic acid 4-methylsulfanyl-benzylamide. 100 mg, Yield=47%; m.p.: 139-141° C.; $^1$H NMR (300 MHz, CDCl$_3$) δ 1.73-1.98 (m, 12H, Admant-CH), 2.26 (s, 2H, Admant-CH), 2.47 (s, 3H, SCH$_3$), 4.38-4.40 (d, J=6 Hz, 2H, CH$_2$), 5.84 (s(br), 1H, HN), 7.16-7.24 (m, 4H, Ar—H), 7.26-7.30 (m, 4H, Ar—H); $^{13}$C NMR (300 MHz, CDCl$_3$) δ 15.9, 28.8, 35.5, 36.5, 38.4, 41.7, 42.0, 42.9, 44.6, 126.2, 126.7, 128.2, 131.4, 135.2, 137.5, 148.1, 177.2; MS m/z (rel intensity) 426.6 (MH$^+$, 100), 427.6 (30), 428.6 (32).

Compound 15: 3-(4-Chloro-phenyl)-adamantane-1-carboxylic acid 3-trifluoromethyl-benzylamide. 190 mg, Yield=81%; oil; $^1$H NMR (300 MHz, CDCl$_3$) δ 1.58-2.00 (m, 12H, Admant-CH), 2.28 (s, 2H, Admant-CH), 4.50-4.52 (d, J=6 Hz, 2H, CH$_2$), 6.02 (m, 1H, HN), 7.26-7.29 (m, 4H, Ar—H), 7.44-7.54 (m, 4H, Ar—H); $^{13}$C NMR (300 MHz, CDCl$_3$) δ 28.8, 35.5, 36.5, 38.5, 41.8, 42.0, 42.8, 44.5, 124.0, 126.2, 128.1, 129.0, 130.7, 139.9, 148.3, 177.2; MS m/z (rel intensity) 448.2 (MH$^+$, 100).

Compound 16: 3-(4-Chloro-phenyl)-adamantane-1-carboxylic acid 4-trifluoromethyl-benzylamide. 180 mg, Yield=80%; m.p.: 165-167° C.; $^1$H NMR (300 MHz, CDCl$_3$) δ 1.74-1.99 (m, 12H, Admant-CH), 2.28 (s, 2H, Admant-CH), 4.48-4.50 (d, J=6 Hz, 2H, CH$_2$), 6.03 (m, 1H, HN), 7.24-7.30 (m, 4H, Ar—H), 7.34-7.36 (d, J=6 Hz, 2H, Ar—H), 7.57-7.59 (d, J=6 Hz, 2H, Ar—H); $^{13}$C NMR (300 MHz, CDCl$_3$) δ 29.0, 35.7, 36.7, 38.3, 38.7, 42.2, 42.3, 43.1, 43.9, 44.8, 125.9, 126.6, 127.9, 128.5, 131.9, 142.9, 148.4, 177.8; MS m/z (rel intensity) 448.2 (MH$^+$, 100).

Compound 17: 3-(4-Chloro-phenyl)-adamantane-1-carboxylic acid 3,5-bis-trifluoromethyl-benzylamide. 168 mg, Yield=65%; m.p.: 125-127° C.; $^1$H NMR (300 MHz, CDCl$_3$) δ 1.75-2.00 (m, 12H, Admant-CH), 2.28 (s, 2H, Admant-CH), 4.53-4.55 (d, J=6 Hz, 2H, CH$_2$), 6.24 (m, 1H, HN), 7.23-7.30 (m, 4H, Ar—H), 7.69 (s, 2H, Ar—H), 7.77 (s, 1H, Ar—H); $^{13}$C NMR (300 MHz, CDCl$_3$) δ 28.9, 35.6, 36.7, 38.6, 42.0, 42.2, 42.6, 44.7, 121.5, 125.5, 126.5, 127.6, 128.5, 131.8, 141.8, 148.4, 178.1; MS m/z (rel intensity) 516.2 (MH$^+$, 100).

Compound 18: 3-(4-Chloro-phenyl)-adamantane-1-carboxylic acid 3-fluoro-5-trifluoromethyl-benzylamide. 210 mg, Yield=90%; m.p.: 92-94° C.; $^1$H NMR (300 MHz, CDCl$_3$) δ 1.75-2.00 (m, 12H, Admant-CH), 2.29 (s, 2H, Admant-CH), 4.48-4.50 (d, J=6 Hz, 2H, CH$_2$), 6.07 (m, 1H, HN), 7.14-7.29 (m, 7H, Ar—H); $^{13}$C NMR (300 MHz, CDCl$_3$) δ 28.9, 35.6, 36.6, 38.3, 38.7, 42.0, 42.1, 42.6, 44.7, 111.7, 112.0, 117.7, 118.0, 119.8, 126.5, 128.5, 131.8, 143.2, 148.4, 161.2, 164.5, 178.1; MS m/z (rel intensity) 466.2 (MH$^+$, 100).

Compound 19: 3-(4-Chloro-phenyl)-adamantane-1-carboxylic acid 2-fluoro-4-trifluoromethyl-benzylamide. 156 mg, Yield=67%; m.p.: 190-192° C.; $^1$H NMR (300 MHz, CDCl$_3$) δ 1.60-1.96 (m, 12H, Admant-CH), 2.28 (s, 2H, Admant-CH), 4.51-4.53 (d, J=6 Hz, 2H, CH$_2$), 6.08 (m, 1H, HN), 7.26-7.44 (m, 7H, Ar—H); $^{13}$C NMR (300 MHz, CDCl$_3$) δ 15.7, 29.0, 35.7, 36.7, 38.7, 42.2, 44.8, 113.3, 121.5, 126.6, 128.5, 130.8, 131.9, 148.4, 177.7; MS m/z (rel intensity) 466.1 (MH$^+$, 100).

Compound 20: 3-(4-Chloro-phenyl)-adamantane-1-carboxylic acid 3,5-difluoro-benzylamide. 160 mg, Yield=85%; m.p.: 59-61° C.; $^1$H NMR (300 MHz, CDCl$_3$) δ 1.75-2.03 (m, 12H, Admant-CH), 2.29 (s, 2H, Admant-CH), 4.38-4.41 (d, J=6 Hz, 2H, CH$_2$), 6.00 (m, 1H, HN), 6.67-6.81 (m, 3H, Ar—H), 7.29 (s, 4H, Ar—H); $^{13}$C NMR (300 MHz, CDCl$_3$) δ 28.9, 35.7, 36.7, 38.1, 38.7, 42.1, 42.3, 42.8, 44.1, 44.7, 103.0, 110.2, 126.6, 128.5, 131.9, 148.4, 164.9, 178.0; MS m/z (rel intensity) 416.59 (MH$^+$, 100), 417.59 (35), 418.59 (40), 419.60 (20).

Compound 21: 3-(4-Chloro-phenyl)-adamantane-1-carboxylic acid 3,4-difluoro-benzylamide. 179 mg, Yield=86%; m.p.: 100-102° C.; $^1$H NMR (300 MHz, CDCl$_3$) δ 1.74-1.98 (m, 12H, Admant-CH), 2.28 (s, 2H, Admant-CH), 4.38-4.41 (d, J=6 Hz, 2H, CH$_2$), 5.96 (m, 1H, HN), 6.98 (s, 1H, Ar—H), 7.06-7.12 (m, 2H, Ar—H), 7.24-7.30 (m, 4H, Ar—H); $^{13}$C NMR (300 MHz, CDCl$_3$) δ 29.0, 35.7, 36.7, 38.7, 42.0, 42.1, 42.7, 44.8, 116.7, 117.7, 123.7, 126.6, 128.5, 148.5, 177.8; MS m/z (rel intensity) 416.4 (MH$^+$, 100).

Compound 22: 3-(4-Chloro-phenyl)-adamantane-1-carboxylic acid 3,4,5-trifluoro-benzylamide. 195 mg, Yield=90%; m.p.: 106-108° C.; $^1$H NMR (300 MHz, CDCl$_3$) δ 1.75-1.98 (m, 12H, Admant-CH), 2.29 (s, 2H, Admant-CH), 4.36-4.38 (d, J=6 Hz, 2H, CH$_2$), 6.03 (m, 1H, HN), 6.82-6.89 (t, J=7.5 Hz, 2H, Ar—H), 7.28 (s, 4H, Ar—H); $^{13}$C NMR (300 MHz, CDCl$_3$) δ 28.9, 35.6, 36.7, 38.7, 42.1, 42.4, 44.7, 111.3, 111.4, 111.5, 123.3, 125.5, 126.6, 128.5, 129.8, 131.8, 135.6, 148.4, 178.0; MS m/z (rel intensity) 434.5 (MH$^+$, 100).

Compound 23: 3-(4-Chloro-phenyl)-adamantane-1-carboxylic acid 3-chloro-4-fluoro-benzylamide. 143 mg, Yield=66.2%; m.p.: 112-114° C.; $^1$H NMR (300 MHz, CDCl$_3$) δ 1.74-1.98 (m, 12H, Admant-CH), 2.28 (s, 2H, Admant-CH), 4.37-4.39 (d, J=6 Hz, 2H, CH$_2$), 5.99 (m, 1H, HN), 7.08 (s, 1H, Ar—H), 7.10-7.12 (m, 1H, Ar—H), 7.28-7.30 (m, 5H, Ar—H); $^{13}$C NMR (300 MHz, CDCl$_3$) δ 28.8, 35.5, 36.5, 38.5, 41.8, 42.0, 42.3, 44.6, 116.8, 126.2, 127.2, 128.2, 129.6, 148.0, 177.2; MS m/z (rel intensity) 432.5 (MH$^+$, 50).

Compound 24: 3-(4-Chloro-phenyl)-adamantane-1-carboxylic acid 4-fluoro-3-trifluoromethyl-benzylamide. 220 mg, Yield=94%; m.p.: 111-113° C.; $^1$H NMR (300 MHz, CDCl$_3$) δ 1.72-1.96 (m, 12H, Admant-CH), 2.25 (s, 2H, Admant-CH), 4.39-4.41 (d, J=6 Hz, 2H, CH$_2$), 6.31-6.34 (m, 1H, HN), 7.03-7.22 (m, 2H, Ar—H), 7.25-7.29 (m, 3H, Ar—H), 7.38-7.45 (m, 2H, Ar—H); $^{13}$C NMR (300 MHz, CDCl$_3$) δ 28.8, 35.5, 36.7, 37.7, 38.6, 38.7, 42.1, 42.3, 43.2, 44.7, 117.3, 126.2, 126.5, 128.5, 133.2, 148.4, 177.8; MS m/z (rel intensity) 466.6 (MH$^+$, 100).

Compound 25: 3-(4-Chloro-phenyl)-adamantane-1-carboxylic acid 2-chloro-4-fluoro-benzylamide. 145 mg, Yield=97.3%; m.p.: 132-134° C.; $^1$H NMR (300 MHz, CDCl$_3$) δ 1.72-2.03 (m, 12H, Admant-CH), 2.25 (s, 2H, Admant-CH), 4.45-4.47 (d, J=6 Hz, 2H, CH$_2$), 6.23 (m, 1H, HN), 6.90-6.96 (m, 1H, Ar—H), 7.08-7.18 (m, 2H, Ar—H), 7.26-7.33 (m, 4H, Ar—H); $^{13}$C NMR (300 MHz, CDCl$_3$) δ 29.0, 35.7, 36.7, 38.4, 38.6, 41.2, 42.2, 42.4, 44.7, 114.4, 117.0, 126.6, 128.5, 131.5, 148.5, 163.7, 177.7; MS m/z (rel intensity) 432.54 (MH$^+$, 100), 433.55 (25), 434.54 (80), 435.54 (30), 436.64 (25).

Compound 26: 3-(4-Chloro-phenyl)-adamantane-1-carboxylic acid 4-chloro-3-trifluoromethyl-benzylamide. 136 mg, Yield=92.0%; m.p.: 77-79° C.; $^1$H NMR (300 MHz, CDCl$_3$) δ 1.58-1.99 (m, 12H, Admant-CH), 2.29 (s, 2H, Admant-CH), 4.45-4.47 (d, J=6 Hz, 2H, CH$_2$), 6.05 (m, 1H, HN), 7.26-7.31 (m, 4H, H-Ph), 7.36-7.39 (d, J=9 Hz, 1H, Ar—H), 7.44-7.47 (d, J=9 Hz, 1H, Ar—H), 7.66 (s, 1H, Ar—H); $^{13}$C NMR (300 MHz, CDCl$_3$) δ 28.7, 35.5, 36.5, 38.5, 41.9, 42.3, 44.6, 126.2, 126.4, 128.3, 131.6, 131.8, 137.8, 148.0, 177.3; MS m/z (rel intensity) 482.55 (MH$^+$, 100), 483.55 (35), 484.35 (70).

Compound 27: 3-(4-Chloro-phenyl)-adamantane-1-carboxylic acid 3-aminomethyl-2,4,5,6-tetrachloro-benzylamide. 70 mg, Yield=31%; m.p.: 170-172° C.; $^1$H NMR (300 MHz, CDCl$_3$) δ 1.60 (s, 2H, NH$_2$), 1.72-1.94 (m, 12H, Admant-CH), 2.25 (s, 2H, Admant-CH), 4.19 (s, 2H, CH$_2$), 4.79-4.81 (d, J=6 Hz, 2H, CH$_2$), 5.91 (m(br), 1H, HN), 7.26-7.27 (m, 4H, Ar—H); $^{13}$C NMR (300 MHz, CDCl$_3$) δ 28.7, 35.5, 36.4, 38.4, 40.9, 41.9, 43.7, 44.5, 122.9, 125.2, 125.9, 126.2, 128.1, 129.3, 131.4, 131.8, 134.1, 134.3, 139.2, 148.0, 176.6; MS m/z (rel intensity) 546.9 (MH$^+$, 100).

Compound 28: 3-(4-Chloro-phenyl)-adamantane-1-carboxylic acid [1-(4-chloro-phenyl)-ethyl]-amide. 113 mg, Yield=53%; m.p.: 204-206° C. (B); $^1$H NMR (300 MHz, CDCl$_3$) δ 1.44-1.46 (d, J=6 Hz, 3H, CH$_3$), 1.58-1.94 (m, 12H, Admant-CH), 2.27 (s, 2H, Admant-CH), 5.06-5.11 (m, 1H, CH), 5.75-5.78 (m(br), 1H, HN), 7.20-7.31 (m, 8H, Ar—H); $^{13}$C NMR (300 MHz, CDCl$_3$) δ 22.0, 29.0, 35.7, 36.7, 38.6, 38.7, 41.8, 42.2, 44.8, 48.1, 126.3, 126.6, 127.7, 128.5, 129.0, 131.8, 133.2, 142.3, 148.5, 176.6; MS m/z (rel intensity) 428.4 (MH$^+$, 100).

Compound 29: 3-(4-Chloro-phenyl)-adamantane-1-carboxylic acid [1-(4-bromo-phenyl)-ethyl]-amide. 69 mg, Yield=29%; m.p.: 218-220° C.; MS m/z (rel intensity) 472 (MH$^+$, 80), 474 (MH$^+$, 100);

Compound 30: 3-(4-Chloro-phenyl)-adamantane-1-carboxylic acid 4-methanesulfonyl-benzylamide. 189 mg, Yield=82%; m.p.: 115-117° C.; $^1$H NMR (300 MHz, CDCl$_3$) δ 1.75-2.00 (m, 12H, Admant-CH), 2.29 (s, 2H, Admant-CH), 3.02 (s, 3H, CH$_3$), 4.51-4.53 (d, J=6 Hz, 2H, CH$_2$), 6.19 (m, 1H, HN), 7.16-7.28 (m, 4H, Ar—H), 7.40-7.43 (d, J=9 Hz, 2H, Ar—H), 7.84-7.87 (d, J=9 Hz, 2H, Ar—H); $^{13}$C NMR (300 MHz, CDCl$_3$) δ 29.0, 35.5, 35.7, 36.7, 37.7, 38.5, 38.7, 42.0, 42.2, 44.6, 44.7, 117.7, 125.6, 126.6, 127.7, 128.1, 129.9, 131.7, 137.4, 139.1, 145.9, 148.6, 178.0; MS m/z (rel intensity) 458.3 (MH$^+$, 100).

Compound 31: 3-(4-Chloro-phenyl)-adamantane-1-carboxylic acid 4-dimethylamino-benzylamide. 161 mg, Yield=76.1%; m.p.: 154-156° C.; $^1$H NMR (300 MHz, CDCl$_3$) δ 1.72-1.97 (m, 12H, Admant-CH), 2.36 (s, 2H, Admant-CH), 2.94 (s, 6H, N(CH$_3$)$_2$), 4.32-4.34 (d, J=6 Hz, 2H, CH$_2$), 5.73 (m, 1H, HN), 6.68-6.71 (d, J=9 Hz, 2H, Ar—H), 7.13-7.16 (d, J=9 Hz, 2H, Ar—H), 7.28 (s, 4H, Ar—H); $^{13}$C NMR (300 MHz, CDCl$_3$) δ 15.7, 29.0, 35.8, 38.7, 40.9, 42.3, 43.4, 44.8, 112.9, 126.6, 128.5, 129.2, 137.7, 140.9, 173.4; MS m/z (rel intensity) 422.66 (M$^+$, 100), 423.66 (MH$^+$, 90), 424.64 (60).

Compound 32: 3-(4-Chloro-phenyl)-adamantane-1-carboxylic acid 4-trifluoromethoxy-benzylamide. 200 mg, Yield=86.2%; m.p.: 119-121° C.; $^1$H NMR (300 MHz, CDCl$_3$) δ 1.72-2.02 (m, 12H, Admant-CH), 2.24 (s, 2H, Admant-CH), 4.39-4.41 (d, J=6 Hz, 2H, CH$_2$), 6.27 (s, 1H, HN), 7.06-7.26 (m, 8H, Ar—H); $^{13}$C NMR (300 MHz, CDCl$_3$) δ 29.0, 35.7, 35.8, 36.7, 38.4, 38.7, 42.1, 42.4, 42.8, 43.6, 44.8, 121.2, 121.6, 126.3, 126.6, 128.5, 128.7, 129.1, 137.5, 148.4, 177.9; MS m/z (rel intensity) 464.4 (MH$^+$, 70).

Compound 33: 3-(4-Chloro-phenyl)-adamantane-1-carboxylic acid 3-trifluoromethoxy-benzylamide. 200 mg, Yield=86%; oil; $^1$H NMR (300 MHz, CDCl$_3$) δ 1.75-2.00 (m, 12H, Admant-CH), 2.28 (s, 2H, Admant-CH), 4.45-4.47 (d, J=6 Hz, 2H, CH$_2$), 6.00 (m, 1H, HN), 7.01-7.19 (m, 3H, Ar—H), 7.24-7.38 (m, 5H, Ar—H); $^{13}$C NMR (300 MHz, CDCl$_3$) δ 29.0, 35.7, 36.7, 38.7, 42.0, 42.2, 42.8, 44.8, 119.8, 125.9, 126.6, 128.5, 130.2, 131.8, 141.5, 148.6, 149.7, 177.8; MS m/z (rel intensity) 464.2 (MH$^+$, 100).

Compound 34: 3-(4-Chloro-phenyl)-adamantane-1-carboxylic acid 4-phenoxy-benzylamide. 170 mg, Yield=72.0%; m.p.: 121-123° C.; $^1$H NMR (300 MHz, CDCl$_3$) δ 1.58-1.99 (m, 12H, Admant-CH), 2.27 (s, 2H, Admant-CH), 4.41-4.43 (d, J=6 Hz, 2H, CH$_2$), 5.88 (m, 1H, HN), 6.95-7.02 (m, 3H, Ar—H), 7.09-7.14 (m, 1H, Ar—H), 7.20-7.36 (m, 9H, Ar—H); $^{13}$C NMR (300 MHz, CDCl$_3$) δ 28.8, 35.6, 36.5, 38.5, 42.0, 42.9, 43.9, 44.6, 118.8, 118.9, 123.3, 128.2, 129.0, 129.6, 131.4, 133.1, 148.1, 156.5, 156.9, 176.9; MS m/z (rel intensity) 472.36 (MH$^+$, 100), 473.36 (30), 474.37 (30).

Compound 35: Adamantane-1-carboxylic acid 3,4-dihydroxy-benzylamide. 143 mg, Yield=48%; m.p.: 184-186° C.; MS m/z (rel intensity) 302 (MH$^+$, 8).

Compound 36: 3-(4-Chloro-phenyl)-adamantane-1-carboxylic acid 3,4-dihydroxy-benzylamide. 134 mg, Yield=65%; m.p.: 73-75° C.; MS m/z (rel intensity) 412 (MH$^+$, 10).

Compound 37: 3-(4-Chloro-phenyl)-adamantane-1-carboxylic acid phenethyl-amide. 150 mg, Yield=76%; m.p.: 123-125° C.; MS m/z (rel intensity) 394 (MH$^+$, 14).

Compound 38: 3-(4-Chloro-phenyl)-adamantane-1-carboxylic acid [2-(4-fluoro-phenyl)-ethyl]-amide. 156 mg, Yield=78%; m.p.: 103-105° C.; MS m/z (rel intensity) 412 (MH$^+$, 52), 413(17), 414 (20).

Compound 39: 3-(4-Chloro-phenyl)-adamantane-1-carboxylic acid [2-(4-bromo-phenyl)-ethyl]-amide. 30 mg, Yield=55%; m.p.: 114-116° C.; MS m/z (rel intensity) 472 (MH$^+$, 38), 474 (MH$^+$, 42);

Compound 40: 3-(4-Chloro-phenyl)-adamantane-1-carboxylic acid [2-(4-hydroxy-phenyl)-ethyl]-amide. 112 mg, Yield=55%; m.p.: 174-176° C.; MS m/z (rel intensity) 410 (MH$^+$, 100), 411(25), 412 (33).

Compound 41: 3-(4-Chloro-phenyl)-adamantane-1-carboxylic acid [2-(4-methoxy-phenyl)-ethyl]-amide. 159 mg, Yield=75%; m.p.: 108-110° C.; MS m/z (rel intensity) 424 (MH$^+$, 55), 425(18), 426 (20).

Compound 42: 3-(4-Chloro-phenyl)-adamantane-1-carboxylic acid [2-(3-bromo-4-methoxy-phenyl)-ethyl]-amide. 220 mg, Yield=87.5%; oil; $^1$H NMR (300 MHz, CDCl$_3$) δ 1.63-1.89 (m, 12H, Admant-CH), 2.25 (s, 2H, Admant-CH), 2.71-2.76 (t, J=7.5 Hz, 2H, CH$_2$), 3.42-3.48 (q, J=12 Hz, 2H, NCH$_2$), 3.87 (s, 3H, OCH$_3$), 5.62 (s(br), 1H, NH), 6.82-6.84 (d, J=6 Hz, 1H, Ar—H), 7.07-7.09 (d, J=6 Hz, 1H, Ar—H), 7.27-7.30 (m, 4H, Ar—H), 7.36 (s, 1H, Ar—H); $^{13}$C NMR (300 MHz, CDCl$_3$) δ 29.0, 34.6, 35.7, 36.7, 38.6, 40.8, 41.9, 42.2, 44.8, 56.5, 112.3, 111.7, 126.6, 128.5, 128.6, 129.0, 132.8, 133.9, 148.6, 154.7, 177.6; MS m/z (rel intensity) 502 (MH$^+$, 80), 503 (25), 504 (MH$^+$, 100), 505 (33);

Compound 43: Adamantane-1-carboxylic acid [2-(3,4-dihydroxy-phenyl)-ethyl]-amide. 69 mg, Yield=24%; mp: 98-100° C.; $^1$H NMR (300 MHz, DMSO-d$_6$) δ 0.94-0.98 (m, 2H, CH$_2$), 1.60-1.95 (m, 15H, Admant-CH), 3.12-3.15 (m, 2H, CH$_2$), 6.39-6.41 (d, J=6 Hz, 1H, Ar—H), 6.54 (s, 1H, Ar—H), 6.60-6.62 (d, J=6 Hz, 1H, Ar—H), 7.35 (s, 1H, NH); $^{13}$C NMR (300 MHz, DMSO-d$_6$) δ 27.6, 29.4, 35.1, 36.9, 37.8, 38.6, 44.6, 46.4, 114.8, 116.9, 119.4, 131.4, 145.6, 164.4; MS m/z (rel intensity) 316.5 (MH$^+$, 50), 317.5 (8).

Compound 44: 3-(4-Chloro-phenyl)-adamantane-1-carboxylic acid [2-(3,4-dihydroxy-phenyl)-ethyl]-amide. 100 mg, Yield=47.0%; m.p.: 124-126° C.; MS m/z (rel intensity) 426 (MH$^+$, 100).

Compound 45: 3-(4-Chloro-phenyl)-adamantane-1-carboxylic acid (2-benzo[1,3]dioxol-5-yl-ethyl)-amide. 190 mg, Yield=87%; oil; $^1$H NMR (300 MHz, CDCl$_3$) δ 1.71-1.90 (m, 12H, Admant-CH), 2.24 (s, 2H, Admant-CH), 2.70-2.75 (t, J=6 Hz, 2H, CH$_2$), 3.42-3.48 (q, J=6 Hz, 2H, CH$_2$), 5.61 (m, 1H, NH), 5.93 (s, 2H, CH$_2$), 6.60-6.63 (d, J=9 Hz, 1H, Ar—H), 6.67 (s, 1H, Ar—H), 6.73-6.76 (d, J=9 Hz, 1H, Ar—H), 7.26-7.29 (m, 4H, Ar—H); $^{13}$C NMR (300 MHz, CDCl$_3$) δ 28.6, 28.8, 35.4, 35.5, 36.4, 38.3, 40.6, 41.6, 42.0, 43.8, 44.5, 100.8, 108.2, 109.0, 121.5, 126.2, 128.1, 132.5, 146.0, 148.2, 177.0; MS m/z (rel intensity) 438.28 (MH$^+$, 100), 439.29 (45), 440.28 (55).

Compound 46: 3-(4-Chloro-phenyl)-adamantane-1-carboxylic acid [2-(3-phenoxy-phenyl)-ethyl]-amide. 200 mg, Yield=82%; m.p.: 114-116° C.; $^1$H NMR (300 MHz, CDCl$_3$) δ 1.70-1.95 (m, 12H, Admant-CH), 2.23 (s, 2H, Admant-CH), 2.75-2.80 (t, J=7.5 Hz, 2H, CH$_2$), 3.45-3.51 (q, J=12 Hz, 2H, NCH$_2$), 5.63 (s(br), 1H, NH), 6.83-7.01 (m, 5H, Ar—H), 7.07-7.18 (m, 2H, Ar—H), 7.22-7.35 (m, 6H, Ar—H); $^{13}$C NMR (300 MHz, CDCl$_3$) δ 28.8, 29.0, 35.8, 36.7, 38.6, 40.7, 41.9, 42.3, 44.8, 116.9, 117.1, 119.2, 119.4, 123.5, 123.6, 123.9, 126.6, 128.5, 130.0, 130.2, 141.7, 148.3, 157.4, 177.7; MS m/z (rel intensity) 486.58 (MH$^+$, 93), 487.56 (60), 488.55 (68), 489.54 (25).

Compound 47: 3-(4-Chloro-phenyl)-adamantane-1-carboxylic acid [2-(4-phenoxy-phenyl)-ethyl]-amide. 224 mg, Yield=92%; m.p.: 88-90° C.; $^1$H NMR (300 MHz, CDCl$_3$) δ 1.71-1.90 (m, 12H, Admant-CH), 2.24 (s, 2H, Admant-CH), 2.77-2.81 (t, J=6 Hz, 2H, CH$_2$), 3.48-3.51 (m, 2H, NCH$_2$), 5.63 (s(br), 1H, NH), 6.94-7.00 (m, 4H, Ar—H), 7.09-7.35 (m, 9H, Ar—H); $^{13}$C NMR (300 MHz, CDCl$_3$) δ 29.1, 29.3, 35.2, 35.8, 36.7, 38.7, 40.9, 41.9, 42.3, 44.8, 118.9, 119.4, 123.5, 126.6, 128.6, 129.3, 130.0, 130.4, 131.8, 134.2, 148.7, 156.1, 157.6, 177.5; MS m/z (rel intensity) 486.58 (MH$^+$, 93), 487.56 (60), 488.55 (68), 489.54 (25).

Compound 48: 3-(4-Chloro-phenyl)-adamantane-1-carboxylic acid (3-phenyl-propyl)-amide. 195 mg, Yield=59%; m.p.: 97-100° C.; MS m/z (rel intensity) 408 (MH$^+$, 55).

Compound 49: 3-(4-Chloro-phenyl)-adamantane-1-carboxylic acid (biphenyl-4-ylmethyl)-amide. 200 mg, Yield=87.7%; m.p.: 208-210° C.; $^1$H NMR (300 MHz, CDCl$_3$) δ 1.74-2.09 (m, 12H, Admant-CH), 2.26 (s, 2H, Admant-CH), 4.48-4.50 (d, J=6 Hz, 2H, CH$_2$), 5.94 (m, 1H, HN), 7.29-7.37 (m, 6H, Ar—H), 7.42-7.46 (m, 3H, Ar—H), 7.55-7.59 (m, 4H, Ar—H); $^{13}$C NMR (300 MHz, CDCl$_3$) δ 15.7, 29.0, 35.8, 36.7, 38.8, 42.0, 42.3, 43.4, 44.9, 126.6, 127.3, 127.6, 127.7, 128.4, 128.5, 129.0, 137.7, 140.9, 148.5, 177.4; MS m/z (rel intensity) 456.59 (MH$^+$, 90), 457.57 (20), 458.56 (30).

Compound 50: Adamantane-1-carboxylic acid (1-methyl-piperidin-4-yl)-amide. 120 mg, Yield=76%; m.p.: 157-159° C.; MS m/z (rel intensity) 277 (MH$^+$, 100).

Compound 51: 3-(4-Chloro-phenyl)-adamantane-1-carboxylic acid (1-methyl-piperidin-4-yl)-amide. 136 mg, Yield=74.4%; m.p.: 146-148° C.; $^1$H NMR (300 MHz, CDCl$_3$) δ 1.06-2.77 (m 25H, Admant-CH,

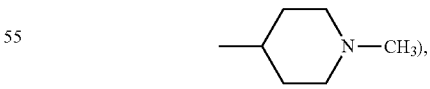

4.44-3.70 (m, 1H, CH), 5.41-5.43 (m, 1H, HN), 7.26-7.29 (m, 4H, H—Ar); $^{13}$C NMR (300 MHz, CDCl$_3$) δ 11.6, 29.1, 32.5, 35.8, 36.7, 38.6, 41.9, 42.2, 44.8, 46.0, 46.4, 54.7, 126.6, 128.5, 131.8, 148.6, 176.8; MS m/z (rel intensity) 387 (MH$^+$, 100).

Compound 52: 3-(4-Chloro-phenyl)-adamantane-1-carboxylic acid (4-methyl-piperazin-1-yl)-amide. 182 mg, Yield=66.2%; m.p.: 142-147° C.; MS m/z (rel intensity) 387 (MH$^+$, 48).

Compound 53: 3-(4-Chloro-phenyl)-adamantane-1-carboxylic acid (3-tert-butylamino-propyl)-amide. 160 mg, Yield=79%; oil; $^1$H NMR (300 MHz, CDCl$_3$) δ 1.11 (s, 9H, 3CH$_3$), 1.69-1.95 (m, 14H, Admant-CH, CH$_2$), 2.18 (m, 1H, HN), 2.25 (s, 2H, Admant-CH), 2.70-2.74 (t, J=6 Hz, 2H, CH$_2$), 3.33-3.38 (m, 2H, CH$_2$), 7.16-7.27 (m, 4H, Ar—H), 7.42 (m, 1H, HN); $^{13}$C NMR (300 MHz, CDCl$_3$) δ 28.5, 28.7, 29.1, 29.4, 35.9, 36.7, 38.8, 39.3, 39.7, 41.1, 41.8, 42.3, 42.6, 45.0, 46.0, 51.8, 126.3, 128.3, 128.4, 148.8, 177.8; MS m/z (rel intensity) 403.1 (MH$^+$, 100).

Compound 54: 3-(4-Chloro-phenyl)-adamantane-1-carboxylic acid (3-pyrrolidin-1-yl-propyl)-amide. 184 mg, Yield=92%; m.p.: 86-88° C.; $^1$H NMR (300 MHz, CDCl$_3$) δ 1.63-1.92 (m, 18H, Admant-CH, CH$_2$), 2.24 (s, 2H, Admant-CH), 2.50 (s, 4H, CH$_2$), 2.58-2.62 (t, J=6 Hz, 2H, CH$_2$), 3.33-3.38 (m, 2H, CH$_2$), 7.19-7.28 (m, 4H, Ar—H), 7.92 (m, 1H, HN); $^{13}$C NMR (300 MHz, CDCl$_3$) δ 23.7, 26.5, 29.1, 35.9, 36.7, 38.7, 40.7, 41.7, 42.3, 44.9, 54.4, 56.4, 126.6, 128.4, 129.6, 131.6, 148.8, 177.6; MS m/z (rel intensity) 401.25 (MH$^+$, 100).

Compound 55: 3-(4-Chloro-phenyl)-adamantane-1-carboxylic acid [3-(2-oxo-pyrrolidin-1-yl)-propyl]-amide. 190 mg, Yield=98%; oil; $^1$H NMR (300 MHz, CDCl$_3$) δ 1.60-2.12 (m, 16H, cyclo-CH$_2$, Admant-CH), 2.27 (s, 2H, Admant-CH), 2.36-2.47 (t, J=7.5 Hz, 2H, cyclo-CH$_2$), 3.15-3.20 (t, J=7.5 Hz, 2H, CH$_2$), 3.32-3.42 (m, 4H, CH$_2$), 7.09 (m, 1H, HN), 7.18-7.32 (m, 4H, Ar—H); $^{13}$C NMR (300 MHz, CDCl$_3$) δ 18.2, 26.5, 29.1, 31.1, 35.0, 35.9, 36.7, 38.5, 39.5, 42.0, 42.4, 44.8, 47.6, 126.7, 128.4, 166.5, 177.9; MS m/z (rel intensity) 415.6 (MH$^+$, 100).

Compound 56: Adamantane-1-carboxylic acid [2-(1-methyl-pyrrolidin-2-yl)-ethyl]-amide. 23 mg, Yield=33%; m.p.: 82-84° C.; MS m/z (rel intensity) 291 (MH$^+$, 100).

Compound 57: 3-(4-Chloro-phenyl)-adamantane-1-carboxylic acid [2-(1-methyl-pyrrolidin-2-yl)-ethyl]-amide. 200 mg, Yield=61.7%; Oil; $^1$H NMR (300 MHz, CDCl$_3$) δ 1.68-2.36 (m, 24H, Admant-CH,

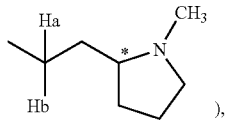

2.98-3.04 (m, 1H, CH*), 3.17-3.27 (m, 1H, Ha), 3.45-3.53 (m, 1H, Hb), 7.24-7.30 (m, 4H, H—Ar); $^{13}$C NMR (300 MHz, CDCl$_3$) δ 22.9, 28.6, 29.1, 29.5, 35.9, 36.7, 38.6, 40.9, 41.7, 42.4, 44.7, 57.3, 65.0, 126.5, 128.4, 131.6, 148.8, 177.4; MS m/z (rel intensity) 401 (MH$^+$, 100). HCL salt: m.p.: 68-70° C.

Compound 58: 3-(4-Chloro-phenyl)-adamantane-1-carboxylic acid (2-morpholin-4-yl-ethyl)-amide. 147 mg, Yield=73%; m.p.: 110-112° C.; MS m/z (rel intensity) 403 (MH$^+$, 100).

Compound 59: 3-(4-Chloro-phenyl)-adamantane-1-carboxylic acid (2-piperazin-1-yl-ethyl)-amide. 144 mg, Yield=72%, oil; $^1$H NMR (300 MHz, CDCl$_3$) δ 1.65-1.97 (m, 15H, NH, cyclo-CH$_2$, Admant-CH), 2.27 (s, 2H, Admant-CH), 2.36-2.50 (m, 6H, cyclo-CH$_2$), 2.87-2.90 (m, 2H, CH$_2$), 3.30-3.95 (m, 2H, CH$_2$), 6.34 (m, 1H, HN), 7.18-7.29 (m, 4H, Ar—H); $^{13}$C NMR (300 MHz, CDCl$_3$) δ 28.8, 35.6, 36.4, 38.4, 41.6, 42.1, 44.5, 46.2, 52.7, 54.1, 56.8, 126.3, 128.2, 148.4, 156.2, 177.3; MS m/z (rel intensity) 402.6 (MH$^+$, 100).

Compound 60: Adamantane-1-carboxylic acid (pyridin-4-yl-methyl)-amide. 200 mg, Yield=74%; m.p.: 155-157° C.; MS m/z (rel intensity) 285.63 (MH$^+$, 100), 286.71 (40).

Compound 61: 3-(4-Fluoro-phenyl)-adamantane-1-carboxylic acid (pyridin-4-ylmethyl)-amide. 105 mg, Yield=97%; oil; MS m/z (rel intensity) 365 (MH$^+$, 90).

Compound 62: 3-(4-Chloro-phenyl)-adamantane-1-carboxylic acid (pyridin-4-ylmethyl)-amide. Yield=92.6%; m.p.: 128-130° C.; $^1$H NMR (300 MHz, CDCl$_3$) δ 1.72-2.25 (m, 12H, Admant-CH), 4.44-4.46 (d, J=6 Hz, 2H, CH$_2$-Py), 6.18 (m, 1H, HN), 7.13-7.15 (d, J=6 Hz, 2H, H-Py), 7.15-7.30 (m, 4H, H-Ph), 8.52-8.54 (d, J=6 Hz, 2H, H-Py); $^{13}$C NMR (300 MHz, CDCl$_3$) δ 28.98, 35.73, 36.71, 38.77, 42.18, 42.37, 44.88, 122.38, 125.30, 126.57, 128.56, 129.26, 148.39, 150.20 177.76; MS m/z (rel intensity) 381.50 (MH$^+$, 100), 383.41 (90), 384.35 (80).

Compound 63: Adamantane-1-carboxylic acid (2-pyridin-4-yl-ethyl)-amide. 175 mg, Yield=61%; m.p.: 151-153° C.; MS m/z (rel intensity) 285 (MH$^+$, 100).

Compound 64: 3-(4-Chloro-phenyl)-adamantane-1-carboxylic acid (2-pyridin-4-yl-ethyl)-amide. 70 mg, Yield=55.7%; m.p.: 144-147° C.; MS m/z (rel intensity) 395 (MH$^+$, 100).

Compound 65: 3-(4-Chloro-phenyl)-adamantane-1-carboxylic acid (3-imidazol-1-yl-propyl)-amide. 195 mg, Yield=95%; m.p.: 128-130° C.; $^1$H NMR (300 MHz, CDCl$_3$) δ 1.70-2.00 (m, 14H, CH$_2$, Admant-CH), 2.27 (s, 2H, Admant-CH), 3.25-3.32 (m, 2H, CH$_2$), 3.96-4.00 (m, 2H, CH$_2$), 5.65 (m, 1H, HN), 6.95 (s, 1H, imdazol-H), 7.07 (s, 1H, imidazol-H), 7.26-7.28 (m, 4H, Ar—H), 7.49 (s, 1H, imidazol-H); $^{13}$C NMR (300 MHz, CDCl$_3$) δ 29.0, 31.5, 35.7, 36.7, 37.0, 38.6, 41.9, 42.2, 44.8, 45.0, 119.1, 126.3, 126.6, 128.5, 129.8, 131.8, 137.3, 148.5, 178.0; MS m/z (rel intensity) 398.66 (MH$^+$, 100), 399.62 (45), 400.63 (60), 401.60 (20).

Compound 66: 3-(4-Chloro-phenyl)-adamantane-1-carboxylic acid (2-methyl-1H-indol-5-yl)-amide. Yield=56%; m.p.: 145-147° C.; MS m/z (rel intensity) 419 (MH$^+$, 35).

Compound 67: 3-(4-Chloro-phenyl)-adamantane-1-carboxylic acid (1H-tetrazol-5-yl)-amide. 120 mg, Yield=67%; m.p.: >240° C.; MS m/z (rel intensity) 358.2 (MH$^+$, 100), 359.1 (35), 361.1 (60).

Compound 68: 3-(4-Chloro-phenyl)-adamantane-1-carboxylic acid (9-ethyl-9H-carbazol-3-yl)-amide. 111 mg, Yield=46%; m.p.: 165-167° C.; MS m/z (rel intensity) 482.67 (MH$^+$, 100), 483.67 (65), 484.66 (55).

Compound 69: Adamantane-1-carboxylic acid [4-(4-chloro-phenyl)-thiazol-2-yl]-amide. 182 mg, Yield=49%; m.p.: 162-164° C.; MS m/z (rel intensity) 373 (MH$^+$, 100).

Compound 70: 3-(4-Chloro-phenyl)-adamantane-1-carboxylic acid [4-(4-chloro-phenyl)-thiazol-2-yl]-amide. Yield=56%; m.p.: 172-174° C.; MS m/z (rel intensity) 483 (MH$^+$, 20).

Compound 71: 3-(4-Chloro-phenyl)-adamantane-1-carboxylic acid benzothiazol-2-ylamide. Yield=48.8%; m.p.: 209-211° C.; MS m/z (rel intensity) 423 (MH$^+$, 50).

Compound 72: 3-(4-Chloro-phenyl)-adamantane-1-carboxylic acid (5-chloro-benzooxazol-2-yl)-amide. Yield=45%; oil; MS m/z (rel intensity) 441 (MH$^+$, 18).

Compound 73: 3-(4-Chloro-phenyl)-adamantane-1-carboxylic acid (9H-purin-6-yl)-amide. 180 mg, Yield=88.2%; oil; $^1$H NMR (300 MHz, CDCl$_3$) δ 1.84-2.21 (m, 13H, NH, Admant-CH), 2.38 (s, 2H, Admant-CH), 7.07 (s, 1H, Ar—H), 7.30 (m, 4H, Ar—H), 7.63 (s, 1H, Ar—H), 8.38 (s, 1H, Ar—H); $^{13}$C NMR (300 MHz, CDCl$_3$) δ 28.8, 35.5, 36.7, 37.7, 38.7, 42.1, 44.6, 45.1, 117.7, 123.2, 125.5, 126.5, 126.6, 128.7, 129.9, 130.1, 132.1, 137.4, 147.8, 174.3; MS m/z (rel intensity) 408.6 (MH$^+$, 100).

Example 4

Method for the Conversion of Adamantylamides into Adamantylamines

As an example, a process for the synthesis of adamantylamine compounds is described in Scheme 3. A number of adamantylamides, prepared as described above, were converted to their corresponding adamantylamines by reduction of the carbonyl group with $Zn(BH_4)_2$ (Scheme 3).

Zinc borohydride ($Zn(BH_4)_2$) was prepared by methods known in the art. Briefly, 20.8 g (165 mmol) of freshly fused $ZnCl_2$ and 12.9 g (330 mmol) of $NaBH_4$ were placed in a dried 250 ml side arm flask fitted with a reflux condenser. To this, 250 ml of dry THF was added using a double-ended needle, and the mixture was stirred for 24 h at room temperature. The active hydride content of the supernatant solution was estimating by quenching aliquots with 2N $H_2SO_4$ and estimating the amount of hydrogen that was evolved using a gas burette. The final supernatant solution contained 0.66 M $Zn(BH_4)_2$, and was used for further reactions as follows.

The general method for the conversion of adamantylamides into the corresponding adamantylamines involved combining 100 mg of an adamatanylamide with 2.0 ml of $Zn(BH_4)_2$ (0.36 M, 2.3 mmol) in THF. The mixture was refluxed for 24 h, and any excess hydride present was quenched by the addition of 1 ml of water. Typically, the mixture was then saturated with $K_2CO_3$ and the supernatant layer was filtered and dried over $K_2CO_3$, and the solvent was removed by evaporation. The residue was then purified by flash chromatography (ethyl acetate:hexane=1:4) to give the adamantylamine compound.

Scheme 3.

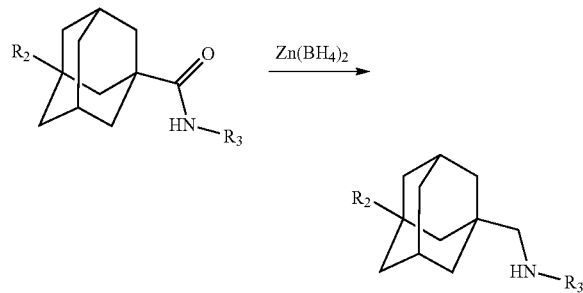

The following Example provides several representatives of the products of this process; however, these methods can be adapted to produce many structurally related adamantylamines that are considered to be subjects of this invention.

Example 5

Synthesis of Adamantylamines

The methods described in Example 4 were used to prepare a library of substituted adamantylamines Data provided below include: the amount synthesized, the yield of the reduction reaction; the melting point (m.p.) of the compound; mass spectral (MS) data for the compound; and NMR spectral data for the compound.

Compound 75: [3-(4-Chloro-phenyl)-adamantan-1-ylmethyl]-isopropyl-amine 39 mg, Yield=41%; oil; MS m/z (rel intensity) 318 ($MH^+$, 20).

Compound 76: 4-{[3-(4-Chloro-phenyl)-adamantan-1-ylmethyl]-amino}-phenol. 75 mg, Yield=66%; oil; $^1H$ NMR (300 MHz, $CDCl_3$) δ 1.60-1.86 (m, 12H, Admant-H), 2.22 (s, 2H, Admant-H), 2.58-2.62 (m, 1H, NH), 2.83 (s, 2H, $CH_2$), 6.53-6.56 (d, J=9 Hz, 2H, Ar—H), 6.68-6.71 (d, J=9 Hz, 2H, Ar—H), 7.28 (s, 4H, Ar—H); $^{13}C$ NMR (300 MHz, $CDCl_3$) δ 14.3, 29.0, 34.9, 36.1, 36.7, 39.9, 42.6, 46.3, 57.4, 114.1, 116.1, 126.3, 128.1, 131.2, 143.2, 147.3, 148.9; MS m/z (rel intensity) 368.6 ($MH^+$, 100), 369.6 (50), 370.6 (30).

Compound 77: [3-(4-Chloro-phenyl)-adamantan-1-ylmethyl]-(4-trifluoromethyl-benzyl)-amine 23 mg, Yield=28%; oil; $^1H$ NMR (300 MHz, $CDCl_3$) δ 1.55-1.83 (m, 13H, Admant-H, NH), 2.18 (s, 2H, Admant-H), 2.32 (s, 2H, $NCH_2$), 3.84 (s, 2H, $NCH_2$), 7.27 (s, 4H, Ar—H), 7.43-7.45 (d, J=6 Hz, 2H, Ar—H), 7.56-7.58 (d, J=6 Hz, 2H, Ar—H); $^{13}C$ NMR (300 MHz, $CDCl_3$) δ 29.1, 34.7, 36.3, 36.7, 40.0, 42.7, 46.5, 54.1, 61.7, 125.1, 126.3, 128.0, 131.1, 144.9, 149.1; MS m/z (rel intensity) 434.4 ($MH^+$, 60), 435.4 (25), 436.4 (30).

Compound 78: [3-(4-Chloro-phenyl)-adamantan-1-ylmethyl]-(2-fluoro-4-trifluoromethyl-benzyl)-amine 21 mg, Yield=24%; oil; $^1H$ NMR (300 MHz, $CDCl_3$) δ 1.55-1.83 (m, 12H, Admant-H), 2.20 (s, 2H, Admant-H), 2.32 (s, 2H, $CH_2$), 3.88 (s, 2H, Ar—$CH_2$), 7.26-7.27 (s, 4H, Ar—H), 7.29-7.31 (m, 2H, Ar—H), 7.49-7.53 (m, 2H, Ar—H); $^{13}C$ NMR (300 MHz, $CDCl_3$) δ 29.0, 34.6, 36.2, 36.7, 39.9, 42.7, 46.5, 47.6, 61.7, 112.4, 112.7, 120.8, 126.3, 128.0, 130.4, 131.8, 149.1; MS m/z (rel intensity) 452.7 ($MH^+$, 100), 453.7 (30), 454.7 (40).

Compound 79: [3-(4-Chloro-phenyl)-adamantan-1-ylmethyl]-(4-fluoro-3-trifluoromethyl-benzyl)-amine 24 mg, Yield=38%; oil; $^1H$ NMR (300 MHz, $CDCl_3$) δ 1.28-1.82 (m, 12H, Admant-H), 2.19 (s, 2H, Admant-H), 2.51-2.55 (m, 1H, $CH_2$), 2.88-2.90 (m, 1H, $CH_2$), 3.40 (s, 1H, NH), 3.76-3.80 (m, 1H, $CH_2$), 4.08-4.13 (m, 1H, $CH_2$), 7.14-7.29 (m, 5H, Ar—H), 7.57 (m, 2H, Ar—H); $^{13}C$ NMR (300 MHz, $CDCl_3$) δ 28.5, 34.3, 35.5, 36.4, 39.8, 41.9, 42.1, 46.3, 61.2, 66.7, 117.4, 117.7, 126.0, 128.2, 129.0, 130.5, 131.6, 135.9, 147.7, 158.1, 161.5; MS m/z (rel in ensity) 452.4 ($MH^+$, 100), 453.4 (50), 454.4 (60).

Compound 80: [3-(4-Chloro-phenyl)-adamantan-1-ylmethyl]-(4-trifluoromethoxy-benzyl)-amine 23 mg, Yield=36%; oil; $^1H$ NMR (300 MHz, $CDCl_3$) δ 1.28-1.80 (m, 12H, Admant-H), 2.15 (s, 2H, Admant-H), 2.53-2.57 (m, 1H, $NCH_2$), 2.84-2.90 (m, 1H, $NCH_2$), 3.38 (m, 1H, NH), 3.68-3.75 (m, 1H, $NCH_2$), 4.14-4.19 (m, 1H, $NCH_2$), 7.13-7.16 (d, J=9 Hz, 2H, Ar—H), 7.36-7.39 (d, J=9 Hz, 2H, Ar—H), 7.2-5-7.27 (m, 4H, Ar—H); $^{13}C$ NMR (300 MHz, $CDCl_3$) δ 28.5, 29.0, 34.6, 36.3, 39.7, 40.0, 42.7, 46.5, 53.9, 61.7, 66.2, 120.7, 121.2, 126.0, 126.3, 128.1, 129.0, 131.6, 132.9, 147.9; MS m/z (rel intensity) 450.6 ($MH^+$, 70), 451.6 (30), 452.6 (40).

Compound 81: [3-(4-Chloro-phenyl)-adamantan-1-ylmethyl]-[2-(3-phenoxy-phenyl)-ethyl]amine 27 mg, Yield=42%; oil; $^1H$ NMR (300 MHz, $CDCl_3$) δ 1.50-1.82 (m, 13H, Admant-CH, NH), 2.16 (s, 2H, Admant-CH), 2.34 (s, 2H, $CH_2$), 2.76-2.84 (m, 4H, $NCH_2$), 5.63 (s(br), 1H, NH), 6.83-7.01 (m, 5H, Ar—H), 7.07-7.18 (m, 2H, Ar—H), 7.22-7.35 (m, 6H, Ar—H); $^{13}C$ NMR (300 MHz, $CDCl_3$) δ 29.1, 34.6, 36.1, 36.7, 40.0, 42.7, 46.5, 52.1, 62.3, 116.4, 118.8, 119.1, 123.1, 123.6, 126.3, 128.0, 129.5, 142.2, 149.1, 157.1; MS m/z (rel intensity) 472.4 ($MH^+$, 100), 473.3 (70), 474.3 (80).

Compound 82: [3-(4-Chloro-phenyl)-adamantan-1-ylmethyl]-(1-methyl-piperidin-4-yl)-amine 12 mg, Yield=6%; oil; MS m/z (rel intensity) 373.6 ($MH^+$, 100), 374.6 (25), 375.6 (36).

Compound 83: [3-(4-Chloro-phenyl)-adamantan-1-ylmethyl]-(4-methyl-piperazin-1-yl)-amine Yield=12%; oil; $^1H$ NMR (300 MHz, $CDCl_3$) δ 1.54-1.82 (m, 12H, Admant-H), 2.17 (s, 2H, Admant-H), 2.52 (s, 2H, $CH_2$), 2.63 (s, 3H, $NCH_3$), 2.77-2.80 (m, 4H, $NCH_2$), 2.98-3.15 (m, 4H, $NCH_2$), 7.28 (s, 4H, Ar—H); $^{13}C$ NMR (300 MHz, $CDCl_3$) δ 28.8, 29.0, 34.3, 36.2, 39.8, 40.0, 42.3, 42.6, 45.9, 46.5, 50.4, 51.5, 54.6, 58.5, 59.6, 60.3, 126.3, 128.0, 131.2, 148.1, 149.4; MS m/z (rel intensity) 374.7 (MH$^+$, 30), 375.7 (5), 376.7 (8).

Compound 84: N-tert-Butyl-N'[3-(4-chloro-phenyl)-adamantan-1-ylmethyl]-propane-1,3-diamine Yield=18%; oil; $^1$H NMR (300 MHz, CDCl$_3$) δ 1.29-1.32 (m, 6H, CH$_2$), 1.55-1.90 (m, 21H, Admant-CH, C(CH$_3$)$_3$), 2.21-2.46 (m, 2H, Admant-CH), 2.42-2.87 (m, 2H, NH), 3.29-3.31 (d, J=6 Hz, 2H, CH$_2$), 7.26-7.28 (m, 4H, Ar—H); $^{13}$C NMR (300 MHz, CDCl$_3$) δ 26.4, 26.6, 28.6, 28.7, 28.8, 36.2, 38.2, 38.4, 38.6, 39.7, 42.7, 44.6, 126.3, 128.0; MS m/z (rel intensity) 389.6 (MH$^+$,100).

Compound 85: [3-(4-Chloro-phenyl)-adamantan-1-ylmethyl]-(3-pyrrolidin-1-yl-propyl)-amine 15 mg, Yield=15%; m.p.: 138-140° C.; $^1$H NMR (300 MHz, CDCl$_3$) δ 1.56-1.91 (m, 18H, Admant-CH, CH$_2$), 2.21-2.46 (m, 5H, Admant-CH, NH, CH$_2$), 2.72-2.89 (m, 6H, CH$_2$), 3.52 (m, 2H, CH$_2$), 7.26-7.28 (m, 4H, Ar—H); $^{13}$C NMR (300 MHz, CDCl$_3$) δ 22.8, 22.9, 23.3, 28.6, 29.8, 34.6, 35.6, 36.6, 39.6, 39.8, 42.1, 42.2, 46.1, 56.6, 61.2, 61.3, 62.2, 126.2, 128.2, 131.5, 147.9; MS m/z (rel intensity) 387.6 (MH$^+$,100), 388.6 (60), 389.6 (65).

Compound 86: [3-(4-Chloro-phenyl)-adamantan-1-ylmethyl]-[2-(1-methyl-pyrrolidin-2-yl)-ethyl]-amine 23 mg, Yield=24%; oil; $^1$H NMR (300 MHz, CDCl$_3$) δ 1.54-1.87 (m, 20H, CH$_2$, Admant-H), 2.18 (s, 2H, Admant-H), 2.29-2.41 (m, 4H, CH$_2$), 2.62 (m, 3H, NCH$_3$), 2.87-3.18 (m, 1H, NCH), 3.36 (m, 1H, NH), 7.27 (s, 4H, Ar—H); $^{13}$C NMR (300 MHz, CDCl$_3$) δ 29.0, 36.2, 36.7, 40.0, 40.6, 42.7, 46.6, 48.6, 57.2, 64.7, 126.3, 128.0; MS m/z (rel intensity) 387.4 (MH$^+$,100), 388.4 (33), 389.4 (40).

Compound 87: [3-(4-Chloro-phenyl)-adamantan-1-ylmethyl]-(2-morpholin-4-yl-ethyl)-amine 9 mg, Yield=9%; oil; $^1$H NMR (300 MHz, CDCl$_3$) δ 1.57-1.90 (m, 16H, Admant-H), 2.25 (s, 2H, Admant-H), 2.36-2.47 (m, 4H, CH$_2$), 2.73-2.99 (m, 4H, NCH$_2$), 3.57-3.58 (m, 2H, NCH$_2$), 4.32 (m, 1H, NH), 7.27 (s, 4H, Ar—H); $^{13}$C NMR (300 MHz, CDCl$_3$) δ 28.6, 29.1, 35.7, 36.2, 39.7, 40.0, 46.6, 47.4, 53.8, 54.5, 55.4, 62.9, 67.1, 126.1, 16.3, 128.0, 128.2; MS m/z (rel intensity) 389.7 (MH$^+$, 100), 390.7 (33), 391.7 (40).

Compound 88: [3-(4-Chloro-phenyl)-adamantan-1-ylmethyl]-pyridin-4-ylmethyl-amine Yield=72%; oil; $^1$H NMR (300 MHz, CDCl$_3$) δ 1.55-1.84 (m, 12H, Admant-H), 2.20 (s, 2H, CH$_2$), 2.29 (s, 2H, Admant-H), 3.90 (s, 2H, Ar—CH$_2$), 7.26-7.28 (s, 4H, Ar—H), 7.49-7.51 (d, J=6 Hz, 2H, Ar—H), 8.59-8.51 (d, J=6 Hz, 2H, Ar—H); $^{13}$C NMR (300 MHz, CDCl$_3$) δ 28.9, 34.6, 36.0, 36.5, 39.8, 42.5, 46.3, 52.6, 61.7, 123.9, 126.2, 127.9, 128.0, 131.0, 146.8, 148.9, 154.6; MS m/z (rel intensity) 367.7 (MH$^+$, 100), 368.7 (35), 369.7 (60).

Compound 89: [3-(4-Chloro-phenyl)-adamantan-1-ylmethyl]-(9-ethyl-9H-carbazol-3-yl)-amine 77 mg, Yield=81%; oil; MS m/z (rel intensity) 468 (MH$^+$, 20).

Compound 90: [3-(4-Chloro-phenyl)-adamantan-1-ylmethyl]-[5-(4-chloro-phenyl)-thiazol-2-yl]-amine 15.5 mg, Yield=21%; oil; MS m/z (rel intensity) 469 (MH$^+$, 30).

Example 6

Methods for the Synthesis of Adamantylethylamine and Adamantylethylamide Compounds As an example, a process for the synthesis of adamantylethylamine and adamantylethylamide compounds is described in Scheme 4. Substituted-1-adamantanecarbonyl chlorides (4) were prepared as described in Example 1. Reaction of 4 with dimethyl malonate in toluene in the presence of sodium hydroxide yielded dimethyl (3-R-substituted-phenyl-1-adamantanecarbonyl)malonates (5), which were hydrolyzed by a mixture of acetic acid with water and sulfuric acid (CH$_3$COOH—H$_2$O—H$_2$SO$_4$ ratio 10:3:1) to afford the corresponding 3-R-substituted-phenyl-1-adamantyl methyl ketone (6). Ketone 6 was reacted with formamide and formic acid (Leukart reaction) to yield 7, which can be modified by either alkylation or acylation to produce adamantylethylamine compounds (8) or adamantylethylamide compounds (9).

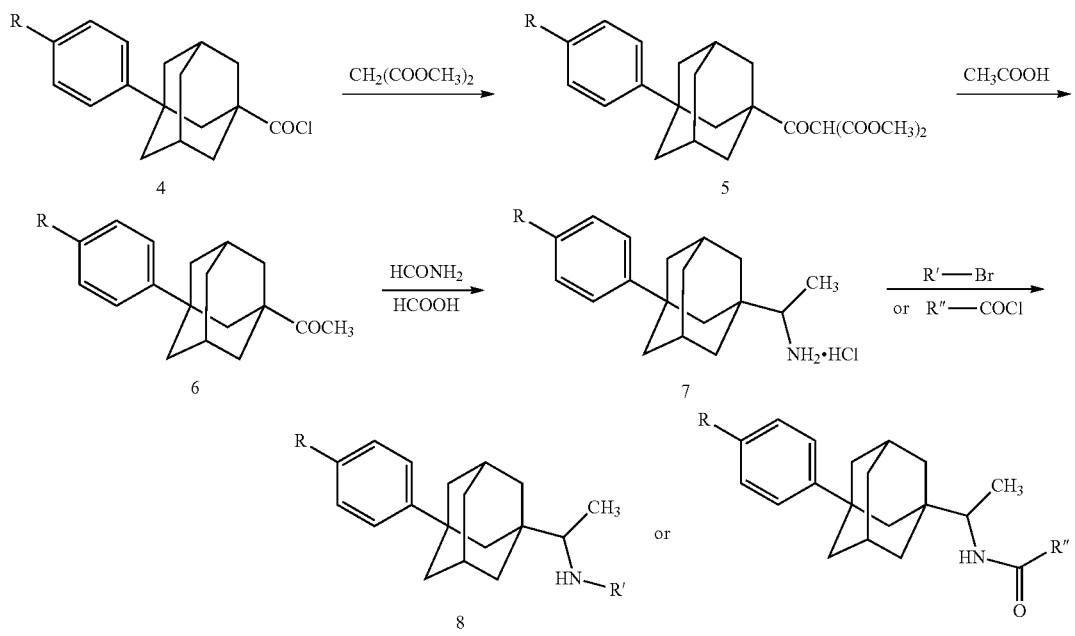

Scheme 4

A second method for the synthesis of adamantylethylamine compounds is described in Scheme 5. 3-R-substituted-phenyl-1-adamantyl methyl ketone (6) was prepared as described above. By reaction of 6 with a substituted primary amine in formic acid, i.e. a Wallach reaction, the corresponding adamantylethylamine compound (8) can be obtained. For example, by reaction of 4-chloro-6 with 4-amino-1-methylpiperidine, which was synthesized by converting N-methyl piperidone to the corresponding oxime followed by reduction to the amino compound using lithium aluminum hydride (LiAlH$_4$), {1-[3-(4-chloro-phenyl)-adamantan-1-yl]-ethyl}-(1-methyl-piperidin-4-yl)-amine, also referred to as Compound 107, was obtained.

Scheme 5

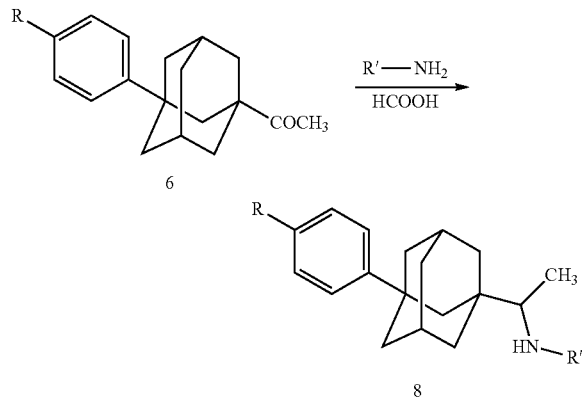

The following Example provides several representatives of the products of these processes; however, these methods can be adapted to produce many structurally related adamantylethylamine or adamantylethylamide compounds that are considered to be subjects of this invention.

Example 7

Synthesis of Adamantylethylamine Compounds

The methods described in Example 6 were used to prepare a library of substituted adamantylethylamine compounds. Data provided below include: the amount synthesized, the yield of the reaction; the melting point (m.p.) of the compound; and mass spectral (MS) data for the compound.

Compound 91: 1-[3-(4-Chloro-phenyl)-adamantan-1-yl]-ethylamine Yield=77%; oil; $^1$H NMR (300 MHz, CDCl$_3$) δ 0.95-0.98 (m, 3H, CH$_3$), 1.30-2.22 (m, 16H, Admant-CH, NH$_2$), 4.24-4.30 (m, 1H, CH), 7.26-7.29 (m, 4H, H—Ar); MS m/z (rel intensity) 290.4 (MH$^+$, 40).

Compound 92: {1-[3-(4-Chloro-phenyl)-adamantan-1-yl]-ethyl}-isopropyl-amine Yield=27%; oil; $^1$H NMR (300 MHz, CDCl$_3$) δ 0.91-0.94 (d, J=6 Hz, 6H, 2CH$_3$), 1.15-1.68 (m, 12H, Admant-CH), 1.81 (m, 3H, CH$_3$), 2.19 (s, 2H, Admant-CH), 3.74-3.76 (m, 1H, HN), 4.24-4.30 (m, 1H, CH), 7.26-7.29 (m, 4H, H—Ar).

Compound 93: Phenyl-[1-(3-phenyl-adamantan-1-yl)-ethyl]-amine.

Compound 94: {1-[3-(4-Fluoro-phenyl)-adamantan-1-yl]-ethyl}-phenyl-amine.

Compound 95: {1-[3-(4-Chloro-phenyl)-adamantan-1-yl]-ethyl}-phenyl-amine Yield=19%; oil.

Compound 96: (1-Adamantan-1-yl-ethyl)-benzyl-amine Yield=64%; m.p.: 62-64° C.; $^1$H NMR (300 MHz, CDCl$_3$) δ 1.12-1.16 (d, J=8 Hz, 3H, CH$_3$), 1.56-2.01 (m, 17H, Admant-CH, CH$_2$), 3.03 (m, 1H, HN), 4.24-4.40 (m, 1H, CH), 7.26-7.30 (m, 4H, Ar—H), 8.32 (s, 1H, Ar—H); $^{13}$C NMR (300 MHz, CDCl$_3$) δ 11.6, 29.1, 32.5, 35.8, 36.7, 38.6, 41.9, 42.2, 44.8, 46.0, 46.4, 54.7, 126.6, 128.5, 131.8, 148.6; MS m/z (rel intensity) 270.5 (MH$^+$, 10).

Compound 97: Benzyl-[1-(3-phenyl-adamantan-1-yl)-ethyl]-amine Yield=41%; oil.

Compound 98: Benzyl-{1-[3-(4-fluoro-phenyl)-adamantan-1-yl]-ethyl}-amine. Yield=42%; oil; $^1$H NMR (300 MHz, CDCl$_3$) δ 0.92-0.95 (d, J=6 Hz, 3H, CH$_3$), 1.49-2.10 (m, 21H, Admant-CH, CH$_2$), 2.19-2.29 (m, 6H, NCH), 2.79-2.94 (m, 1H, HN), 6.94-7.04 (m, 2H, Ar—H), 7.28-7.35 (m, 2H, Ar—H); $^{13}$C NMR (300 MHz, CDCl$_3$) δ 28.98, 35.73, 36.71, 38.77, 42.18, 42.37, 44.88, 122.38, 125.30, 126.57, 128.56, 129.26, 148.39, 150.2; MS m/z (rel intensity) 364.5 (MH$^+$, 75), 365.5 (20).

Compound 99. Benzyl-{1-[3-(4-chloro-phenyl)-adamantan-1-yl]-ethyl}-amine Yield=25%; oil; $^1$H NMR (300 MHz, CDCl$_3$) δ 1.13-1.17 (d, J=8 Hz, 3H, CH$_3$), 1.59-2.05 (m, 15H, Admant-CH, CH$_2$), 2.23 (s, 2H, Admant-H), 3.03 (m, 1H, HN), 4.04-4.10 (m, 1H, CH), 7.20-7.31 (m, 8H, Ar—H), 8.33-8.35 (s, 1H, Ar—H); $^{13}$C NMR (300 MHz, CDCl$_3$) δ 11.6, 29.1, 32.5, 35.8, 36.7, 38.6, 41.9, 42.2, 44.8, 46.0, 46.4, 54.7, 126.6, 128.5, 131.8, 148.6; MS m/z (rel intensity) 380.4 (MH$^+$, 80).

Compound 100: (4-tert-Butyl-benzyl)-{1-[3-(4-chloro-phenyl)-adamantan-1-yl]-ethyl}-amine Yield=2%; oil; MS m/z (rel intensity) 436.3 (MH$^+$, 30).

Compound 101: [1-(4-Bromo-phenyl)-ethyl]-{1-[3-(4-chloro-phenyl)-adamantan-1-yl]-ethyl}-amine Yield=3%; oil; MS m/z (rel intensity) 472.2 (MH$^+$, 98), 474.2 (MH$^+$, 100).

Compound 102: (1-Adamantan-1-yl-ethyl)-[2-(4-bromo-phenyl)-ethyl]-amine. Yield=0.4%; oil; MS m/z (rel intensity) 362.2 (M-H$^+$, 98), 364.2 (M-H$^+$, 100).

Compound 103: [2-(4-Bromo-phenyl)-ethyl]-{1-[3-(4-chloro-phenyl)-adamantan-1-yl]-ethyl}-amine Yield=11%; oil; MS m/z (rel intensity) 472.1 (MH$^+$, 50), 474.1 (MH$^+$, 60).

Compound 104: (1-Adamantan-1-yl-ethyl)-(1-methyl-piperidin-4-yl)-amine Yield=16%; oil; $^1$H NMR (300 MHz, CDCl$_3$) δ 0.91-0.94 (d, J=9 Hz, 3H, CH$_3$), 1.43-2.00 (m, 23H, Admant-CH, CH$_2$), 2.25 (m, 3H, NCH$_3$), 2.47-2.50 (m, 1H, NH), 2.76-2.80 (m, 2H, HC—N); MS m/z (rel intensity) 275.2 (M-H$^+$, 45).

Compound 105: (1-Methyl-piperidin-4-yl)-[1-(3-phenyl-adamantan-1-yl)-ethyl]-amine. Yield=29%; oil; $^1$H NMR (300 MHz, CDCl$_3$) δ 0.92-0.95 (d, J=6 Hz, 3H, CH$_3$), 1.49-2.10 (m, 21H, Admant-CH, CH$_2$), 2.19-2.29 (m, 6H, NCH), 2.79-2.94 (m, 1H, HN), 6.94-7.04 (m, 2H, Ar—H), 7.28-7.35 (m, 5H, Ar—H); $^{13}$C NMR (300 MHz, CDCl$_3$) δ 28.98, 35.73, 36.71, 38.77, 42.18, 42.37, 44.88, 122.38, 125.30, 126.57, 128.56, 129.26, 148.39, 150.2; MS m/z (rel intensity) 353.6 (MH$^+$, 85), 354.6 (25).

Compound 106: {1-[3-(4-Fluoro-phenyl)-adamantan-1-yl]-ethyl}-(1-methyl-piperidin-4-yl)-amine Yield=11%; oil; $^1$H NMR (300 MHz, CDCl$_3$) δ 0.92-0.95 (d, J=6 Hz, 3H, CH$_3$), 1.49-2.10 (m, 21H, Admant-CH, CH$_2$), 2.19-2.29 (m, 6H, NCH), 2.79-2.94 (m, 1H, HN), 6.94-7.04 (m, 2H, Ar—H), 7.28-7.35 (m, 2H, Ar—H); $^{13}$C NMR (300 MHz, CDCl$_3$) δ 28.98, 35.73, 36.71, 38.77, 42.18, 42.37, 44.88, 122.38, 125.30, 126.57, 128.56, 129.26, 148.39, 150.2; MS m/z (rel intensity) 371.5 (MH$^+$, 85), 372.5 (50), 373.5 (8).

Compound 107: {1-[3-(4-Chloro-phenyl)-adamantan-1-yl]-ethyl}-(1-methyl-piperidin-4-yl)-amine Yield=28%; oil; $^1$H NMR (300 MHz, CDCl$_3$) δ 0.95-0.98 (d, J=6 Hz, 3H, CH$_3$), 1.30-2.75 (m, 29H, Admant-CH,

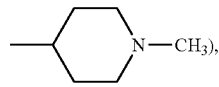

3.74-3.76 (m, 1H, HN), 4.24-4.30 (m, 1H, CH), 7.26-7.29 (m, 4H, H—Ar); MS m/z (rel intensity) 387.3 (MH$^+$, 65).
Compound 108: {1-[3-(4-Chloro-phenyl)-adamantan-1-yl]-ethyl}-(4-methyl-piperazin-1-yl)-amine Yield=23%; oil; MS m/z (rel intensity) 389.2 (MH$^+$, 100).
Compound 109: [1-(3-Phenyl-adamantan-1-yl)-ethyl]-pyridin-4-ylmethyl-amine. Yield=16%; oil; MS m/z (rel intensity) 347.2 (MH$^+$, 30).
Compound 110: {1-[3-(4-Chloro-phenyl)-adamantan-1-yl]-ethyl}-(6-chloro-pyridin-3-ylmethyl)-amine Yield=18%; oil; MS m/z (rel intensity) 415.2 (MH$^+$, 20).
Compound 111: {1-[3-(4-Chloro-phenyl)-adamantan-1-yl]-ethyl}-(2-pyridin-4-yl-ethyl)-amine Oil.
Compound 112: {1-[3-(4-Chloro-phenyl)-adamantan-1-yl]-ethyl}-(3H-imidazol-4-ylmethyl)-amine. Oil.
Compound 113: {1-[3-(4-Chloro-phenyl)-adamantan-1-yl]-ethyl}-(2-methyl-1H-indol-5-yl)-amine Yield=5%; oil; MS m/z (rel intensity) 417.2 (M$^+$-H, 15).
Compound 114: {1-[3-(4-Chloro-phenyl)-adamantan-1-yl]-ethyl}-(9-ethyl-9H-carbazol-3-yl)-amine Yield=60%; m.p.: 70-72° C.; MS m/z (rel intensity) 482 (M$^+$, 50), 483 (MH$^+$, 25), 484 (20).
Compound 115: {1-[3-(4-Chloro-phenyl)-adamantan-1-yl]-ethyl}-(9-ethyl-9H-carbazol-3-ylmethyl)-amine Yield=13%; oil; MS m/z (rel intensity) 496.2 (M-H$^+$, 30).
Compound 116: 9-Ethyl-9H-carbazole-3-carboxylic acid {1-[3-(4-chloro-phenyl)-adamantan-1-yl]-ethyl}-amide. Yield=28.
Compound 117: 1-{1-[3-(4-Chloro-phenyl)-adamantan-1-yl]-ethyl}-3-(4-chloro-3-trifluoromethyl-phenyl)-urea. Yield=6%; m.p.: 103-105° C.; MS m/z (rel intensity) 511.2 (MH$^+$, 5).
Compound 118: 1-{1-[3-(4-Chloro-phenyl)-adamantan-1-yl]-ethyl}-3-(4-chloro-3-trifluoromethyl-phenyl)-urea. m.p: 103-105° C.; $^1$H NMR (300 MHz, DMSO-d$_6$) δ 1.05-1.07 (d, J=6 Hz, 3H, CH$_3$), 1.50-1.80 (m, 12H, Admant-CH), 2.18 (s, 2H, Admant-CH), 3.62-3.68 (m, 1H, CH), 4.83-4.86 (m, 1H, HN), 6.91-6.94 (m, 1H, NH—Ar), 7.20-7.28 (m, 4H, Ar—H), 7.32-7.35 (d, J=9 Hz, 1H, Ar—H), 7.48-7.51 (d, J=9 Hz, 1H, Ar—H), 7.60 (s, 1H, Ar—H); $^{13}$C NMR (300 MHz, CDCl$_3$) δ 15.2, 28.8, 36.0, 36.5, 37.6, 37.8, 42.4, 54.0, 56.1, 117.8, 122.8, 126.2, 128.1, 131.8, 132.7, 154.6; MS m/z (rel intensity) 511 (MH$^+$, 5).
Compound 119: (4-Bromo-thiophen-2-ylmethyl)-{1-[3-(4-chloro-phenyl)-adamantan-1-yl]-ethyl}-amine Yield=8%; oil; MS m/z (rel intensity) 464.1 (MH$^+$, 50).
Compound 120: {1-[3-(4-Chloro-phenyl)-adamantan-1-yl]-ethyl}-(4-phenyl-thiophen-2-ylmethyl)-amine Yield=8%; oil; m/z (rel intensity) 463.0 (MH$^+$, 100).

Example 8

Method for the Synthesis of Adamantylpropenones

As an example, a process for the synthesis of adamantylpropenone compounds is described in Scheme 5. 3-R-substituted-phenyl-1-adamantyl methyl ketone (6) was prepared as described above. By reaction of 6 with a substituted aldehyde, the corresponding adamantylpropenone compound (10) can be obtained. For example, by reaction of 4-chloro-6 with 4-hydroxybenzylaldehyde, 1-[3-(4-chloro-phenyl)-adamantan-1-yl]-3-(4-hydroxy-phenyl)-propenone, also referred to as Compound 132, was obtained.

Scheme 5

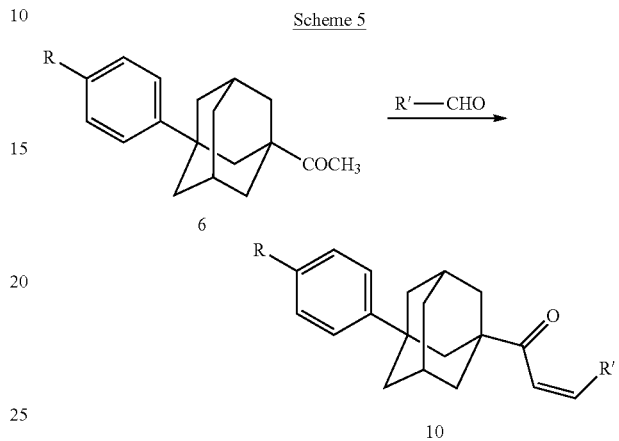

Example 9

Synthesis of Adamantylpropenones

The methods described in Example 6 were used to prepare a library of substituted adamantylpropenone compounds. Data provided below include: the yield of the reaction; the melting point (m.p.) of the compound; and mass spectral (MS) data for the compound.
Compound 121: 3-Phenyl-adamantane-1-carboxylic acid.
Compound 122: 3-(4-Fluoro-phenyl)-adamantane-1-carboxylic acid.
Compound 123: 3-(4-Chloro-phenyl)-adamantane-1-carboxylic acid. Yield=79%.
Compound 124: 1-Adamantan-1-yl-ethanone. m.p.: 44-46° C.
Compound 125: 1-(3-Phenyl-adamantan-1-yl)-ethanone. Yield=54%; $^1$H NMR (300 MHz, CDCl$_3$) δ 1.73-2.10 (m, 12H, Admant-CH), 2.14 (s, 3H, CH$_3$), 2.27 (s, 2H, Admant-CH), 7.25-7.26 (m, 1H, Ar—H), 7.30-7.36 (m, 4H, H—Ar).
Compound 126: 1-[3-(4-Fluoro-phenyl)-adamantan-1-yl]-ethanone. Yield=59%; 59%; oil; $^1$H NMR (300 MHz, CDCl$_3$) δ 1.73-1.90 (m, 12H, Admant-CH), 2.10 (s, 3H, CH$_3$), 2.27 (s, 2H, Admant-CH), 6.96-7.04 (m, 2H, Ar—H), 7.28-7.35 (m, 2H, H—Ar).
Compound 127: 1-[3-(4-Chloro-phenyl)-adamantan-1-yl]-ethanone. Yield=54% (2 steps); m.p.: 54-56° C.
Compound 128: 2-(Adamantane-1-carbonyl)-malonic acid dimethyl ester. Yield=80%; oil.
Compound 129: 2-[3-(4-Chloro-phenyl)-adamantane-1-carbonyl]-malonic acid dimethyl ester. Yield=91%; oil.
Compound 130: 3-(4-Chloro-phenyl)-1-[3-(4-chloro-phenyl)-adamantan-1-yl]-propenone. Yield=18%.
Compound 131: 4-{3-[3-(4-Chloro-phenyl)-adamantan-1-yl]-3-oxo-propenyl}-benzonitrile.
Compound 132: 1-[3-(4-Chloro-phenyl)-adamantan-1-yl]-3-(4-hydroxy-phenyl)-propenone. Yield=16%; m.p.: 87-89° C.; MS m/z (rel intensity) 393.2 (MH$^+$, 100).

Compound 133: 1-[3-(4-Chloro-phenyl)-adamantan-1-yl]-3-naphthalen-2-yl-propenone. Yield=20%; m.p.: 82-84° C.
Compound 134: 1-[3-(4-Chloro-phenyl)-adamantan-1-yl]-3-(6-chloro-pyridin-3-yl)-propenone. Yield=4%.
Compound 135: 1-[3-(4-Chloro-phenyl)-adamantan-1-yl]-3-(1H-imidazol-4-yl)-propenone. Yield=3%; oil.
Compound 136: 1-[3-(4-Chloro-phenyl)-adamantan-1-yl]-3-(9-ethyl-9H-carbazol-3-yl)-propenone. Yield=3%; m.p.: 138-140° C.
Compound 137: 1-[3-(4-Chloro-phenyl)-adamantan-1-yl]-3-(4-phenyl-thiophen-2-yl)-propenone. Yield=13%.

Example 10

Assays for Inhibition of Human SK Activity

An assay for identifying inhibitors of recombinant human SK has been established (French et al., 2003, Cancer Res 63: 5962). cDNA for human SK was subcloned into a pGEX bacterial expression vector, which results in expression of the enzyme as a fusion protein with glutathione-S-transferase, and the fusion protein is then purified on a column of immobilized glutathione. SK activity is measured by incubation of the recombinant SK with [$^3$H]sphingosine and 1 mM ATP under defined conditions, followed by extraction of the assay mixture with chloroform:methanol under basic conditions. This results in the partitioning of the unreacted [$^3$H]sphingosine into the organic phase, while newly synthesized [$^3$H] S1P partitions into the aqueous phase. Radioactivity in aliquots of the aqueous phase is then quantified as a measure of [$^3$H]S1P formation. There is a low background level of partitioning of [$^3$H]sphingosine into the aqueous phase, and addition of the recombinant SK greatly increases the formation of [$^3$H]S1P. A positive control, DMS, completely inhibits SK activity at concentrations above 25 µM.

In an alternate assay procedure, the recombinant human SK was incubated with unlabeled sphingosine and ATP as described above. After 30 minutes, the reactions were terminated by the addition of acetonitrile to directly extract the newly synthesized S1P. The amount of S1P in the samples is then quantified as follows. $C_{17}$ base D-erythro-sphingosine and $C_{17}$ S1P are used as internal standards for sphingosine and S1P, respectively. These seventeen-carbon fatty acid-linked sphingolipids are not naturally produced, making these analogs excellent standards. The lipids are then fractionated by High-Performance Liquid Chromatography using a C8-reverse phase column eluted with 1 mM methanolic ammonium formate/2 mM aqueous ammonium formate. A Finnigan LCQ Classic LC-MS/MS is used in the multiple reaction monitoring positive ionization mode to acquire ions at m/z of 300 (precursor ion)→282 (product ion) for sphingosine and 380→264 for S1P. Calibration curves are generated by plotting the peak area ratios of the synthetic standards for each sphingolipid, and used to determine the normalized amounts of sphingosine and S1P in the samples.

Example 11

Inhibition of Human SK by Compounds of this Invention

Each Compound of this invention was tested for its ability to inhibit recombinant SK using the LC/MS/MS assay described above. Typically, the Compounds were individually dissolved in dimethylsulfoxide and tested at a final concentration of 6 µg/ml. The results for the assays are shown in Table 3. The data demonstrate that compounds of Formula I demonstrate a range of abilities to inhibit the in vitro activity of recombinant SK. Several Compounds caused complete suppression of SK activity at the concentration of 6 micrograms/ml (corresponding to approximately 15 micromolar). As detailed in the Examples below, significantly greater concentrations of the Compounds can be achieved in the blood of mice receiving the Compounds by oral administration, indicating that the Compounds are sufficiently potent to be therapeutically useful.

Although many of the Compounds inhibited the purified SK enzyme, it was useful to determine their abilities to inhibit endogenous SK in an intact cell. We have previously described an intact cell assay where, following treatment with a test compound, MDA-MB-231 human breast carcinoma cells are incubated with [$^3$H]sphingosine at a final concentration of 1 µM (French et al., Cancer Res 63: 5962 (2003)). The cells take up the exogenous [$^3$H]sphingosine and convert it to [$^3$H]S1P through the action of endogenous SK. The resulting [$^3$H]S1P is isolated via charge-based separation as indicated above. The results from this assay are indicated in Table 3. The data demonstrate that many of the Compounds that inhibit purified SK also inhibit SK activity in the intact cell. For potency studies, MDA-MB-231 cells were exposure to varying concentrations of a test Compound and then assayed for conversion of [$^3$H]sphingosine to [$^3$H]S1P. Each of Compounds decreased [$^3$H]S1P formation in a dose dependent fashion, with $IC_{50}$ values ranging from 15 to 64 µM. These results demonstrate that compounds of formula I or II effectively inhibit SK activity in intact cells.

TABLE 3

Inhibition of SK activity

| Compound | Recombinant SK (% inhibition) | Cellular S1P (% inhibition) | Cellular S1P $IC_{50}$ (µM) |
|---|---|---|---|
| 1 | 38 | 0 | ND |
| 2 | 0 | ND | ND |
| 3 | 6 | ND | ND |
| 4 | 44 | 14 | ND |
| 5 | 100 | 17 | ND |
| 6 | 72 | 90 | 15 |
| 7 | 100 | 96 | ND |
| 8 | 49 | 0 | ND |
| 9 | 84 | 40 | ND |
| 10 | 3 | 9 | ND |
| 11 | 17 | 0 | ND |
| 12 | 36 | 3 | ND |
| 13 | 78 | 0 | ND |
| 14 | 19 | ND | ND |
| 16 | 8 | ND | ND |
| 17 | 56 | ND | ND |
| 18 | 0 | ND | ND |
| 20 | 0 | ND | ND |
| 21 | 65 | ND | ND |
| 22 | 56 | ND | ND |
| 23 | 0 | ND | ND |
| 24 | 20 | ND | ND |
| 25 | 47 | ND | ND |
| 26 | 36 | ND | ND |
| 27 | 50 | ND | ND |
| 28 | 6 | ND | ND |
| 29 | 55 | 0 | ND |
| 30 | 1 | ND | ND |
| 31 | 74 | ND | ND |
| 32 | 17 | ND | ND |
| 33 | 10 | ND | ND |
| 34 | 0 | ND | ND |
| 35 | 87 | 0 | ND |
| 36 | 37 | 72 | ND |
| 37 | 24 | 36 | ND |
| 38 | 40 | 34 | ND |
| 39 | 19 | 26 | ND |

TABLE 3-continued

Inhibition of SK activity

| Compound | Recombinant SK (% inhibition) | Cellular S1P (% inhibition) | Cellular S1P IC$_{50}$ (μM) |
|---|---|---|---|
| 40 | 100 | 52 | ND |
| 41 | 67 | 23 | ND |
| 42 | 5 | ND | ND |
| 43 | 0 | 0 | ND |
| 44 | 33 | 88 | 35 |
| 45 | 64 | ND | ND |
| 46 | 4 | ND | ND |
| 47 | 26 | ND | ND |
| 48 | 36 | 14 | ND |
| 49 | 33 | ND | ND |
| 50 | 0 | 44 | ND |
| 51 | 84 | 88 | 25 |
| 52 | 54 | 61 | ND |
| 53 | 52 | ND | ND |
| 54 | 95 | ND | ND |
| 55 | 8 | ND | ND |
| 56 | 33 | 40 | ND |
| 57 | 30 | 83 | 60 |
| 58 | 67 | 55 | ND |
| 59 | 0 | ND | ND |
| 60 | 0 | 23 | ND |
| 61 | 58 | 24 | ND |
| 62 | 13 | 92 | 26 |
| 63 | 0 | 39 | ND |
| 64 | 41 | 80 | 63 |
| 65 | 3 | ND | ND |
| 66 | 92 | 8 | ND |
| 67 | 10 | ND | ND |
| 68 | 17 | 0 | ND |
| 69 | 40 | 13 | ND |
| 70 | 33 | 4 | ND |
| 71 | 27 | 0 | ND |
| 72 | 14 | 1 | ND |
| 73 | 53 | ND | ND |
| 74 | 0 | 28 | ND |
| 75 | ND | 41 | ND |
| 76 | 42 | ND | ND |
| 77 | 27 | ND | ND |
| 78 | 43 | ND | ND |
| 79 | 19 | ND | ND |
| 80 | 5 | ND | ND |
| 81 | 67 | ND | ND |
| 82 | 75 | ND | ND |
| 83 | 60 | 88 | 16 |
| 84 | 84 | ND | ND |
| 85 | 0 | ND | ND |
| 86 | 6 | ND | ND |
| 87 | 75 | 55 | 64 |
| 88 | 1 | ND | ND |
| 89 | 37 | 1 | ND |
| 90 | 26 | 16 | ND |
| 93 | 70 | ND | ND |
| 104 | 0 | ND | ND |
| 114 | 33 | 46 | 51 |
| 118 | 77 | 5 | ND |
| 130 | 38 | ND | ND |
| 131 | 41 | ND | ND |
| 132 | 8 | ND | ND |
| 133 | 36 | ND | ND |
| 134 | 52 | ND | ND |
| 135 | 64 | ND | ND |

Human SK was incubated with 6 μg/ml of the indicated compounds, and then assayed for activity as described above. Values in the column labeled "Recombinant SK (% inhibition)" represent the percentage of SK activity that was inhibited. MDA-MB-231 cells were incubated with 20 μg/ml of the indicated compounds and then assayed for endogenous SK activity as indicated above. Values in the column labeled "Cellular S1P (% inhibition)" represent the percentage of S1P production that was inhibited. Additionally, MDA-MB-231 cells were treated with varying concentration of certain compounds and the amount of S1P produced by the cells was determined. Values in the column labeled "Cellular S1P IC$_{50}$ (μM)" represent the concentration of compound required to inhibit the production of S1P by 50%. ND = not determined.

Example 12

Selectivity of SK Inhibitors of this Invention

A common problem with attempts to develop protein kinase inhibitors is the lack of selectivity toward the target kinase since the majority of these compounds interact with nucleotide-binding domains that are highly conserved among kinases. To determine if compound of this invention are non-selective kinase inhibitors, the effects of the SK inhibitor, Compound 62, on a diverse panel of 20 purified kinases was determined. The compound was tested at a single concentration of 50 μM. The kinases and the effects of the SK inhibitor are shown in Table 4.

The data indicate high specificity of Compound 62 for SK in that none of the 20 diverse kinases tested were significantly inhibited by this compound. The panel included both serine/threonine kinases and tyrosine kinases, as well as several that are regulated by their interaction with lipids. Overall, the data indicate that the biological effects of the compounds of this invention are not mediated by off-target inhibition of protein kinases.

TABLE 4

Selectivity of Compound 62.

| Kinase | Compound 62 |
|---|---|
| $Ca^{2+}$/calmodulin PK IV | 81 ± 3 |
| Abl | 98 ± 0 |
| Aurora-A | 103 ± 1 |
| Protein kinase C α | 86 ± 5 |
| Protein kinase C ε | 101 ± 1 |
| CDK1/cyclinB | 105 ± 1 |
| CDK2/cyclinE | 106 ± 6 |
| P38 MAP kinase 1 | 94 ± 2 |
| P38 MAP kinase 2 | 109 ± 5 |
| PDK1 | 116 ± 3 |
| MEK kinase 1 | 104 ± 3 |
| CHK1 | 142 ± 13 |
| EFGR | 101 ± 3 |
| Fyn | 84 ± 5 |
| cSrc | 115 ± 3 |
| IKKα | 150 ± 16 |
| PKA | 104 ± 5 |
| PKBα | 95 ± 2 |
| PKBγ | 105 ± 8 |
| cRaf | 96 ± 5 |

Values represent the percent of control activity of the indicated kinase in the presence of 50 μM of Compound 62.

Example 13

Cytotoxicity Profiles of SK Inhibitors of this Invention

To further assess the biological efficacies of the Compounds in intact cells, each Compound was evaluated for cytotoxicity using human cancer cell lines. These experiments followed methods that have been extensively used. Cell lines tested included MCF-7 human breast adenocarcinoma cells and MCF-10A non-transformed human breast epithelial cells. The indicated cell lines were treated with varying doses of the test Compound for 48 h. Cell survival was then determined using the SRB binding assay (Skehan et al., 1990, *J Natl Cancer Inst* 82: 1107), and the concentration of compound that inhibited proliferation by 50% (the IC$_{50}$) was calculated. The cytotoxicities of the compounds of this invention are summarized in Table 5. Values (in μM) represent the mean±sd for replicate trials. As the data show, the compounds of this invention are antiproliferative at sub-to-low-micromolar. In many cases, the transformed MCF-7 cells were significantly more sensitive than were the non-transformed MCF-10A cells. This indicates that the Compounds will inhibit the growth of tumor cells without inducing toxicity to normal cells within the patient. Overall, the data demonstrate that these Compounds are able to enter intact cells and prevent their proliferation, making them useful for the indications described above.

TABLE 5

Anticancer activity of compounds of this invention.

| Compound | MCF-7 IC$_{50}$ (μM) | MCF-10A IC$_{50}$ (μM) |
| --- | --- | --- |
| 1 | 23 | 151 |
| 2 | 20 | ND |
| 3 | 18 | ND |
| 4 | 72 | 137 |
| 5 | ND | 30 |
| 6 | 5 | 15 |
| 7 | 3 | ND |
| 8 | 47 | 94 |
| 9 | 9 | 17 |
| 10 | ND | 170 |
| 11 | 87 | 87 |
| 12 | 11 | 99 |
| 13 | 51 | 115 |
| 14 | 36 | ND |
| 15 | >112 | ND |
| 16 | 17 | ND |
| 17 | 17 | ND |
| 18 | 19 | ND |
| 19 | >108 | ND |
| 20 | 33 | ND |
| 21 | 27 | ND |
| 22 | 18 | ND |
| 23 | 23 | ND |
| 24 | 17 | ND |
| 25 | 87 | ND |
| 26 | 19 | ND |
| 27 | 8 | ND |
| 28 | 64 | ND |
| 29 | 7 | 106 |
| 30 | 14 | ND |
| 31 | 74 | ND |
| 32 | 24 | ND |
| 33 | 30 | ND |
| 34 | >106 | ND |
| 35 | 19 | ND |
| 36 | 13 | 9 |
| 37 | 5 | 127 |
| 38 | 9 | 40 |
| 39 | 15 | 106 |
| 40 | 6 | 37 |
| 41 | 6 | 71 |
| 42 | >100 | ND |
| 43 | 27 | ND |
| 44 | 6 | 9 |
| 45 | 17 | ND |
| 46 | 91 | ND |
| 47 | 16 | ND |
| 48 | ND | ND |
| 49 | 68 | ND |
| 50 | 181 | ND |
| 51 | 8 | 25 |
| 52 | 10 | 15 |
| 53 | 11 | ND |
| 54 | 11 | ND |
| 55 | ND | ND |
| 56 | 10 | ND |
| 57 | 6 | 8 |
| 58 | 20 | 36 |
| 59 | ND | ND |
| 60 | 7 | ND |
| 61 | ND | ND |
| 62 | 17 | 21 |

TABLE 5-continued

Anticancer activity of compounds of this invention.

| Compound | MCF-7 IC$_{50}$ (μM) | MCF-10A IC$_{50}$ (μM) |
| --- | --- | --- |
| 63 | 11 | ND |
| 64 | 8 | 20 |
| 65 | ND | ND |
| 66 | 19 | 53 |
| 67 | ND | ND |
| 68 | 54 | 104 |
| 69 | 30 | 106 |
| 70 | 7 | 103 |
| 71 | 21 | 118 |
| 72 | 2 | 6 |
| 73 | 80 | ND |
| 74 | 3 | 70 |
| 75 | 11 | ND |
| 76 | 5 | ND |
| 77 | ND | ND |
| 78 | 30 | ND |
| 79 | ND | ND |
| 80 | ND | ND |
| 81 | ND | ND |
| 82 | ND | ND |
| 83 | 5 | ND |
| 84 | ND | ND |
| 85 | ND | ND |
| 86 | 5 | ND |
| 87 | 38 | 33 |
| 88 | 11 | ND |
| 89 | 74 | 41 |
| 90 | 96 | 107 |
| 91 | 5 | 4 |
| 92 | 2 | 6 |
| 93 | 15 | ND |
| 94 | 0.6 | ND |
| 95 | 22 | 68 |
| 96 | 9 | 9 |
| 97 | 0.5 | ND |
| 98 | 3 | ND |
| 99 | 0.7 | ND |
| 100 | 0.3 | ND |
| 101 | 10 | ND |
| 102 | 2 | ND |
| 103 | ND | ND |
| 104 | 34 | ND |
| 105 | 5 | 14 |
| 106 | 2 | 6 |
| 107 | 1 | 1 |
| 108 | 5 | ND |
| 109 | 26 | ND |
| 110 | 6 | ND |
| 111 | 13 | ND |
| 112 | 5 | ND |
| 113 | 14 | ND |
| 114 | 55 | 9 |
| 115 | 1 | ND |
| 116 | 6 | ND |
| 117 | 3 | ND |
| 118 | ND | ND |
| 119 | 11 | ND |
| 120 | 108 | ND |
| 121 | 13 | 176 |
| 122 | 155 | 182 |
| 123 | 48 | 95 |
| 124 | 11 | 105 |
| 125 | 8 | 59 |
| 126 | 2 | 6 |
| 127 | 6 | 16 |
| 128 | 34 | 63 |
| 129 | 16 | 105 |
| 130 | 7 | ND |
| 131 | 27 | ND |
| 132 | 17 | ND |
| 133 | 13 | ND |
| 134 | 16 | ND |

TABLE 5-continued

Anticancer activity of compounds of this invention.

| Compound | MCF-7 IC$_{50}$ (µM) | MCF-10A IC$_{50}$ (µM) |
|---|---|---|
| 135 | 3 | ND |
| 136 | 8 | ND |
| 137 | 9 | ND |

The cytotoxicity of the indicated Compounds toward human breast cancer cells (MCF-7) and non-transformed human breast epithelial cells (MCF-10A) were determined. Values represent the mean IC$_{50}$ for inhibition of cell proliferation.
ND = not determined.

Example 14

Survey of Anticancer Activity of SK Inhibitors of this Invention

The data provided above demonstrate the abilities of compounds of this invention to inhibit the proliferation of human breast carcinoma cells. To examine the range of anticancer activity of representative compounds, the chemotherapeutic potencies of Compounds 62 and 57 towards a panel of varied human tumor cell lines representing several major tumor types were determined. The data are described in Table 6, and demonstrate that the compounds of this invention have anticancer activity against a wide variety of cancers.

TABLE 6

Potencies of SK inhibitors toward human tumor cell lines.

| Cell Line | Tissue | IC$_{50}$ (µM) Compound 62 | IC$_{50}$ (µM) Compound 57 |
|---|---|---|---|
| 1025LU | melanoma | 33.7 ± 2.7 | 7.2 ± 0.8 |
| A-498 | kidney | 12.2 ± 6.0 | 8.0 ± 3.5 |
| Caco-2 | colon | 11.8 ± 5.6 | 3.2 ± 2.0 |
| DU145 | prostate | 21.9 ± 1.5 | 8.7 ± 3.3 |
| Hep-G2 | liver | 6.0 ± 2.6 | 5.0 ± 1.8 |
| HT-29 | colon | 48.1 ± 7.6 | 9.6 ± 4.0 |
| MCF-7 | breast, ER+ | 18.4 ± 7.4 | 12.1 ± 3.1 |
| MDA-MB-231 | breast, ER− | 29.1 ± 11.1 | 12.5 ± 2.5 |
| Panc-1 | pancreas | 32.8 ± 0.1 | 14.1 ± 6.3 |
| SK-OV-3 | ovary | 10.5 ± 2.6 | 9.2 ± 2.8 |
| T24 | bladder | 39.4 ± 7.4 | 12.7 ± 2.8 |

Sparsely plated cells were treated with an SK inhibitor for 48 hours, and cell viability was determined using sulforhodamine B staining and compared to vehicle-(DMSO) treated cells. Values are the mean ± sd for at least three separate experiments.

Example 15

In Vivo Toxicity of SK Inhibitors of this Invention

For example, Compounds 62 and 57 were found to be soluble to at least 15 mg/ml (~30-40 mM) in DMSO:PBS for intraperitoneal (IP) administration or PEG400 for oral dosing. Acute toxicity studies using IP dosing demonstrated no immediate or delayed toxicity in female Swiss-Webster mice treated with up to at least 50 mg/kg of Compounds 62 and 57. Repeated injections in the same mice every other day over 15 days showed similar lack of toxicity. Each of the compounds could also be administered orally to mice at doses up to at least 100 mg/kg without noticeable toxicity.

Example 16

Pharmacokinetics of SK Inhibitors of this Invention

Oral pharmacokinetic studies were performed on Compounds 62 and 57. Each compound was dissolved in PEG400 and administered to female Swiss-Webster mice at a dose of 100 mg/kg by oral gavage. Mice were anesthetized and blood was removed via cardiac puncture at 5 minutes, 30 minutes, 1, 2, and 8 hours. Concentrations of the test compounds were determined using liquid-liquid extraction, appropriate internal standards and reverse phase HPLC with UV detection. Control blood samples were run to identify compound-specific peaks. Pharmacokinetic parameters were calculated using the WINNONLIN analysis software package (Pharsight). Non-compartmental and compartmental models were tested, with the results shown in Table 7 derived from the best fit equations.

TABLE 7

Oral pharmacokinetic data for SKI inhibitors.

| Compound | Dose (mg/kg) | AUC$_{0\to\infty}$ (µg * h/mL) | AUC$_{0\to\infty}$ (µM * h) | $t_{max}$ (h) | $C_{max}$ (µM) | $t_{1/2}$ (h) |
|---|---|---|---|---|---|---|
| 62 | 100 | 172 | 452 | 0.5 | 55.8 | 7.3 |
| 57 | 100 | 45 | 111 | 2.0 | 3.8 | 19.3 |

These studies demonstrate that substantial amounts of each compound can be detected in the blood 1 h after oral dosing. Both compounds have excellent PK properties, with Area Under the Curve (AUC) and $C_{max}$ (maximum concentration reached in the blood) values exceeding the IC$_{50}$ for recombinant SK catalytic activity, as well as for S1P formation in the intact cell model for at least 8 h. The high half-life suggests prolonged activity, which will diminish the need for frequent dosing regimens. These PK properties demonstrate that the compounds of this invention have excellent drug properties, specifically high oral availability with low toxicity.

Oral bioavailability studies were performed on Compound 62 dissolved in 0.375% Tween-80. Female Swiss-Webster mice were dosed with 50 mg/kg Compound 62 either intravenously or orally. Mice were anesthetized and blood was removed by cardiac puncture at time points ranging from 1 minute to 8 hours. Concentrations of Compound 62 were quantified using liquid-liquid extraction and reverse phase HPLC coupled to an ion trap quadrapole mass spectrometer. Control blood samples were spiked with known amounts of internal standard and analyte to identify compound-specific peaks and to develop standard curves for quantification. Pharmacokinetic parameters were calculated using the WINNONLIN analysis software package (Pharsight). Non-compartmental and compartmental models were tested, with the results from the best fitting models shown in Table 8.

TABLE 8

Bioavailability data for Compound 62.

| Route | Dose (mg/kg) | AUC$_{0\to\infty}$ (µg * h/ml) | AUC$_{0\to\infty}$ (µM * h) | $T_{max}$ (h) | $C_{max}$ (µg/ml) | $C_{max}$ (µM) | $T_{1/2}$ (h) |
|---|---|---|---|---|---|---|---|
| IV | 50 | 56.9 | 137 | 0 | 31.1 | 74 | 1.4 |
| Oral | 50 | 37.5 | 90.1 | 0.25 | 8 | 19 | 4.5 |

Blood levels of Compound 62 exceeded the IC$_{50}$ for inhibition of SK activity during the entire study. Comparison of oral versus intravenous pharmacokinetics of Compound 62 revealed very good oral bioavailability properties (F=AUC (oral)/AUC (iv)=0.66). These results demonstrate that Compound 62 has excellent drug properties, specifically good oral availability with low toxicity.

Example 17

Antitumor Activity of SK Inhibitors of this Invention

The antitumor activity of the representative SK inhibitors were evaluated using a syngeneic tumor model that uses the mouse JC mammary adenocarcimona cell line growing subcutaneously in immunocompetent Balb/c mice (Lee et al., 2003, *Oncol Res* 14: 49). These cells express elevated levels of SK activity relative to non-transformed cells, as well as the multidrug resistance phenotype due to P-glycoprotein activity.

Figure 2:
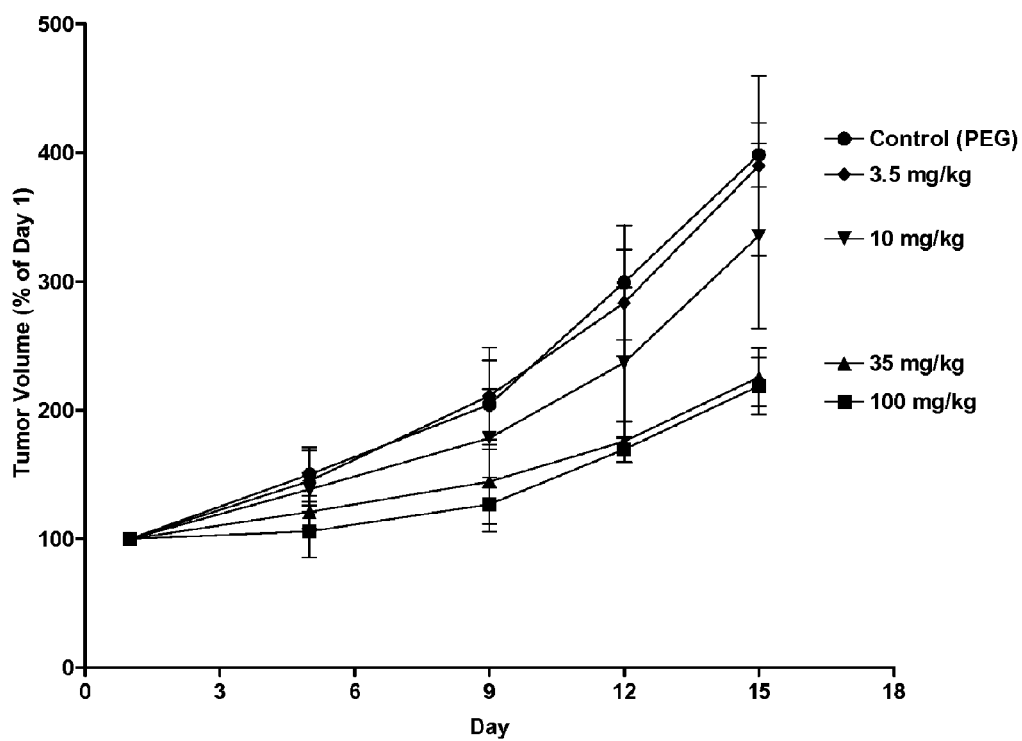
FIG. 2. Dose-response relationships for inhibition of tumor growth by Compound 62. Balb/c female mice were injected subcutaneously with JC cells suspended in PBS. After palpable tumor growth, animals were treated by oral gavage of either 100 µl of PEG400 (control, open squares) or Compound 62 at 3.5 mg/kg (circles), 10 mg/kg (inverted triangles), 35 mg/kg (triangles) or 100 mg/kg (squares) on odd numbered days. Whole body weight and tumor volume measurement were performed for up to 18 days.

The data are shown in FIGS. 1 and 2. In FIG. 1, Balb/c mice, 6-8 weeks old, were injected subcutaneously with $10^6$ JC cells suspended in phosphate-buffered saline. The SK inhibitors Compounds 62 and 57 were dissolved in PEG400 and administered to mice every-other day at a dose of 100 mg/kg. Body weights and tumor volumes were monitored daily. In FIG. 1, tumor growth is expressed as the tumor volume relative to day 1 for each animal.

As indicated in FIG. 1, tumor growth in animals treated with either SK inhibitor was significantly lower (>70% decreased at day 16) than tumor growth in control animals. Compounds 62 and 57 inhibited tumor growth relative to controls by 69 and 78%, respectively. The insert of FIG. 1 indicates the body weight of the animals during this experiment. No significant difference in the body weights of animals in the three groups was observed, indicating the lack of overt toxicity from either SK inhibitor.

Dose-response studies with Compound 62 demonstrated that the compound has antitumor activity when orally administered at doses of 35 kg/kg or higher (FIG. 2). No toxicity to the mice were observed at any dose.

Additional compounds of this invention were tested for their ability to inhibit the growth of JC adenocarcinoma cells in mice. The results are summarized in Table 9.

TABLE 9

In vivo antitumor activity of SK inhibitors.

| Compound | In vivo activity |
|---|---|
| 44 | active - ip |
| 51 | active - ip and po |
| 57 | active - po |
| 62 | active - ip and po |
| 107 | active - ip |

The indicated compounds were tested in the JC tumor model using either intraperitoneal (ip) or oral (po) administration. A compound is indicated as being active if it suppressed tumor growth by at least 60% relative to tumors in control animals.

Example 18

In Vivo Effects of SK Inhibitors on VEGF-Induced Vascular Permeability

The effects of VEGF on vascular leakage in vivo were measured as described by Miles and Miles (Miles et al., 1952, *J Physiol* 118: 228). Groups of female athymic nude mice (approximately 20 g) were given intraperitoneal injections of DMSO alone or Compound 62 (75 mg/kg) in a volume of 50 microliters. In some experiments, Compound 62 was administered by oral gavage at a dose of 100 mg/kg. After 30 minutes, 100 μL of 0.5% Evan's blue dye in PBS was administered by tail vein injection. Thirty minutes later, mice received the first of 3 sequential (every 30 minutes) intradermal injections of VEGF (400 ng in 20 μL of PBS per injection) on the left hind flank. As a control, similar injections of PBS were administered on the right hind flank. Thirty minutes after the last injection, leakage of the dye from the vasculature into the skin was assessed by measuring the length and width of the spots of blue-colored skin using calipers.

Figure 3:
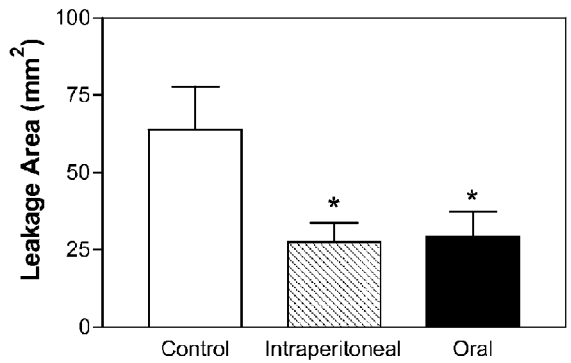
FIG. 3. Effects of Compound 62 on VEGF-induced vascular leakage. Nude mice were injected intraperitoneally with DMSO (Control, open bar) or 75 mg/kg of Compound 62 (hatched bar) or given 100 mg/kg of Compound 62 by oral gavage (solid bar). After 30 minutes, Evan's Blue dye was injected intravenously and the animals received subsequent subcutaneous injects of either PBS or 400 ng of VEGF. The areas of vascular leakage in each animal were then quantified. Values represent the mean±SD areas of vascular leakage. *p<0.01.

Administration of an intradermal bolus of VEGF results in leakage of the protein-bound dye into the skin indicating a local increase in vascular permeability. As indicated in FIG. 3, when Compound 62 was administered by either intraperitoneal injection or oral gavage one hour before the VEGF treatment, vascular leakage (determined three hours later) was markedly reduced. Therefore, SK inhibitors of this invention have the ability to suppress in vivo vascular leakage in response to VEGF.

Example 19

In Vivo Effects of SK Inhibitors on Diabetic Retinopathy

Male Sprague-Dawley rats weighing 150-175 g were used. Diabetes was produced by intraperitoneal injection of streptozotocin (65 mg/kg in citrate buffer) after overnight fasting. Sham-injected non-diabetic animals were also carried as controls. Blood glucose was measured three days post-injection and animals with blood glucose over 250 mg/dL were used as diabetic rats for the study. Blood glucose levels and body weights were monitored weekly throughout the study. On Day 45, retinal vascular permeability was measured in a group of control and diabetic rats (Antonetti et al., 1998, *Diabetes* 47: 1953, Barber et al., 2005, *Invest Ophthalmol Vis Sci* 46: 2210). Briefly, animals were weighed, anesthetized with ketamine/xylazine (80/0.8 mg/kg) and injected with fluorescein isothiocyanate-conjugated bovine serum albumin (FITC-BSA; Sigma catalog number A-9771) into the femoral vein. Following 30 minutes of FITC-BSA circulation, the rats were sacrificed by decapitation. Trunk blood was collected to measure the FITC-BSA concentration, and eyes were quickly enucleated. Each eye was placed in 4% paraformaldehyde for 1 hour and frozen in embedding medium in a bath of isopentane and dry ice. The paraffin-embedded eyes were sectioned on a microtome making 10 μm sections. Sections were dewaxed and viewed with an Olympus OM-2 fluorescence microscope fitted with a Sony CLD video camera. Fluorescence intensities of digital images were measured using Leica Confocal Software (Version 2.61, build 1538, LCS Lite, 2004). The average retinal intensity for each eye was then normalized to non-injected controls analyzed in the same manner and to the plasma fluorescence of the animal. Through serial sectioning of the eye, this technique enables quantification of varied vascular permeability in the retina (Antonetti et al., 1998, *Diabetes* 47: 1953, Barber et al., 2005, Ibid.).

The remaining control animals were maintained for an additional 6 weeks, i.e. until Day 87, as were the remaining diabetic rats that were divided into untreated, low-dose Compound 62 (25 mg/kg) or high-dose Compound 62 (75 mg/kg) treatment groups. Compound 62 was administered by intraperitoneal injection (dissolved in 0.375% Tween-80) 5 days per week from Day 45 to Day 87. On Day 87, all remaining animals were tested for retinal vascular permeability as described above. Sections were also stained for SK immunoreactivity using rabbit polyclonal antibodies, and counterstained for nuclei using Hoeschct stain.

Hyperglycemic rats were left untreated for 45 days to allow the progression of retinopathy. At that time, control and diabetic rats were evaluated for retinal vascular permeability by measuring the leakage of FITC-labeled BSA into the retina using quantitative image analyses. The diabetic animals had substantial increases in the leakage of the labeled BSA into the inner plexiform and outer nuclear layers of the retina. Quantification of the images indicated that there is an approximately 4-fold increase in the amount of FITC-BSA leakage in the retinas from diabetic rats. Therefore, substantial diabetes-induced vascular damage was present before the initiation of treatment with the SK inhibitor.

Figure 4:
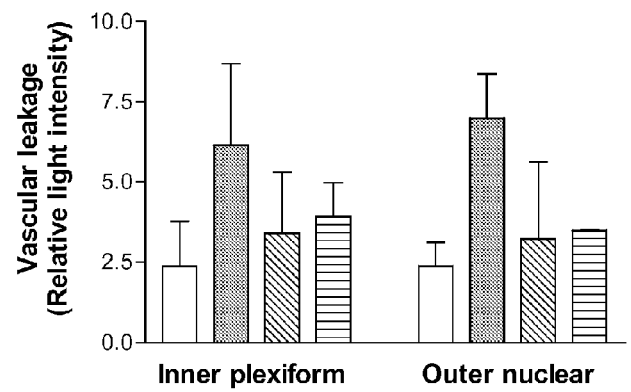
FIG. 4. Effects of Compound 62 on retinal vascular permeability in diabetic rats. Rats were made diabetic by administration of streptozotocin, and were left untreated for 45 days. From Day 45 through Day 87, Control (open bars) and Diabetic rats were treated with solvent (shaded bars) or Compound 62 at 25 mg/kg (horizontal-hatched bars) or 75 mg/kg (cross-hatched bars). On Day 87, retinal leakage in each animal was measured. Values represent the mean±sd for 3-5 rats per group.

All of the surviving rats were sacrificed on Day 87 and retinopathy was measured as the leakage of FITC-BSA into the retina. As indicated in FIG. 4, retinal vascular permeability in the diabetic rats was significantly elevated compared with the control rats. Diabetic animals that had been treated with the SK inhibitor Compound 62, at either dose, had substantially reduced levels of FITC-BSA leakage than did the untreated diabetic rats. This effect of the compound was manifested in both the inner plexiform layer and the outer nuclear layer of the retina.

Immunohistochemistry with the SK antibody described above was used to evaluate the expression of SK in the retinas of these animals. Fluorescence in the retinal pigment epithelium and the outer segment was non-specific since it was present in samples incubated in the absence of the SK antibody. Retinal sections from control rats had only low levels of specific staining for SK; whereas, SK expression was markedly elevated in the ganglion cell layer and in specific cell bodies and projections at the interface of the inner nuclear layer and the inner plexiform layer. Elevated SK expression was also observed in both the low-dose and the high-dose Compound 62-treated animals. Therefore, the long-term hyperglycemic state appears to be associated with elevation of retinal SK levels that are not normalized by treatment with the SK inhibitor. This expression data indicates that Compound 62 very effectively suppresses SK activity in the diabetic retina, thereby preventing the increased vascular permeability normally present in retinopathy.

Example 20

Inhibition of TNFα-Induction of NFκB by SK Inhibitors

Figure 5:
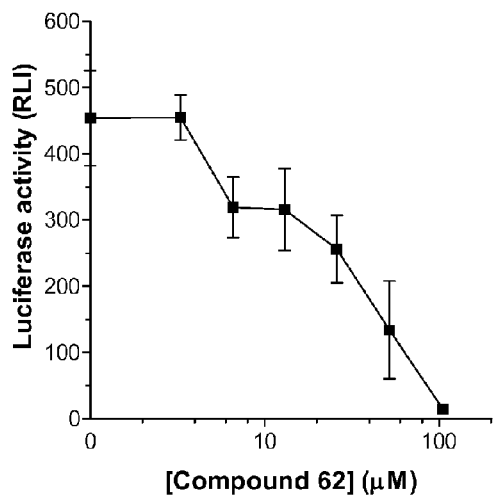
FIG. 5. Inhibition of TNFα-induced activation of NFκB by Compound 62. Fibroblasts transfected with a TNFα-responsive promoter linked to luciferase were treated with the indicated concentrations of Compound 62 and then treated with TNFα for 6 hours. The amount of luciferase expressed by the cells was then measured by luminescence. Values represent the mean±sd luciferase activity in triplicate samples in a typical experiment.

The excellent aqueous solubility of Compound 62 allowed it to be evaluated in an NFκB reporter cell line (FIG. 5). Fibroblasts transfected with an NFκB response element linked to luciferase produce high levels of luciferase upon exposure to TNFα. Activation of NFκB by TNFα was dose-dependently suppressed by the SK inhibitor, Compound 62.

Example 21

Inhibition of TNFα-Induced Adhesion Molecule Expression by SK Inhibitors

Like endothelial cells in the body, HUVECs will proliferate in response to several growth factors, and will respond to inflammatory cytokines such as TNFα and IL-1β. Western analyses were conducted with human endothelial cells to evaluate the effects of the SK inhibitors on signaling proteins known to be regulated by TNFα. In these experiments, the cells were serum-starved for 24 hours and then exposed to TNFα (100 ng/mL) for 6 hours. Cell lysates from treated cells were assayed for the adhesion molecules ICAM-1 and VCAM-1. TNFα caused marked increases in the expression levels of adhesion proteins involved in leukocyte recruitment, including ICAM-1 and VCAM-1. These effects of TNFα were inhibited by treating the cells with Compound 62, such that the induction of both proteins was completely abrogated by 25 µM Compound 62.

Example 22

Inhibition of TNFα-Induced Prostaglandin Synthesis by SK Inhibitors

Figure 6:
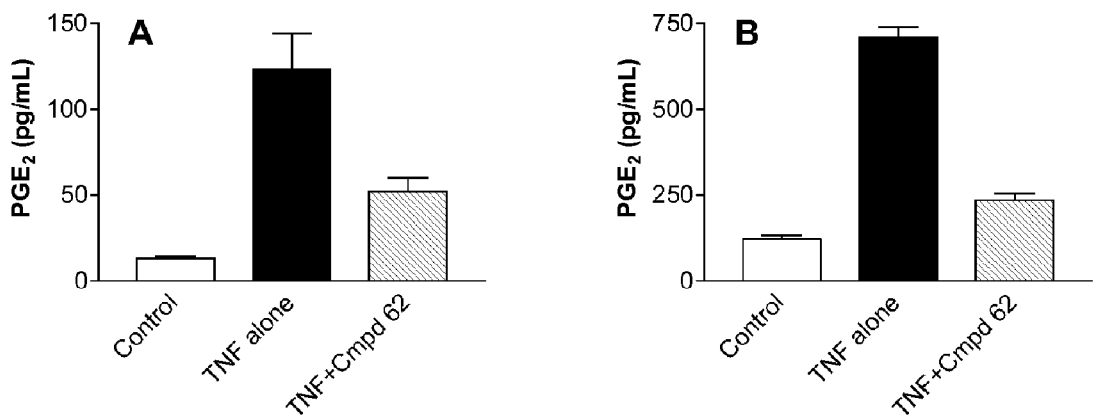
FIG. 6. Inhibition of TNFα-induced Cox-2 activity by Compound 62. Rat IEC6 cells (Panel A) or human endothelial cells (Panel B) were incubated for 18 hours with dimethylsulfoxide (DMSO) as a solvent control, or 100 ng of TNFα/mL in the presence of DMSO or 10 mg/mL of Compound 62. Levels of $PGE_2$ secreted into the medium were quantified by ELISA. Values represent the mean±sd for triplicate samples in a typical experiment.

To determine the effects of the SK inhibitors on Cox-2 activity, an ELISA assay was used to measure $PGE_2$ production by IEC6 rat intestinal epithelial cells and human endothelial cells treated with TNFα. Exposure of either type of cell to TNFα resulted in marked increases in Cox-2 activity, measured as the production of $PGE_2$ (FIG. 6). This induction of Cox-2 activity by TNFα was strongly suppressed by Compound 62.

Overall, these data demonstrate that inhibition of SK will be effective in blocking the inflammatory cascade in cells initiated by TNFα. This is expected to alleviate the pathology of diseases several inflammatory diseases, including IBD, arthritis, atherosclerosis and asthma.

Example 23

In Vivo Effects of SK Inhibitors in an Acute Model of Inflammatory Bowel Disease We have conducted experiments with SK inhibitors using the dextran sulfate sodium (DSS) model of IBD. In these experiments, male C57BL/6 mice were provided with standard rodent diet and water ad libitum. After their acclimation, the animals were randomly divided into groups of 5 or 6 for DSS (40,000 MW from ICN Biomedicals, Inc., Aurora, Ohio)—and drug-treatment. The SK inhibitors were dissolved in PEG400, and given once daily by oral gavage in a volume of 0.1 mL per dose. Dipentum, an FDA-approved anti-colitis drug whose active ingredient, olsalazine, is converted to 5-aminosalicylic acid in vivo, was used as a positive control. The mice were given normal drinking water or 2% DSS and treated orally with an SK inhibitor or Dipentum at a dose of 50 mk/kg daily. The body weight of each animal was measured each day, and the Disease Activity Index (DAI) was scored for each animal on Days 4-6. On Day 6, the animals were sacrificed by cervical dislocation and the entire colon was removed and measured to the nearest 0.1 cm. Portions of the colons were then fixed, sectioned and their histologies were assessed on a blinded basis to determine their Histology Score. Other portions of the colons were used for biochemical analyses of inflammation markers.

Figure 7:
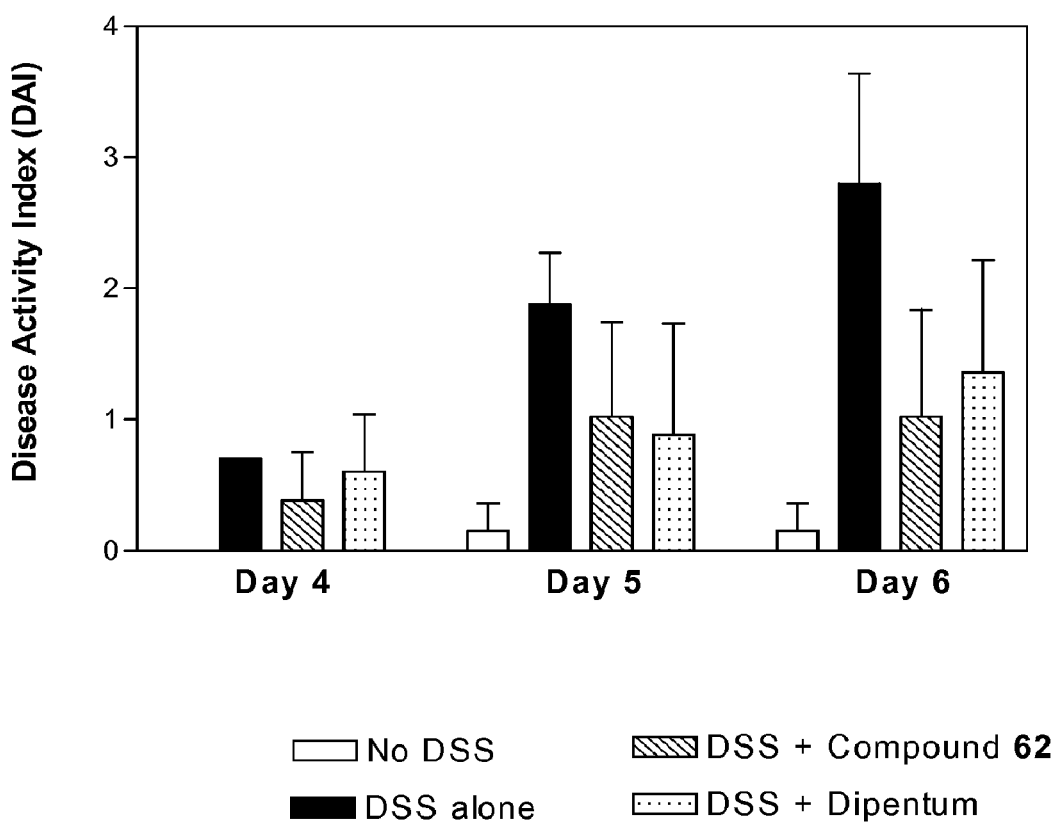
FIG. 7. Effects of Compound 62 and Dipentum on the DAI in the acute DSS-colitis model. C57BL/6 mice were treated for 6 days as follows: normal drinking water and daily oral administration of PEG (No DSS), 2% DSS in the drinking water and daily oral administration of PEG (DSS alone); 2% DSS in the drinking water and daily oral administration of 50 mg/kg Compound 62 in PEG (DSS+Compound 62), or 2% DSS in the drinking water and daily oral administration of 50 mg/kg Dipentum in PEG (DSS+Dipentum). On the indicated day, the Disease Activity Index was calculated for each group. Values represent the mean±sd for 5-6 mice per group.

The DAI monitors weight loss, stool consistency and blood in the stool and is a measure of disease severity. Animals receiving normal drinking water and PEG as a solvent control had very low DAIs throughout the experiment (FIG. 7). Exposure of the mice to DSS in their drinking water markedly induced IBD symptoms, including weight loss and the production of loose, bloody stools. The intensity of the disease progressively increased from Day 4 to the time the mice were sacrificed on Day 6. Treatment of the animals receiving DSS with Compound 62 or Dipentum reduced the intensity of the IBD manifestations in the mice, most dramatically on Day 6. The SK inhibitors and Dipentum were essentially equivalent in their abilities to reduce the DAI of mice receiving DSS. It should be noted that this acute model produces rapid and dramatic symptoms of IBD, making it a very stringent assay for drug testing.

Figure 8:
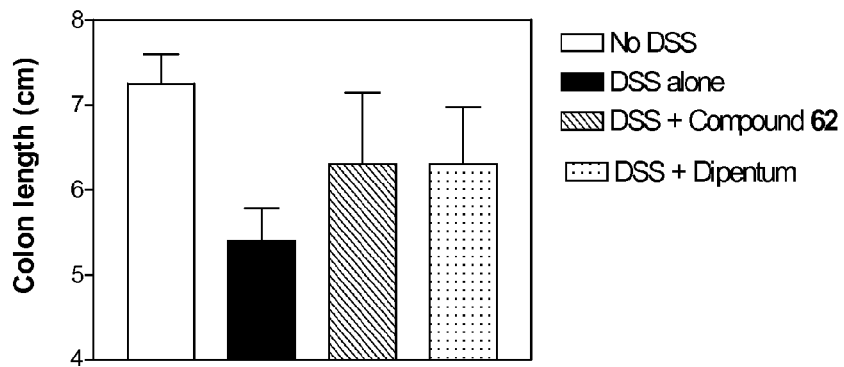
FIG. 8. Effects of Compound 62 and Dipentum on colon length in the acute DSS-colitis model. Mice from the experiment described in FIG. 7 were sacrificed on Day 6, and the colon was harvested from each animal and measured. Data represent the mean±sd colon length.

On Day 6, the animals were sacrificed by cervical dislocation and the entire colon was measured to assess shortening due to scarring and damage, and then fixed, sectioned and examined histologically on a blinded basis. Compared with the water control group, the colons of mice treated with DSS and PEG were significantly shortened (FIG. 8). DSS-treated mice that were also treated with Compound 62 or Dipentum had colons of intermediate length, indicating substantial protection by the drugs. Again, the response to either of the SK inhibitors was at least as good as that of mice treated with Dipentum.

Histological examination of colon sections from the various treatment groups were consistent with the DAI endpoint, revealing marked damage in the DSS-alone group that was reduced or negated in the SK inhibitor-treated animals. Colons from water-treated control animal demonstrated normal morphology, while colons from DSS alone-treated mice were severely inflamed and damaged. Numerous neutrophils were present throughout the section, along with severely damaged crypts, and moderate inflammatory infiltration with submucosal edema. Colons from animals treated with DSS and Compound 62 showed no or mild crypt damage, no or low levels of inflammatory cell infiltration and no edema in the submucosa.

Figure 9:
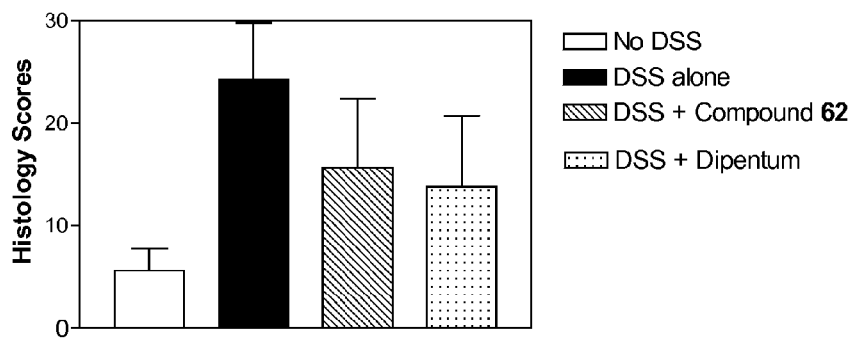
FIG. 9. Effects of Compound 62 and Dipentum on the colon Histology Score in the acute DSS-colitis model. Mice from the experiment described in FIG. 7 were sacrificed on Day 6, and the colon was harvested from each animal and the Histology Score was determined Values represent the mean±sd for 5-6 mice per group.

As a quantifiable measure of damage, the colons were graded for their Histology Score, which is based on inflammation severity, inflammation extent, crypt damage and the percentage of surface area demonstrating the characteristic. These morphologies were scored on a blinded basis. As indicated in FIG. 9, animals receiving DSS in their drinking water had substantially higher Histology Scores (representing moderate-to-severe IBD) than animals receiving normal drinking water (which had some mild inflammation, possibly due to the PEG vehicle). As with the other assays, the Histology Scores of mice given an SK inhibitor or Dipentum were consistently lower than the DSS-alone animals, although not all animals were fully protected. DAI scores and histology scores correlated well for the individual animals, confirming that the DAI score as an excellent indicator of colon inflammation and damage.

Figure 10:
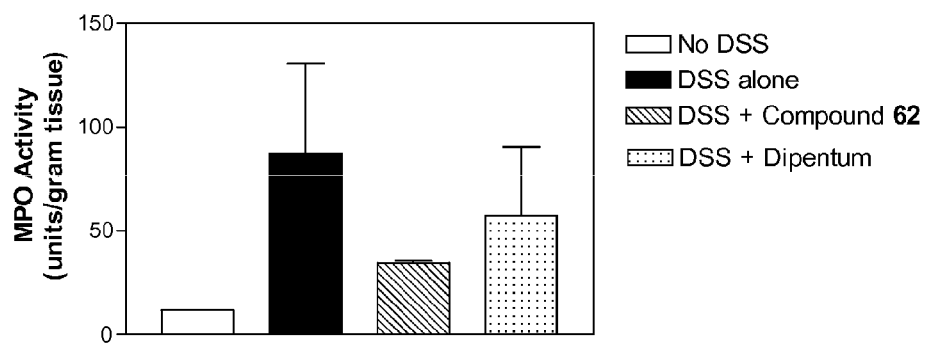
FIG. 10. Effects of Compound 62 and Dipentum on neutrophil infiltration into the colon in the acute DSS-colitis model. Myeloperoxidase activity from the colons of the animals described in FIG. 7 was measured. Values the mean±sd MPO activity in units per gram of tissue.

Myeloperoxidase (MPO) activity, which is reflective of neutrophil influx into the colon, is often used as measure of inflammation, and was assayed in the colons of the mice from the DSS-colitis studies. As indicated in FIG. 10, MPO activity was highly elevated in the DSS-alone animals compared to water controls. The increase in MPO activity was markedly attenuated in mice receiving daily doses of Compound 62 or Dipentum. This reduction in the activity of the neutrophil marker is consistent with the decreased occurrence of granulocytes observed in the H&E-stained colon sections. Therefore, the level of colonic MPO appears to be an excellent biomarker for the extent of tissue infiltration by inflammatory leukocytes.

Figure 11:
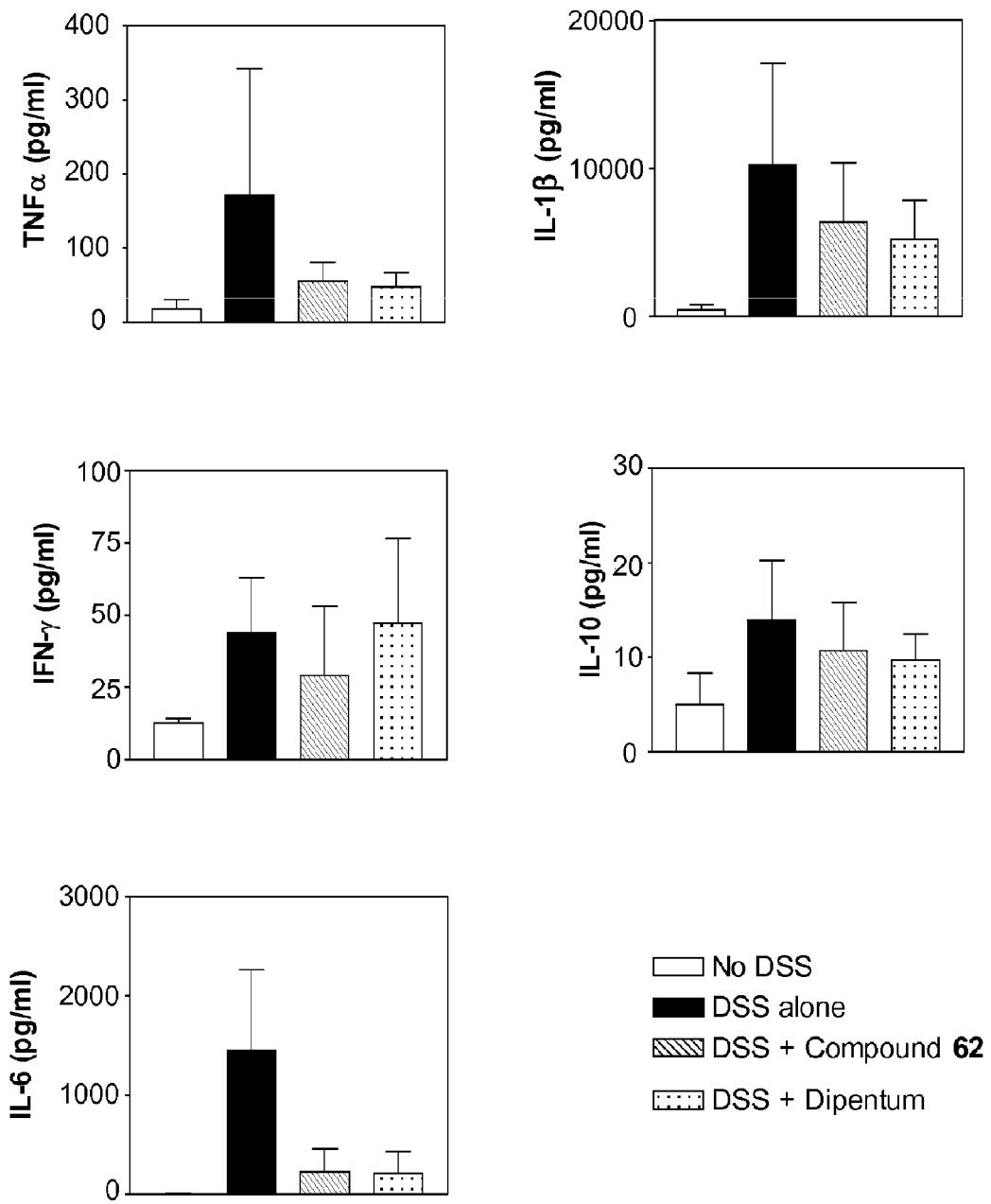
FIG. 11. Effects of Compound 62 and Dipentum on colonic cytokine levels in the acute DSS-colitis model. Colon samples from mice described in FIG. 7 were extracted and assayed for the levels of the indicated cytokines. Values represent the mean±sd amount of each cytokine in 4-5 samples per group.

Several cytokines involved in inflammation were measured using the Luminex 100 System that allows the quantification of multiple cytokines and growth factors in a small sample volume. We examined the Th1 cytokine IFN-$\gamma$, the regulatory IL-10 cytokine, as well as the macrophage-derived pro-inflammatory cytokines, TNF$\alpha$, IL-1$\beta$, IL-6 in colon samples from mice in the DSS model of colitis. FIG. 11 depicts the results of these assays, and indicates that DSS-treatment promoted the accumulation of all of the cytokines in the colon. Importantly, the elevations of all of the pro-inflammatory proteins, i.e. IFN-$\gamma$, IL-1$\beta$, IL-6 and TNF$\alpha$, were attenuated in mice treated with either an SK inhibitor or Dipentum. Conversely, levels of the anti-inflammatory cytokine IL-10 were not suppressed by the SK inhibitors.

Figure 12:
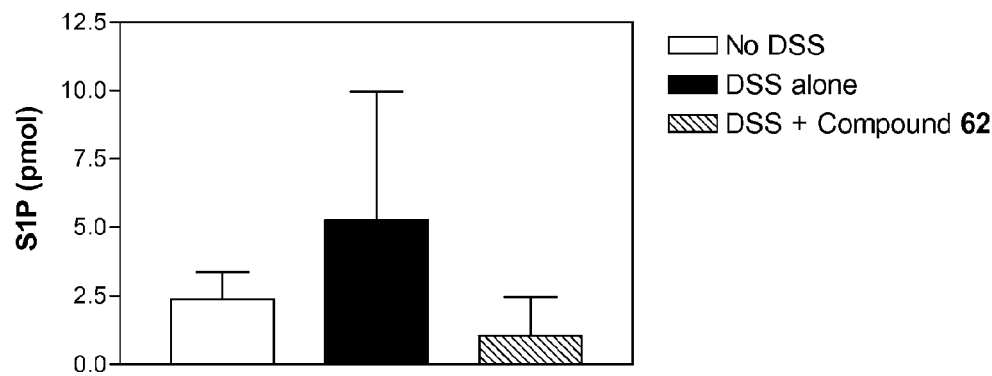
FIG. 12. Effects of Compound 62 on S1P levels in the colons of the animals in the DSS-colitis model. Colon samples from mice described in FIG. 7 were extracted and assayed for the levels of S1P by LC/MS/MS. Values represent the mean±sd for 4-5 samples per group.

As a final measure of the effects of the SK inhibitors in this acute model, S1P levels were assayed in the colons of the DSS-treated animals using an LC-MS/MS method. This technique allows us to examine correlations between biologic activity and changes in S1P levels in animals treated with the SK inhibitors. Samples of colons from animals from the DSS-colitis experiments were homogenized in cold PBS, spiked with internal standards ($C_{17}$ analogs of sphingosine and S1P) and processed by liquid-liquid extraction. Ratios of analyte to internal standard for each sphingolipid were determined S1P levels were markedly higher in the colons from DSS-treated mice as compared to the water controls (FIG. 12). Importantly, animals that were treated with Compound 62 had markedly lower levels of colonic S1P than the DSS-alone samples.

Example 24

In Vivo Effects of SK Inhibitors in a Chronic Model of Inflammatory Bowel Disease A 35-day model of IBD was used to evaluate the effectiveness of the SK inhibitors in mice that experience multiple cycles of DSS-induced inflammation. This chronic model is similar to the acute model, except that the DSS concentration in the drinking water is lower and animals receive periodic exposure to DSS (DSS on days 1-7, water on Days 8-13, DSS on day 14-21, water on Days 22-27 and then DSS until the completion of the study on Day 35). In these experiments, treatment of the mice with an SK inhibitor or Dipentum began on Day 28 and continued daily until the completion of the study. The DAI index was monitored every other day until Day 28 and then daily until Day 35. Animals were sacrificed on Day 35, and changes in the colon length and cytokine profiles were measured.

Figure 13:
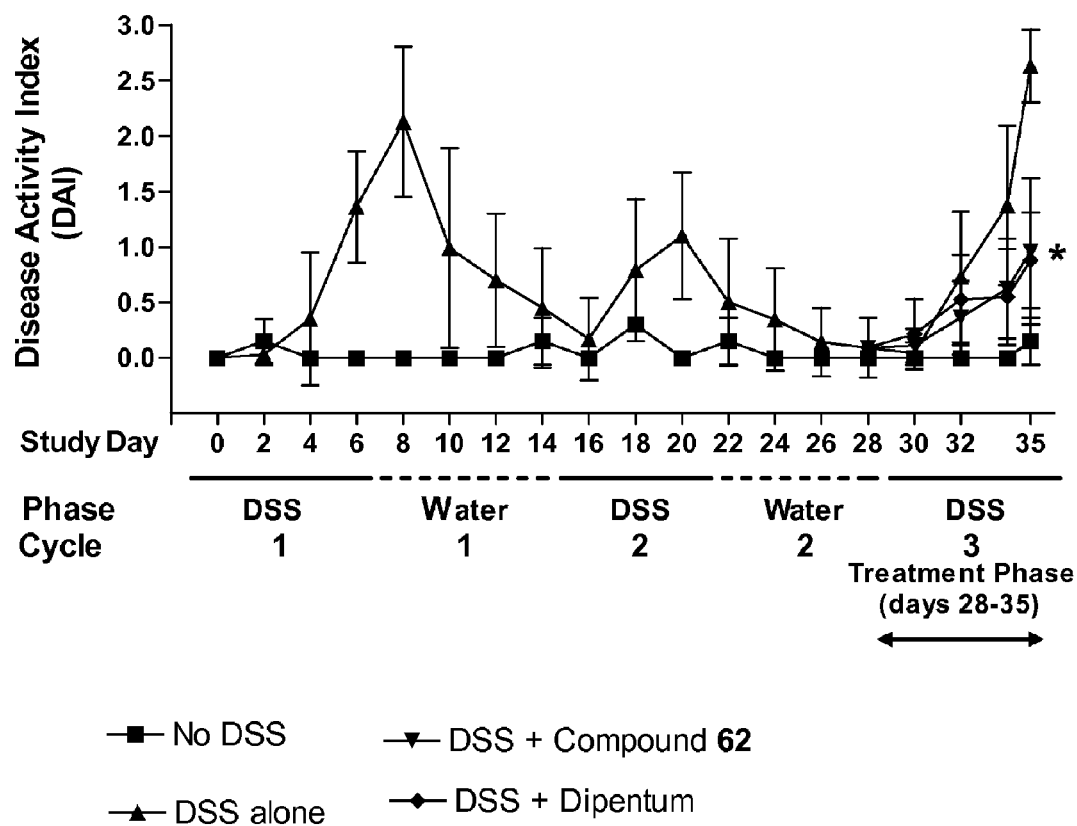
FIG. 13. Effects of Compound 62 on the DAI in the chronic DSS-colitis model. Mice received 2 cycles (7 days per cycle) of DSS (1.5% cycle 1 and 1% cycle 2), 2 cycles of normal drinking water and were randomized by DAI on Day 28 into groups of 8 mice. The mice were then treated as follows: No DSS (■)—normal drinking water and orally dosed with PEG400 every day for 7 days (water control); DSS alone (▲)—drinking water containing 1.5% DSS and orally dosed with PEG daily for 7 days; DSS+Compound 62 (▼)—drinking water containing 1.5% DSS and orally dosed with Compound 62 (50 mg/kg) every day for 7 days; DSS+Dipentum (♦)—drinking water containing 1.5% DSS and orally dosed with Dipentum (50 mg/kg). *p<0.001 versus No DSS group.

Cyclic exposure of mice to DSS in their drinking water caused reversible increases in the DAI (FIG. 13). Treatment of the mice with Compound 62 or Dipentum during the third exposure to DSS significantly suppressed the increase in DAI experienced by the control mice ($P<0.001$ for all three compounds on Day 35).

The colon lengths of DSS-treated mice were significantly shorter than the water-treated control animals (4.9±0.2 cm vs. 7.8±0.3 cm) reflecting inflammation-induced scarring. As in the acute model, the colons of animals treated with Compound 62 or Dipentum were of intermediate length (6.2±0.2 and 6.1±0.2 cm, respectively). This is a significant finding since the animals were untreated for the first and second DSS cycles. Therefore, suppression of inflammation-induced colon contraction can be reversed by effective anti-IBD drugs.

Immunohistochemistry revealed that SK expression was present in low levels in the colons of control, non-DSS treated mice. SK expression was elevated in the colons of DSS treated mice compared to water controls with this expression clearly reduced in DSS mice also receiving Compound 62.

Figure 14:
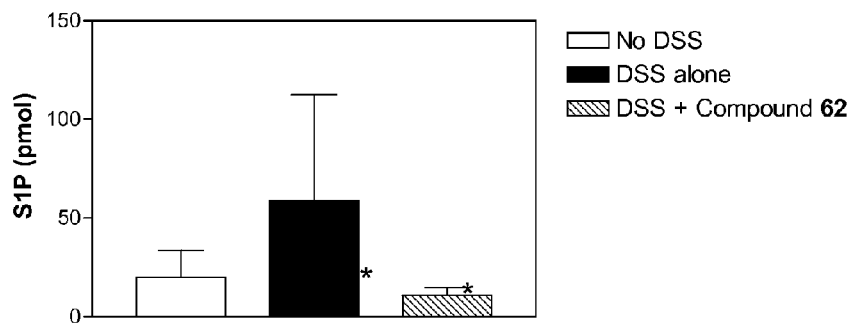
FIG. 14. Effects of Compound 62 on S1P levels in the colons of the animals in the chronic DSS-colitis model. Colon samples from mice described in FIG. 13 were extracted and assayed for the levels of S1P by LC/MS/MS. Values represent the mean±sd for 8 samples per group; * p<0.05 versus No DSS group.

S1P levels in the colons of the chronic colitis model mice were assessed in an identical manner as described for the acute model, and revealed results similar to those in the acute model with elevated S1P levels in DSS alone treated mice as compared to water controls (FIG. 14). Treatment with Compound 62 (oral 50 mg/kg daily; 7 days prior to sacrifice) resulted in significant reductions of S1P levels (FIG. 14).

Figure 15:
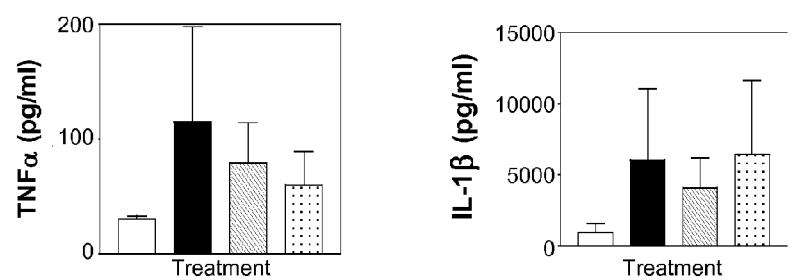
FIG. 15. Effects of Compound 62 and Dipentum on colonic cytokine levels in the chronic DSS-colitis model. Colon samples from mice described in FIG. 13 were extracted, and assayed for the levels of the indicated cytokines. Values represent the mean±SD amount in 8 samples per group.
Figure 15:
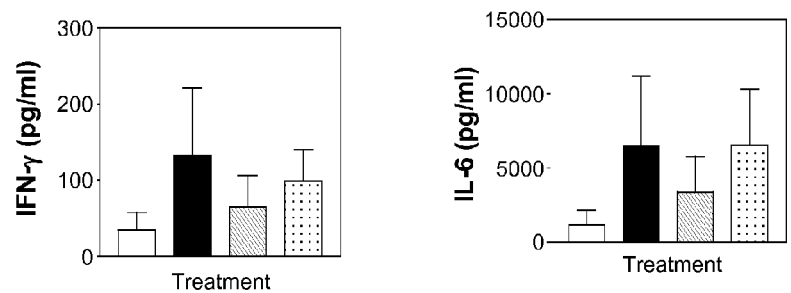
Figure 15:
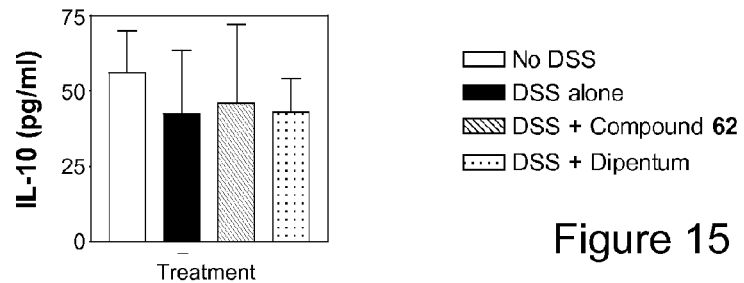

The levels of the pro-inflammatory cytokines TNF$\alpha$, IL-1$\beta$, IFN-$\gamma$ and IL-6 were substantially increased in the colons of mice treated chronically with DSS; whereas, the level of IL-10 was unchanged (FIG. 15). Mice treated with Compound 62 during the final DSS cycle had reduced levels of the pro-inflammatory cytokines, while animals treated with Dipentum expressed cytokine profiles equivalent to the DSS-alone group. This may reflect the presence of high numbers of resident immune cells in the colons of mice exposed chronically to DSS. However, the elevation in cytokine levels in the SK inhibitor-treated mice does not result in increased DAI or colon shortening, indicating that signaling induced by the inflammatory cytokines had been blocked.

Figure 16:
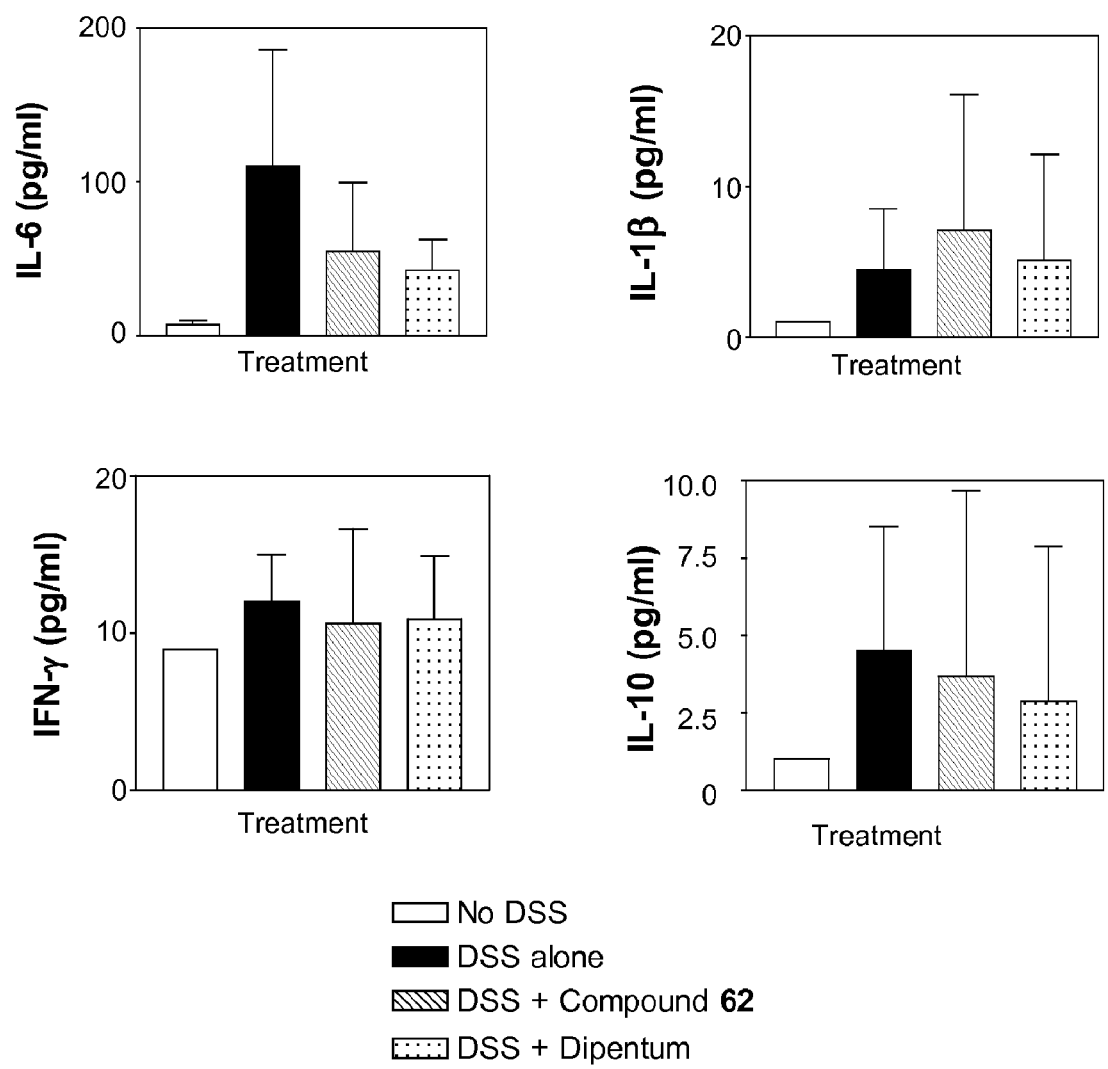
FIG. 16. Effects of Compound 62 and Dipentum on serum cytokine levels in the chronic DSS-colitis model. Serum from mice described in FIG. 13 was assayed for the levels of the indicated cytokines. Values represent the mean±SD amount in 8 samples per group.

For comparison, the levels of the same cytokines in the serum of the mice at the time of sacrifice were also determined. As indicated in FIG. 16, the circulating levels of these cytokines are markedly lower than the colonic levels reflecting the local inflammation in this model. DSS increased the circulating levels of IL-1β, IFN-γ, IL-6 and IL-10, while TNFα remained below the detection limit of the assay. None of the test compounds affected the circulating levels of IL-1β or INF-γ; however, both Compound 62 and Dipentum reduced the serum level of IL-6. Therefore, serum levels of IL-6 may be a useful pharmacodynamic marker for the anti-inflammatory effects of the SK inhibitors during clinical testing.

Example 25

In Vivo Effects of SK Inhibitors in the Collagen-Induced Arthritis Model in Mice The anti-arthritis activities of the SK inhibitor Compound 62 were assessed in the Collagen-Induced Arthritis (CIA) model. Female DBA/1 mice were injected subcutaneously in the tail with chicken immunization-grade type II collagen (Chondrex) emulsified in complete Freund's adjuvant (Sigma) at 2 mg/mL. Three weeks later, the mice received a collagen booster in incomplete Freund's adjuvant and were monitored daily thereafter for arthritic symptoms. Once mice reached a threshold paw thickness and clinical score, they were randomized into the following treatment groups: Compound 62 (100 mg/kg given orally each day for 6 days per week) or vehicle (0.375% Tween-80 given under the same schedule). The severity of disease in each animal was quantified by measurement of the hind paw volume with digital calipers. Each paw was scored based upon perceived inflammatory activity, in which each paw receives a score of 0-3 as follows: 0=normal; 1=mild, but definite redness and swelling of the ankle or wrist, or apparent redness and swelling limited to individual digits, regardless of the number of affected digits; 2=moderate redness and swelling of the ankle and wrist and 3=severe redness and swelling of the entire paw including digits, with an overall score ranging from 0-12. Differences among treatment groups were tested using ANOVA.

Figure 17:
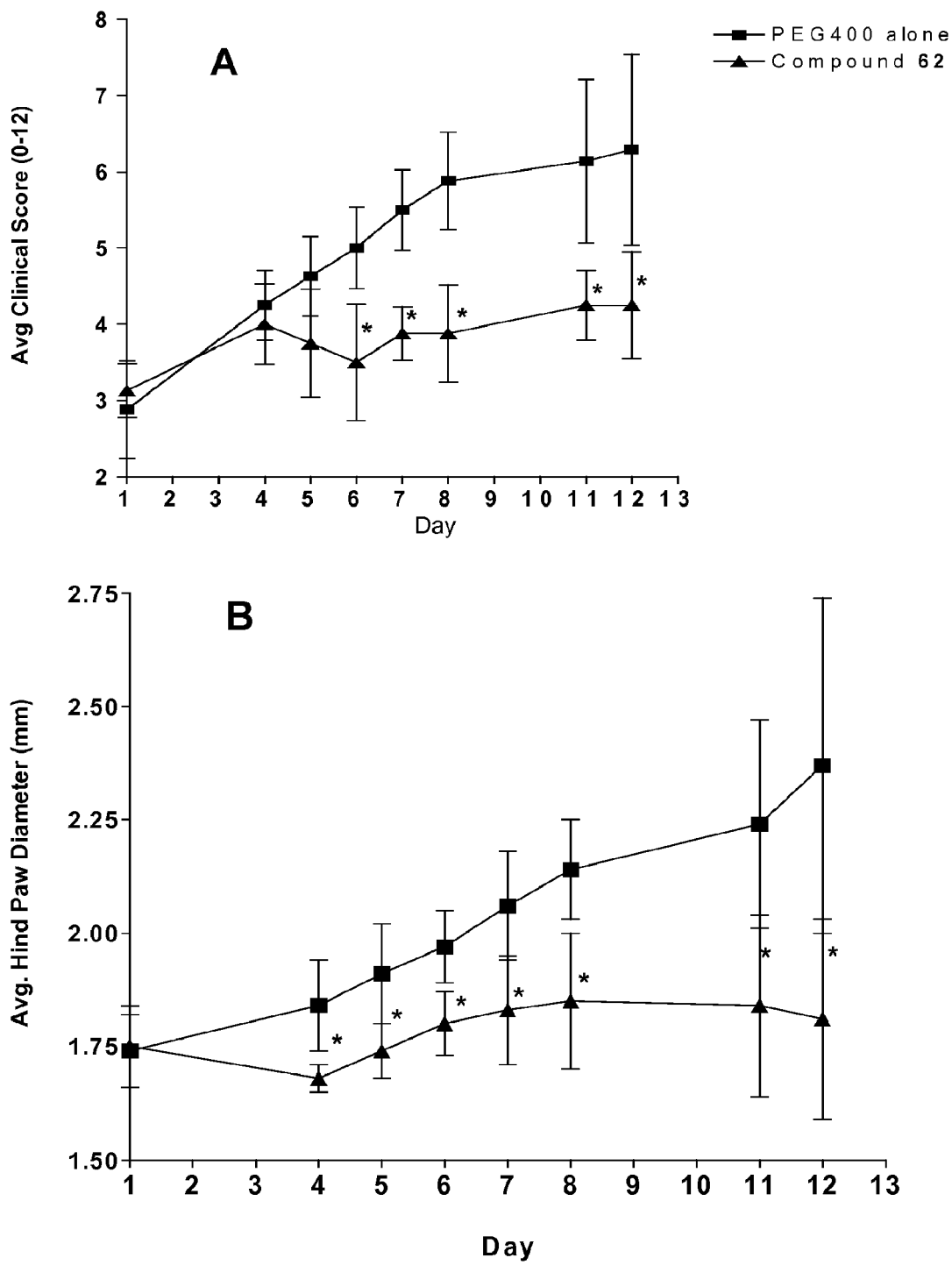
FIG. 17. Effects of Compound 62 on disease progression in the CIA model in mice. Female DBA/1 mice were injected with collagen, boosted after 3 weeks and then monitored for symptoms of arthritis. Upon disease manifestation, groups of mice were treated for 12 days as follows: (▲) Compound 62 (100 mg/kg given orally each day for 6 days per week); or (■) vehicle (PEG400 given under the same schedule). On the indicated Day of treatment, the average clinical score (A) and the average hind paw diameter (B) was determined * p≤0.05 versus PEG400 alone group.
Figure 18:
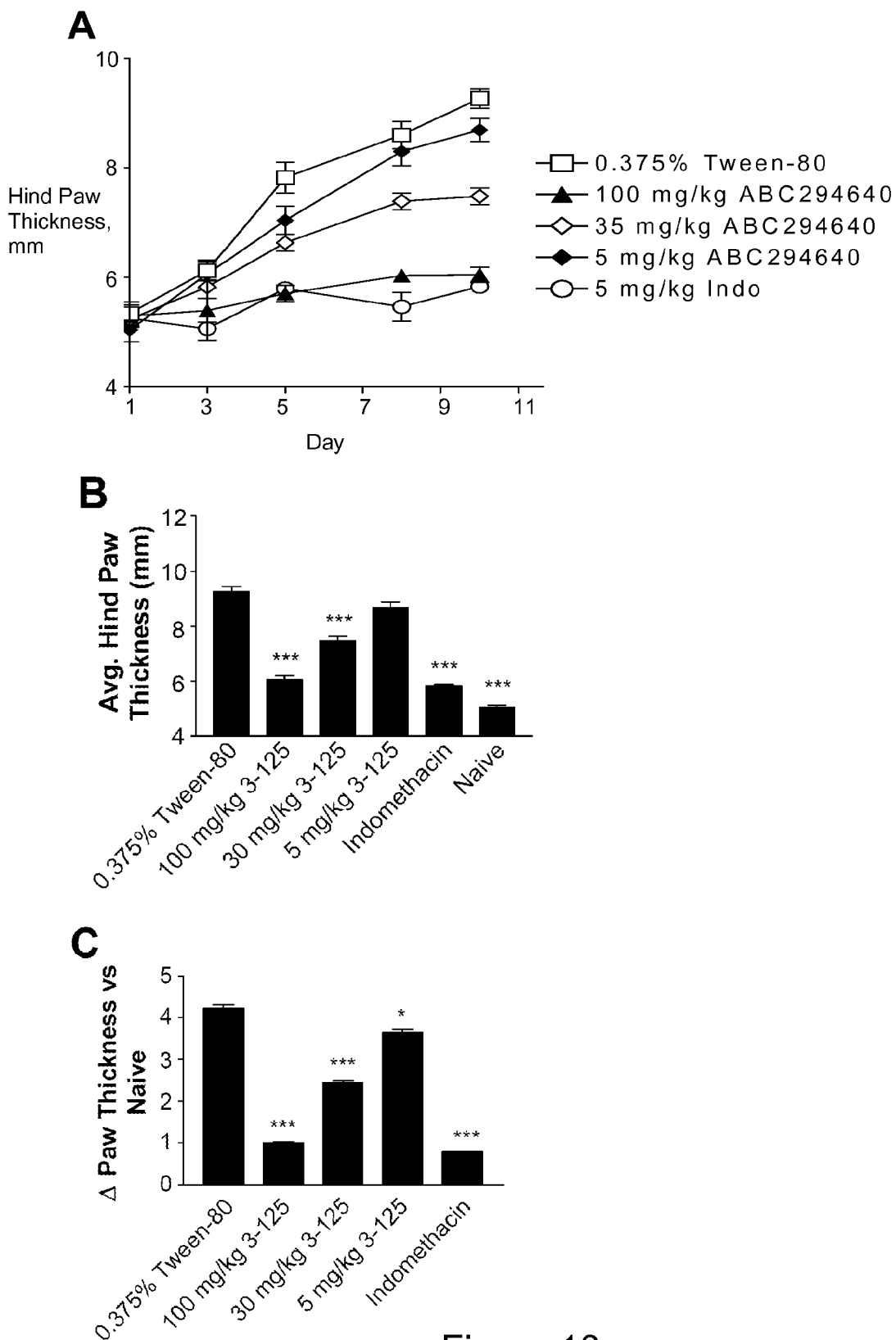
FIG. 18. Effects of Compound 62 on disease progression in the adjuvant-induced arthritis model in rats. Male Lewis rats were injected subcutaneously with *Mycobacterium butyricum*, and symptoms of immune reactivity were present after 2 weeks. Responsive rats were randomized into treatment groups (n=8 per group), and received oral daily doses of: solvent alone (0.375% Tween-80); 100 mg/kg Compound 62 (ABC294640); 35 mg/kg Compound 62; or 5 mg/kg Compound 62, or intraperitoneal injections of indomethacin (5 mg/kg) every other day. The severity of disease in each animal was quantified by measurement of the hind paw thickness. Panel A. Time course of hind paw arthritic response. Panel B. Final day (Day 10) hind paw thickness measurements. Panel C. Change in paw thickness of respective group versus non-arthritic rats (naive) at Day 10. *, p<0.05; ***, p<0.001 versus solvent alone group.

As indicated in FIG. 17, treatment with either SK inhibitor dramatically slowed the inflammation response, measured as either the Average Clinical Score (FIG. 10A) or the Average Hind Paw Diameter (FIG. 10B), with significant decreases beginning at Day 5 of treatment for both endpoints. By the end of the experiment on Day 12, Compound 62 caused a 90% reduction in the increase in hind paw thickness, and a 67% reduction in clinical score compared with vehicle-treated mice. Since a 30% reduction in symptoms is considered demonstrative of anti-arthritic activity in this assay, the SK inhibitor surpasses the criteria for efficacy in this model.

On Day 12, the mice were euthanized and their hind limbs were removed, stripped of skin and muscle, formalin-fixed, decalcified and paraffin-embedded. The limbs were then sectioned and stained with hematoxylin/eosin. Tibiotarsal joints were evaluated histologically for severity of inflammation and synovial hyperplasia. Collagen-Induced Arthritis resulted in a severe phenotype compared with non-induced mice, manifested as severe inflammation and synovial cell infiltration, as well as significant bone resorption. Mice that had been treated with Compound 62 had significantly reduced histologic damage, correlating with the paw thickness and clinical score data.

Example 26

In Vivo Effects of SK Inhibitors in the Adjuvant-Induced Arthritis Model in Rats Adjuvant-induced arthritis is another widely used assay that recapitulates many features of human rheumatoid arthritis, and so is useful in the evaluation of new drug candidates. Age- and weight-matched male Lewis rats (150-170 g) were injected subcutaneously in the tail with 1 mg of *Mycobacterium butyricum* (Difco, killed dried) suspended in 0.1 ml of light mineral oil. Symptoms of immune reactivity were present after 2 weeks. Responsive rats were randomized into treatment groups, and received oral daily doses (1 ml) of: solvent alone (0.375% Tween-80); 100 mg/kg Compound 62; 35 mg/kg Compound 62; or 5 mg/kg Compound 62, or intraperitoneal injections of indomethacin (5 mg/kg) every other day as a positive control. The severity of disease in each animal was quantified by measurement of the hind paw thickness. As above, a reduction of 30% or greater was considered to be an indication of anti-inflammatory activity in this model.

As indicated in FIG. 17, solvent alone-treated rats demonstrated a progressive increase in paw thickness over the course of the next 10 days. Compound 62 inhibited this arthritic response in a dose-dependent manner, with the highest dose having similar therapeutic efficacy as indomethacin. Compound 62 at doses of 5, 35 or 100 mg/kg resulted in 13, 42 and 76 percent reductions in the arthritic response, respectively. Thus, Compound 62 is highly effective in this arthritis model.

What is claimed is:

1. A method of inhibiting sphingosine kinase in a patient in need of such inhibition, the method comprising administering to the patient a compound of Formula I:

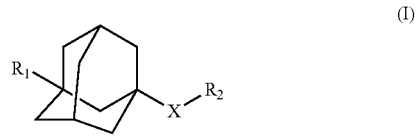

or a pharmaceutically acceptable salt thereof, wherein:
X is —C($R_3$,$R_4$)N($R_5$)— or —C(O)N($R_4$)—;
$R_1$ is phenyl substituted with 1 to 5 groups that are independently halogen, haloalkyl, CONR'R", —OC(O)NR'R", —NR'C(O)R", —$CF_3$, —$OCF_3$, —CN, —$CO_2$H, —S-alkyl, —SOR'R", $SO_2$R', wherein R' and R" are independently H or ($C_1$-$C_6$)alkyl, and wherein each alkyl portion of a substituent is optionally further substituted with 1, 2, or 3 groups independently selected from halogen, CN, OH, and $NH_2$;
$R_2$ is aryl, -alkyl-aryl, heteroaryl, -alkyl-heteroaryl, heterocycloalkyl or -alkyl-heterocycloalkyl;
$R_3$ is H or -alkyl;

wherein the alkyl and ring portion of each of the above $R_2$ and $R_3$ groups is optionally substituted with up to 5 groups that are independently ($C_1$-$C_6$)alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or ($C_1$-$C_6$)alkyl, and wherein each alkyl portion of a substituent is optionally further substituted with 1, 2, or 3 groups independently selected from halogen, CN, OH, and NH$_2$; and $R_4$ and $R_5$ are independently H or alkyl.

2. A method according to claim 1 wherein X is —C(O)N($R_4$)—.

3. A method according to claim 2 wherein $R_4$ is H.

4. A method according to claim 1 wherein X is —C($R_3$,$R_4$)N($R_5$)—.

5. A method according to claim 4 wherein $R_3$ is H or alkyl and $R_4$ is H.

6. A method according to claim 1 wherein $R_1$ is aryl substituted with one or two halogen groups.

7. A method according to claim 1 wherein $R_2$ is aryl or -alkylaryl.

8. A method according to claim 7 wherein $R_2$ is phenyl, benzyl, phenethyl, or 3-phenylpropyl, wherein the alkyl and ring portion of the above $R_2$ groups is optionally substituted with up to 5 groups that are independently ($C_1$-$C_6$)alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or ($C_1$-$C_6$)alkyl, and wherein each alkyl portion of a substituent is optionally further substituted with 1, 2, or 3 groups independently selected from halogen, CN, OH, and NH$_2$.

9. A method according to claim 1 wherein $R_2$ is heterocycloalkyl or -alkyl-heterocycloalkyl.

10. A method according to claim 9 wherein $R_2$ is piperidinyl, piperazinyl, 2-(piperazin-1-yl)ethyl, 2(pyrrolidin-2-yl)ethyl, 3-(pyrrolidin-1-yl)propyl, or 2-(morpholin-4-yl)ethyl, wherein the alkyl and ring portion of the above $R_2$ groups is optionally substituted with up to 5 groups that are independently ($C_1$-$C_6$)alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or ($C_1$-$C_6$)alkyl, and wherein each alkyl portion of a substituent is optionally further substituted with 1, 2, or 3 groups independently selected from halogen, CN, OH, and NH$_2$.

11. A method according to claim 1 wherein $R_2$ is heteroaryl or alkylheteroaryl.

12. A method according to claim 11 wherein $R_2$ is pyridin-4-ylmethyl, pyridin-4-ylethyl, pyridin-3-ylmethyl, 1H-indol-5-yl, 1H-tetrazol-5-yl, 3H-imidazol-4-ylmethyl, benzothiazol-2-yl, carbazol-3-yl, benzooxazol-2-yl, purin-6-yl, or thiophen-2-yl, wherein the alkyl and ring portion of the above $R_2$ groups is optionally substituted with up to 5 groups that are independently ($C_1$-$C_6$)alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or ($C_1$-$C_6$)alkyl, and wherein each alkyl portion of a substituent is optionally further substituted with 1, 2, or 3 groups independently selected from halogen, CN, OH, and NH$_2$.

13. A method according to claim 1, wherein the compound is:

3-(4-Chloro-phenyl)-adamantane-1-carboxylic acid phenylamide;

3-(4-Chloro-phenyl)-adamantane-1-carboxylic acid (4-hydroxy-phenyl)-amide;

Acetic acid 4-{[3-(4-chloro-phenyl)-adamantane-1-carbonyl]-amino}-phenyl ester;

3-(4-Chloro-phenyl)-adamantane-1-carboxylic acid (2,4-dihydroxy-phenyl)-amide;

3-(4-Chloro-phenyl)-adamantane-1-carboxylic acid (3-hydroxymethyl-phenyl)-amide;

3-(4-Chloro-phenyl)-adamantane-1-carboxylic acid (4-cyanomethyl-phenyl)-amide;

3-(4-Chloro-phenyl)-adamantane-1-carboxylic acid benzylamide;

3-(4-Chloro-phenyl)-adamantane-1-carboxylic acid 4-tert-butyl-benzylamide;

3-(4-Chloro-phenyl)-adamantane-1-carboxylic acid 4-methylsulfanyl-benzylamide;

3-(4-Chloro-phenyl)-adamantane-1-carboxylic acid 3-trifluoromethyl-benzylamide;

3-(4-Chloro-phenyl)-adamantane-1-carboxylic acid 4-trifluoromethyl-benzylamide;

3-(4-Chloro-phenyl)-adamantane-1-carboxylic acid 3,5-bis-trifluoromethyl-benzylamide;

3-(4-Chloro-phenyl)-adamantane-1-carboxylic acid 3-fluoro-5-trifluoromethyl-benzylamide;

3-(4-Chloro-phenyl)-adamantane-1-carboxylic acid 2-fluoro-4-trifluoromethyl-benzylamide;

3-(4-Chloro-phenyl)-adamantane-1-carboxylic acid 3,5-difluoro-benzylamide;

3-(4-Chloro-phenyl)-adamantane-1-carboxylic acid 3,4-difluoro-benzylamide;

3-(4-Chloro-phenyl)-adamantane-1-carboxylic acid 3,4,5-trifluoro-benzylamide;

3-(4-Chloro-phenyl)-adamantane-1-carboxylic acid 3-chloro-4-fluoro-benzylamide;

3-(4-Chloro-phenyl)-adamantane-1-carboxylic acid 4-fluoro-3-trifluoromethyl-benzylamide;

3-(4-Chloro-phenyl)-adamantane-1-carboxylic acid 2-chloro-4-fluoro-benzylamide;

3-(4-Chloro-phenyl)-adamantane-1-carboxylic acid 4-chloro-3-trifluoromethyl-benzylamide;

3-(4-Chloro-phenyl)-adamantane-1-carboxylic acid 3-aminomethyl-2,4,5,6-tetrachloro-benzylamide;

3-(4-Chloro-phenyl)-adamantane-1-carboxylic acid [1-(4-chloro-phenyl)-ethyl]-amide;

3-(4-Chloro-phenyl)-adamantane-1-carboxylic acid [1-(4-bromo-phenyl)-ethyl]-amide;

3-(4-Chloro-phenyl)-adamantane-1-carboxylic acid 4-methanesulfonyl-benzylamide;

3-(4-Chloro-phenyl)-adamantane-1-carboxylic acid 4-dimethylamino-benzylamide;

3-(4-Chloro-phenyl)-adamantane-1-carboxylic acid 4-trifluoromethoxy-benzylamide;

3-(4-Chloro-phenyl)-adamantane-1-carboxylic acid 3-trifluoromethoxy-benzylamide;

3-(4-Chloro-phenyl)-adamantane-1-carboxylic acid 4-phenoxy-benzylamide;

3-(4-Chloro-phenyl)-adamantane-1-carboxylic acid 3,4-dihydroxy-benzylamide;
3-(4-Chloro-phenyl)-adamantane-1-carboxylic acid phenethyl-amide;
3-(4-Chloro-phenyl)-adamantane-1-carboxylic acid [2-(4-fluoro-phenyl)-ethyl]-amide;
3-(4-Chloro-phenyl)-adamantane-1-carboxylic acid [2-(4-bromo-phenyl)-ethyl]-amide;
3-(4-Chloro-phenyl)-adamantane-1-carboxylic acid [2-(4-hydroxy-phenyl)-ethyl]-amide;
3-(4-Chloro-phenyl)-adamantane-1-carboxylic acid 4-phenoxy-benzylamide;
3-(4-Chloro-phenyl)-adamantane-1-carboxylic acid [2-(3-bromo-4-methoxy-phenyl)-ethyl]-amide;
3-(4-Chloro-phenyl)-adamantane-1-carboxylic acid [2-(3,4-dihydroxy-phenyl)-ethyl]-amide;
3-(4-Chloro-phenyl)-adamantane-1-carboxylic acid (2-benzo[1,3]dioxol-5-yl-ethyl)-amide;
3-(4-Chloro-phenyl)-adamantane-1-carboxylic acid [2-(3-phenoxy-phenyl)-ethyl]-amide;
3-(4-Chloro-phenyl)-adamantane-1-carboxylic acid [2-(4-phenoxy-phenyl)-ethyl]-amide;
3-(4-Chloro-phenyl)-adamantane-1-carboxylic acid (3-phenyl-propyl)-amide;
3-(4-Chloro-phenyl)-adamantane-1-carboxylic acid (biphenyl-4-ylmethyl)-amide;
3-(4-Chloro-phenyl)-adamantane-1-carboxylic acid (1-methyl-piperidin-4-yl)-amide;
3-(4-Chloro-phenyl)-adamantane-1-carboxylic acid (4-methyl-piperazin-1-yl)-amide;
3-(4-Chloro-phenyl)-adamantane-1-carboxylic acid (3-pyrrolidin-1-yl-propyl)-amide;
3-(4-Chloro-phenyl)-adamantane-1-carboxylic acid [3-(2-oxo-pyrrolidin-1-yl)-propyl]-amide;
3-(4-Chloro-phenyl)-adamantane-1-carboxylic acid [2-(1-methyl-pyrrolidin-2-yl)-ethyl]-amide;
3-(4-Chloro-phenyl)-adamantane-1-carboxylic acid (2-morpholin-4-yl-ethyl)-amide;
3-(4-Chloro-phenyl)-adamantane-1-carboxylic acid (2-piperazin-1-yl-ethyl)-amide;
3-(4-Fluoro-phenyl)-adamantane-1-carboxylic acid (pyridin-4-ylmethyl)-amide;
3-(4-Chloro-phenyl)-adamantane-1-carboxylic acid (pyridin-4-ylmethyl)-amide;
3-(4-Chloro-phenyl)-adamantane-1-carboxylic acid (2-pyridin-4-yl-ethyl)-amide;
3-(4-Chloro-phenyl)-adamantane-1-carboxylic acid (3-imidazol-1-yl-propyl)-amide;
3-(4-Chloro-phenyl)-adamantane-1-carboxylic acid (2-methyl-1H-indol-5-yl)-amide;
3-(4-Chloro-phenyl)-adamantane-1-carboxylic acid (1H-tetrazol-5-yl)-amide;
3-(4-Chloro-phenyl)-adamantane-1-carboxylic acid (9-ethyl-9H-carbazol-3-yl)-amide;
3-(4-Chloro-phenyl)-adamantane-1-carboxylic acid [4-(4-chloro-phenyl)-thiazol-2-yl]-amide;
3-(4-Chloro-phenyl)-adamantane-1-carboxylic acid benzothiazol-2-ylamide;
3-(4-Chloro-phenyl)-adamantane-1-carboxylic acid (5-chloro-benzooxazol-2-yl)-amide;
3-(4-Chloro-phenyl)-adamantane-1-carboxylic acid (9H-purin-6-yl)-amide;
3-(4-Chloro-phenyl)-adamantane-1-carboxylic acid (4-hydroxyphenyl)-amide;
[3-(4-Chloro-phenyl)-adamantan-1-ylmethyl]-(4-trifluoromethyl-benzyl)-amine;
[3-(4-Chloro-phenyl)-adamantan-1-ylmethyl]-(2-fluoro-4-trifluoromethyl-benzyl)-amine;
[3-(4-Chloro-phenyl)-adamantan-1-ylmethyl]-(4-fluoro-3-trifluoromethyl-benzyl)-amine;
[3-(4-Chloro-phenyl)-adamantan-1-ylmethyl]-(4-trifluoromethoxy-benzyl)-amine;
[3-(4-Chloro-phenyl)-adamantan-1-ylmethyl]-[2-(3-phenoxy-phenyl)-ethyl]-amine;
[3-(4-Chloro-phenyl)-adamantan-1-ylmethyl]-(1-methyl-piperidin-4-yl)-amine;
[3-(4-Chloro-phenyl)-adamantan-1-ylmethyl]-(4-methyl-piperazin-1-yl)-amine;
[3-(4-Chloro-phenyl)-adamantan-1-ylmethyl]-(3-pyrrolidin-1-yl-propyl)-amine;
[3-(4-Chloro-phenyl)-adamantan-1-ylmethyl]-[2-(1-methyl-pyrrolidin-2-yl)-ethyl]-amine;
[3-(4-Chloro-phenyl)-adamantan-1-ylmethyl]-(2-morpholin-4-yl-ethyl)-amine;
[3-(4-Chloro-phenyl)-adamantan-1-ylmethyl]-pyridin-4-ylmethyl-amine;
[3-(4-Chloro-phenyl)-adamantan-1-ylmethyl]-(9-ethyl-9H-carbazol-3-yl)-amine;
[3-(4-Chloro-phenyl)-adamantan-1-ylmethyl]-[5-(4-chloro-phenyl)-thiazol-2-yl]-amine;
Phenyl-[1-(3-phenyl-adamantan-1-yl)-ethyl]-amine;
{1-[3-(4-Fluoro-phenyl)-adamantan-1-yl]-ethyl}-phenyl-amine;
{1-[3-(4-Chloro-phenyl)-adamantan-1-yl]-ethyl}-phenyl-amine;
Benzyl-[1-(3-phenyl-adamantan-1-yl)-ethyl]-amine;
Benzyl-{1-[3-(4-fluoro-phenyl)-adamantan-1-yl]-ethyl}-amine;
Benzyl-{1-[3-(4-chloro-phenyl)-adamantan-1-yl]-ethyl}-amine;
(4-tert-Butyl-benzyl)-{1-[3-(4-chloro-phenyl)-adamantan-1-yl]-ethyl}-amine;
[1-(4-Bromo-phenyl)-ethyl]-{1-[3-(4-chloro-phenyl)-adamantan-1-yl]-ethyl}-amine;
[2-(4-Bromo-phenyl)-ethyl]-{1-[3-(4-chloro-phenyl)-adamantan-1-yl]-ethyl}-amine;
(1-Methyl-piperidin-4-yl)-[1-(3-phenyl-adamantan-1-yl)-ethyl]-amine;
{1-[3-(4-Fluoro-phenyl)-adamantan-1-yl]-ethyl}-(1-methyl-piperidin-4-yl)-amine;
{1-[3-(4-Chloro-phenyl)-adamantan-1-yl]-ethyl}-(1-methyl-piperidin-4-yl)-amine;
{1-[3-(4-Chloro-phenyl)-adamantan-1-yl]-ethyl}-(4-methyl-piperazin-1-yl)-amine;
{1-[3-(Phenyl)-adamantan-1-yl]-ethyl}-pyridin-4-ylmethyl-amine;
{1-[3-(4-Chloro-phenyl)-adamantan-1-yl]-ethyl}-(6-chloro-pyridin-3-ylmethyl)-amine;
{1-[3-(4-Chloro-phenyl)-adamantan-1-yl]-ethyl}-(2-pyridin-4-yl-ethyl)-amine;
{1-[3-(4-Chloro-phenyl)-adamantan-1-yl]-ethyl}-(3H-imidazol-4-ylmethyl)-amine;
{1-[3-(4-Chloro-phenyl)-adamantan-1-yl]-ethyl}-(2-methyl-1H-indol-5-yl)-amine;
{1-[3-(4-Chloro-phenyl)-adamantan-1-yl]-ethyl}-(9-ethyl-9H-carbazol-3-yl)-amine;
{1-[3-(4-Chloro-phenyl)-adamantan-1-yl]-ethyl}-(9-ethyl-9H-carbazol-3-ylmethyl)-amine;
9-Ethyl-9H-carbazole-3-carboxylic acid {1-[3-(4-chloro-phenyl)-adamantan-1-yl]-ethyl}-amide;
(4-Bromo-thiophen-2-ylmethyl)-{1-[3-(4-chloro-phenyl)-adamantan-1-yl]-ethyl}-amine;

{1-[3-(4-Chloro-phenyl)-adamantan-1-yl]-ethyl}-(4-phenyl-thiophen-2-ylmethyl)-amine;

or a pharmaceutically acceptable salt thereof.

14. A method according to claim 1 wherein the compound has the structure

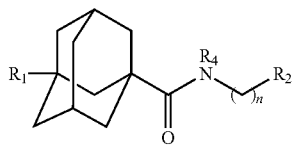

in which $R_1$ is phenyl, 4-chlorophenyl or 4-fluorophenyl;

$R_2$ is 4-pyridyl, optionally substituted with up to 4 groups that are independently $(C_1-C_6)$alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2$H, —SH, —S-alkyl, —SOR'R", —$SO_2$R', —$NO_2$, or NR'R", wherein R' and R" are independently H or $(C_1-C_6)$alkyl, and wherein each alkyl portion of a substituent is optionally further substituted with 1, 2, or 3 groups independently selected from halogen, CN, OH, and $NH_2$;

$R_4$ is H or alkyl; and n is 1 or 2.

15. A method according to claim 1, wherein the compound is:

3-(4-fluorophenyl)-N-(pyridin-4-ylmethyl)adamantane-1-carboxamide;

3-(4-chlorophenyl)-N-(pyridin-4-ylmethyl)adamantane-1-carboxamide; or 3-(4-chlorophenyl)-N-(2-pyridin-4-ylethyl)adamantane-1-carboxamide, or a pharmaceutically acceptable salt thereof.

16. A method according to claim 1, wherein the compound is 3-(4-chlorophenyl)-N-(pyridin-4-ylmethyl)adamantane-1-carboxamide.

17. A method of treating breast cancer in a patient in need of such treatment, the method comprising administering to the patient a compound selected from the group consisting of 3-(4-chlorophenyl)-N-[2-(3,4-dihydroxy-phenyl)-ethyl]adamantane-1-carboxamide;

3-(4-chlorophenyl)-N-(1-methylpiperidin-4-yl)adamantane-1-carboxamide;

3-(4-chlorophenyl)-N-[2-(1-methyl-pyrrolidin-2-yl)-ethyl]adamantane-1-carboxamide;

3-(4-chlorophenyl)-N-(pyridin-4-ylmethyl)adamantane-1-carboxamide; and

N-{1-[3-(4-chlorophenyl)adamantan-1-yl]-ethyl}-1-methylpiperidin-4-amine, or a pharmaceutically acceptable salt thereof.

18. A method according to claim 17, wherein the compound is 3-(4-chlorophenyl)-N-(pyridin-4-ylmethyl)adamantane-1-carboxamide.

19. A method according to claim 17, wherein the compound is 3-(4-chlorophenyl)-N-(1-methylpiperidin-4-yl)adamantane-1-carboxamide.

20. A method of treating arthritis in a patient in need of such treatment, the method comprising administering to the patient 3-(4-chlorophenyl)-N-(pyridin-4-ylmethyl)adamantane-1-carboxamide or a pharmaceutically acceptable salt thereof.

* * * * *